(12) United States Patent
Leuthardt et al.

(10) Patent No.: US 9,024,976 B2
(45) Date of Patent: *May 5, 2015

(54) POSTURAL INFORMATION SYSTEM AND METHOD

(75) Inventors: Eric C. Leuthardt, St. Louis, MO (US); Royce A. Levien, Lexington, MA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 442 days.

This patent is subject to a terminal disclaimer.

(21) Appl. No.: 12/383,818

(22) Filed: Mar. 25, 2009

(65) Prior Publication Data

US 2010/0228489 A1    Sep. 9, 2010

Related U.S. Application Data

(63) Continuation-in-part of application No. 12/381,144, filed on Mar. 5, 2009, and a continuation-in-part of application No. 12/381,200, filed on Mar. 6, 2009, and a continuation-in-part of application No. 12/381,370, (Continued)

(51) Int. Cl.
| | |
|---|---|
| *G06T 3/40* | (2006.01) |
| *A61B 5/00* | (2006.01) |
| *A61B 5/11* | (2006.01) |
| *G09B 19/00* | (2006.01) |
| *G06F 19/00* | (2011.01) |

(52) U.S. Cl.
CPC .............. *A61B 5/1113* (2013.01); *A61B 5/0002* (2013.01); *A61B 5/1112* (2013.01); *A61B 5/1116* (2013.01); *A61B 5/4561* (2013.01); *G06F 19/3437* (2013.01); *G06F 19/345* (2013.01); *G06F 19/3487* (2013.01); *G09B 19/00* (2013.01)

(58) Field of Classification Search
USPC ................ 340/573.7; 600/587, 595; 345/660; 700/90; 705/2; 709/224
See application file for complete search history.

(56) References Cited

U.S. PATENT DOCUMENTS

| | | | |
|---|---|---|---|
| 4,857,716 A | * | 8/1989 | Gombrich et al. ............ 235/375 |
| 5,488,391 A | | 1/1996 | Favot et al. |
| 5,505,605 A | | 4/1996 | Yeh |

(Continued)

FOREIGN PATENT DOCUMENTS

| | | |
|---|---|---|
| DE | 4424146 C1 | 11/1995 |
| WO | WO 2008/010510 | 1/2008 |

(Continued)

OTHER PUBLICATIONS

Dimitrijevic et al.; "Human Body Pose Detection Using Bayesian Spatio-Temporal Templates"; Science Direct—Computer Vision and Image Understanding; bearing a date of 2006; pp. 127-139; vol. 104; Elsevier Inc.; ;located at: www.sciencedirect.com.

(Continued)

*Primary Examiner* — Max Hindenburg

(57) ABSTRACT

A system includes, but is not limited to, a obtaining information module configured for obtaining user advisory information including information regarding one or more users each of two or more devices based at least in part upon physical status information including information regarding one or more spatial aspects of one or more portions of each of the two or more devices, and an output module configured for outputting output information based at least in part upon one or more elements of the user advisory information.

12 Claims, 41 Drawing Sheets

Related U.S. Application Data filed on Mar. 10, 2009, and a continuation-in-part of application No. 12/381,522, filed on Mar. 11, 2009, and a continuation-in-part of application No. 12/381,681, filed on Mar. 13, 2009, and a continuation-in-part of application No. 12/383,261, filed on Mar. 20, 2009, and a continuation-in-part of application No. 12/383,452, filed on Mar. 23, 2009, and a continuation-in-part of application No. 12/383,583, filed on Mar. 24, 2009.

(56) References Cited

U.S. PATENT DOCUMENTS

| | | | |
|---|---|---|---|
| 5,506,605 A | | 4/1996 | Paley |
| 5,570,301 A | | 10/1996 | Barrus |
| 5,686,940 A | | 11/1997 | Kuga |
| 5,792,025 A | | 8/1998 | Kikinis |
| 5,831,260 A | | 11/1998 | Hansen |
| 5,857,855 A | | 1/1999 | Katayama |
| 5,868,647 A | | 2/1999 | Belsole |
| 5,930,152 A | | 7/1999 | Dumont et al. |
| 6,083,248 A | * | 7/2000 | Thompson ............ 607/30 |
| 6,131,874 A | | 10/2000 | Vance et al. |
| 6,141,293 A | | 10/2000 | Amorai-Moriya et al. |
| 6,161,806 A | | 12/2000 | Crosson |
| 6,244,711 B1 | | 6/2001 | Fateh et al. |
| 6,352,516 B1 | | 3/2002 | Pozos et al. |
| 6,409,687 B1 | | 6/2002 | Foxlin |
| 6,535,225 B1 | | 3/2003 | Shintaku et al. |
| 6,602,185 B1 | * | 8/2003 | Uchikubo ............ 600/118 |
| 6,614,364 B1 | | 9/2003 | Yeh |
| 6,673,026 B2 | | 1/2004 | Pozos et al. |
| 6,674,459 B2 | | 1/2004 | Ben-Shachar et al. |
| 6,675,130 B2 | | 1/2004 | Kanevsky et al. |
| 6,762,686 B1 | * | 7/2004 | Tabe ............ 340/573.1 |
| 6,834,436 B2 | | 12/2004 | Townsend et al. |
| 6,961,540 B1 | * | 11/2005 | Kondoh ............ 455/41.2 |
| 6,964,370 B1 | | 11/2005 | Hagale et al. |
| 6,984,208 B2 | | 1/2006 | Zheng |
| 7,163,263 B1 | | 1/2007 | Kurrasch et al. |
| 7,210,240 B2 | | 5/2007 | Townsend et al. |
| 7,248,995 B2 | | 7/2007 | Itsuji et al. |
| 7,315,249 B2 | | 1/2008 | Littell |
| 7,353,151 B2 | | 4/2008 | Furusu et al. |
| 7,567,200 B1 | | 7/2009 | Osterweil |
| 7,616,187 B2 | | 11/2009 | Koo et al. |
| 7,630,832 B2 | | 12/2009 | Kim et al. |
| 7,753,861 B1 | | 7/2010 | Kahn et al. |
| 7,782,358 B2 | | 8/2010 | Nieminen et al. |
| 7,933,678 B2 | | 4/2011 | Diezel et al. |
| 7,988,647 B2 | | 8/2011 | Bunn et al. |
| 8,024,202 B2 | * | 9/2011 | Carroll et al. ............ 705/3 |
| 8,074,181 B2 | * | 12/2011 | Zaman et al. ............ 715/784 |
| 8,075,449 B2 | | 12/2011 | Lee |
| 8,089,468 B2 | * | 1/2012 | Locker et al. ............ 345/168 |
| 8,089,827 B2 | * | 1/2012 | Carotenuto ............ 367/128 |
| 8,139,034 B2 | * | 3/2012 | Albouyeh et al. ............ 345/168 |
| 8,469,901 B2 | | 6/2013 | Teicher et al. |
| 8,487,750 B2 | | 7/2013 | Reijndorp et al. |
| 8,745,541 B2 | | 6/2014 | Wilson et al. |
| 2001/0015792 A1 | | 8/2001 | Fateh et al. |
| 2001/0049482 A1 | | 12/2001 | Pozos et al. |
| 2002/0008621 A1 | | 1/2002 | Barritz et al. |
| 2002/0028003 A1 | | 3/2002 | Krebs et al. |
| 2004/0010328 A1 | | 1/2004 | Carson et al. |
| 2004/0030531 A1 | | 2/2004 | Miller et al. |
| 2004/0109012 A1 | | 6/2004 | Kraus et al. |
| 2004/0143176 A1 | * | 7/2004 | Foxlin ............ 600/395 |
| 2004/0195876 A1 | | 10/2004 | Huiban |
| 2004/0208496 A1 | | 10/2004 | Pilu |
| 2004/0211883 A1 | | 10/2004 | Imagawa et al. |
| 2004/0222892 A1 | | 11/2004 | Balaban et al. |
| 2004/0239161 A1 | | 12/2004 | Lee |
| 2004/0249872 A1 | | 12/2004 | Hsieh |
| 2005/0160814 A1 | | 7/2005 | Vaganov et al. |
| 2005/0278157 A1 | | 12/2005 | Raschke |
| 2006/0027404 A1 | * | 2/2006 | Foxlin ............ 178/18.06 |
| 2006/0074338 A1 | | 4/2006 | Greenwald et al. |
| 2006/0125787 A1 | | 6/2006 | Cheng |
| 2006/0193270 A1 | | 8/2006 | Gehasie et al. |
| 2006/0227103 A1 | | 10/2006 | Koo et al. |
| 2006/0241520 A1 | | 10/2006 | Robertson |
| 2006/0241521 A1 | | 10/2006 | Cohen |
| 2007/0009243 A1 | | 1/2007 | Takahashi |
| 2007/0149360 A1 | | 6/2007 | Narayanaswami |
| 2007/0244633 A1 | | 10/2007 | Phillips et al. |
| 2007/0265533 A1 | | 11/2007 | Tran |
| 2007/0287931 A1 | | 12/2007 | Dilorenzo |
| 2008/0015903 A1 | | 1/2008 | Rodgers |
| 2008/0140137 A1 | | 6/2008 | Wall, III et al. |
| 2008/0170118 A1 | | 7/2008 | Albertson et al. |
| 2008/0226136 A1 | | 9/2008 | Takaku et al. |
| 2009/0030767 A1 | | 1/2009 | Morris et al. |
| 2009/0046111 A1 | | 2/2009 | Joachim et al. |
| 2009/0058661 A1 | | 3/2009 | Gleckler et al. |
| 2009/0076418 A1 | * | 3/2009 | Jung et al. ............ 600/595 |
| 2009/0079813 A1 | | 3/2009 | Hildreth |
| 2009/0082699 A1 | | 3/2009 | Bang et al. |
| 2009/0228841 A1 | | 9/2009 | Hildreth |
| 2009/0273441 A1 | | 11/2009 | Mukherjee |
| 2010/0004037 A1 | | 1/2010 | Ozawa |
| 2010/0026720 A1 | | 2/2010 | Hotta et al. |
| 2010/0094645 A1 | | 4/2010 | Carroll et al. |
| 2010/0198374 A1 | | 8/2010 | Carson et al. |
| 2010/0225473 A1 | | 9/2010 | Leuthardt et al. |
| 2010/0225474 A1 | | 9/2010 | Leuthardt et al. |
| 2010/0225490 A1 | | 9/2010 | Leuthardt et al. |
| 2010/0225491 A1 | | 9/2010 | Leuthardt et al. |
| 2010/0225498 A1 | | 9/2010 | Leuthardt et al. |
| 2010/0228153 A1 | | 9/2010 | Leuthardt et al. |
| 2010/0228154 A1 | | 9/2010 | Leuthardt et al. |
| 2010/0228158 A1 | | 9/2010 | Leuthardt et al. |
| 2010/0228159 A1 | | 9/2010 | Leuthardt et al. |
| 2010/0228487 A1 | | 9/2010 | Leuthardt et al. |
| 2010/0228488 A1 | | 9/2010 | Leuthardt et al. |
| 2010/0228490 A1 | | 9/2010 | Leuthardt et al. |
| 2010/0228492 A1 | | 9/2010 | Leuthardt et al. |
| 2010/0228493 A1 | | 9/2010 | Leuthardt et al. |
| 2010/0228494 A1 | | 9/2010 | Leuthardt et al. |
| 2010/0228495 A1 | | 9/2010 | Leuthardt et al. |
| 2010/0271200 A1 | | 10/2010 | Leuthardt et al. |
| 2013/0201135 A1 | | 8/2013 | Ludwig |

FOREIGN PATENT DOCUMENTS

| | | |
|---|---|---|
| WO | WO 2008/075497 | 6/2008 |
| WO | WO 2009/018139 A1 | 2/2009 |

OTHER PUBLICATIONS

Galloway et al.; "Interactive Image-Guided Neurosurgery"; IEEE Transactions on Biomedical Engineering; bearing a date of Dec. 1992; pp. 1226-1231; vol. 39, No. 12; IEEE.

Kato et al.; "A Frameless, Armless Navigational System for Computer-Assisted Neurosurgery"; Journal of Neurosurgery; bearing a date of May 1991; pp. 845-849; vol. 74.

"The Immune System—in More Detail"; Nobelprize.org; bearing a date of Apr. 2, 2013, first published Nov. 8, 2004; 6 pages; Nobel Media AB 2013; located at: http://www.nobelprize.org/educational/medicine/immunity/immune-detail.html.

Ankrum, Dennis R.; "Flat Panel Potential for Conformance to the Display Location Requirements of ISO 9241 Parts 3 & 5"; Human-Computer Interaction: Proceedings of HCI International '01; bearing a date of 2001; pp. 497-501.

Honglun et al.; "Research on virtual human in ergonomic simulation"; Computer & Industrial Engineering; bearing a date of Jun. 15, 2007; pp. 350-356; vol. 53; Elsevier Ltd.

Jayaram et al.; "Introducing quantitative analysis methods into virtual environments for real-time and continuous ergonomic evaluations"; Computers in Industry; bearing a date of Dec. 15, 2005; pp. 283-296; vol. 57; Elsevier B.V.

(56) References Cited

OTHER PUBLICATIONS

Openshaw et al.; "Ergonomics and Design A Reference Guide"; Allsteel; bearing a date of 2006; 64 pages; located at www.allsteeloffice.com/ergo.

Reed et al.; "The HUMOSIM Ergonomics Framework: A New Approach to Digital Human Simulation for Ergonomic Analysis"; Digital Human Modeling for Design and Engineering Conference; Jul. 4-6, 2006; cover page (2) and pp. 1-12; SAE International.

"Nokia N82 Review"; Apr. 10, 2008; pp. 1-4; Published by Tzer2; located at: http://www.ovigaming.com/reviews/item/nokia_n82_reviewl.php.

Nokia N82 User Guide:, Issue 2.0; bearing a date of 2008; pp. 1-183.

* cited by examiner

POSTURAL INFORMATION SYSTEM AND METHOD

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/381,144, entitled POSTURAL INFORMATION SYSTEM AND METHOD, naming Eric C. Leuthardt, Royce A. Levien as inventors, filed 5, Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/381,200, entitled POSTURAL INFORMATION SYSTEM AND METHOD, naming Eric C. Leuthardt, Royce A. Levien as inventors, filed 6, Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/381,370, entitled POSTURAL INFORMATION SYSTEM AND METHOD, naming Eric C. Leuthardt, Royce A. Levien as inventors, filed 10, Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/381,522, entitled POSTURAL INFORMATION SYSTEM AND METHOD, naming Eric C. Leuthardt, Royce A. Levien as inventors, filed 11, Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/381,681, entitled POSTURAL INFORMATION SYSTEM AND METHOD, naming Eric C. Leuthardt, Royce A. Levien as inventors, filed 13, Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/383,261, entitled POSTURAL INFORMATION SYSTEM AND METHOD, naming Eric C. Leuthardt and Royce A. Levien, as inventors, filed 20, Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/383,452, entitled POSTURAL INFORMATION SYSTEM AND METHOD, naming Eric C. Leuthardt and Royce A. Levien, as inventors, filed 23, Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/383,583, entitled POSTURAL INFORMATION SYSTEM AND METHOD, naming Eric C. Leuthardt and Royce A. Levien, as inventors, filed 24, Mar. 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

A method includes, but is not limited to: obtaining user advisory information including information regarding one or more users each of two or more devices based at least in part upon physical status information including information regarding one or more spatial aspects of one or more portions of each of the two or more devices, and outputting output information based at least in part upon one or more elements of the user advisory information. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

A system includes, but is not limited to: circuitry for obtaining user advisory information including information regarding one or more users each of two or more devices based at least in part upon physical status information including information regarding one or more spatial aspects of one or more portions of each of the two or more devices, and circuitry for outputting output information based at least in part upon one or more elements of the user advisory information. In addition to the foregoing, other method aspects are described in the claims, drawings, and text forming a part of the present disclosure.

A system includes, but is not limited to: means for obtaining user advisory information including information regarding one or more users each of two or more devices based at least in part upon physical status information including information regarding one or more spatial aspects of one or more portions of each of the two or more devices, and means for outputting output information based at least in part upon one or more elements of the user advisory information. In addition to the foregoing, other method aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
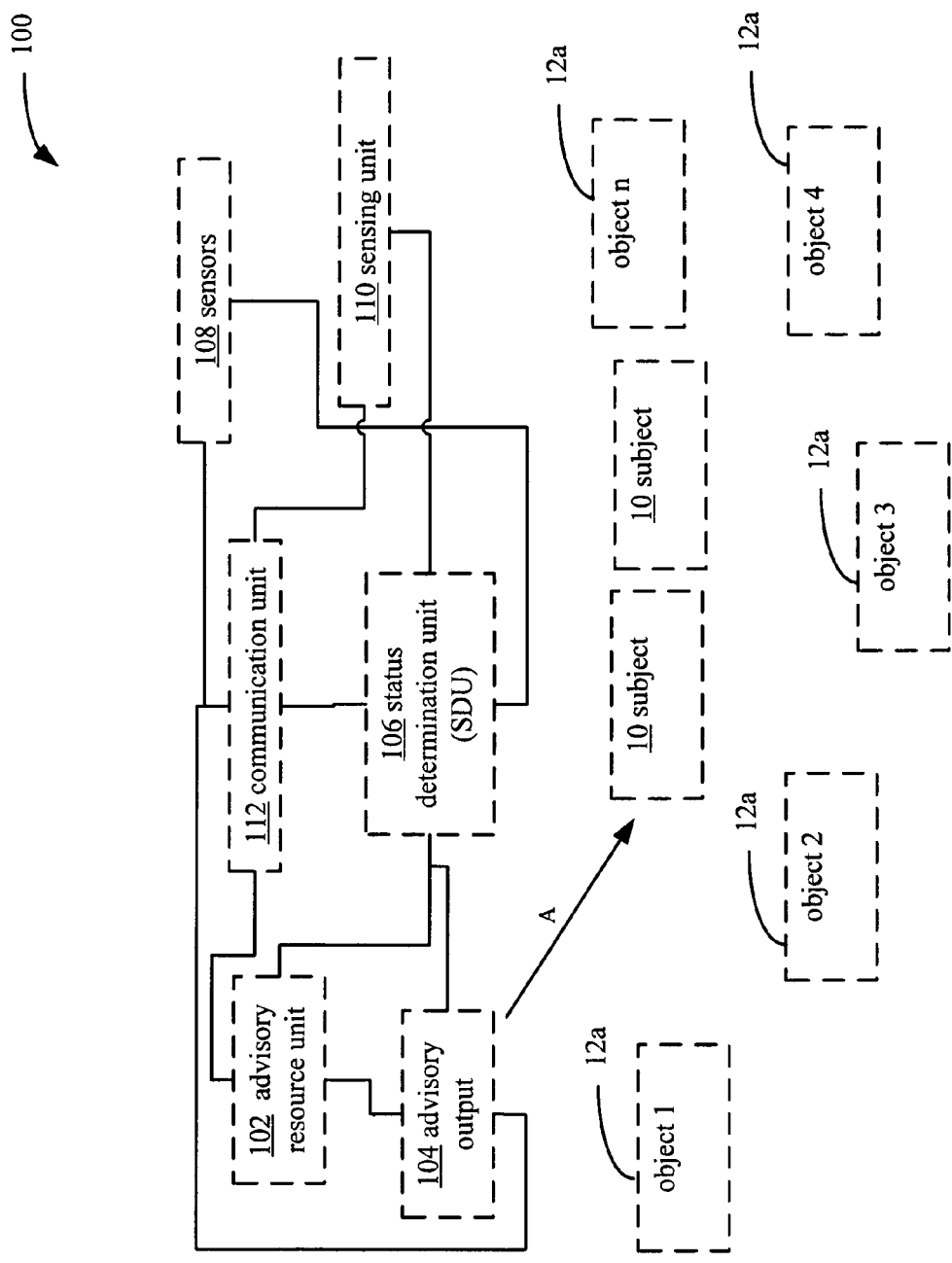
FIG. 1 is a block diagram of a general exemplary implementation of a postural information system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

An exemplary environment is depicted in FIG. 1 in which one or more aspects of various embodiments may be implemented. In the illustrated environment, a general exemplary implementation of a system 100 may include at least an advisory resource unit 102 that is configured to determine advisory information associated at least in part with spatial aspects, such as posture, of at least portions of one or more subjects 10. In the following, one of the subjects 10 depicted in FIG. 1 will be discussed for convenience since in many of the implementations only one subject would be present, but is not intended to limit use of the system 100 to only one concurrent subject.

The subject 10 is depicted in FIG. 1 in an exemplary spatial association with a plurality of objects 12 and/or with one or more surfaces 12a thereof. Such spatial association can influence spatial aspects of the subject 10 such as posture of the subject and thus can be used by the system 10 to determine advisory information regarding spatial aspects, such as posture, of the subject.

For example, the subject 10 can be a human, animal, robot, or other that can have a posture that can be adjusted such that given certain objectives, conditions, environments and other factors, a certain posture or range or other plurality of postures for the subject 10 may be more desirable than one or more other postures. In implementations, desirable posture for the subject 10 may vary over time given changes in one or more associated factors.

Various approaches have introduced ways to determine physical status of a living subject with sensors being directly attached to the subject. Sensors can be used to distinguishing lying, sitting, and standing positions. This sensor data can then be stored in a storage device as a function of time. Multiple points or multiple intervals of the time dependent data can be used to direct a feedback mechanism to provide information or instruction in response to the time dependent output indicating too little activity, too much time with a joint not being moved beyond a specified range of motion, too many motions beyond a specified range of motion, or repetitive activity that can cause repetitive stress injury, etc.

Approaches have included a method for preventing computer induced repetitive stress injuries (CRSI) that records operation statistics of the computer, calculates a computer user's weighted fatigue level; and will automatically remind a user of necessary responses when the fatigue level reaches a predetermined threshold. Some have measured force, primarily due to fatigue, such as with a finger fatigue measuring system, which measures the force output from fingers while the fingers are repetitively generating forces as they strike a keyboard. Force profiles of the fingers have been generated from the measurements and evaluated for fatigue. Systems have been used clinically to evaluate patients, to ascertain the effectiveness of clinical intervention, pre-employment screening, to assist in minimizing the incidence of repetitive stress injuries at the keyboard, mouse, joystick, and to monitor effectiveness of various finger strengthening systems. Systems have also been used in a variety of different applications adapted for measuring forces produced during performance of repetitive motions.

Others have introduced support surfaces and moving mechanisms for automatically varying orientation of the support surfaces in a predetermined manner over time to reduce or eliminate the likelihood of repetitive stress injury as a result of performing repetitive tasks on or otherwise using the support surface. By varying the orientation of the support surface, e.g., by moving and/or rotating the support surface over time, repetitive tasks performed on the support surface are modified at least subtly to reduce the repetitiveness of the individual motions performed by an operator.

Some have introduced attempts to reduce, prevent, or lessen the incidence and severity of repetitive strain injuries ("RSI") with a combination of computer software and hardware that provides a "prompt" and system whereby the computer operator exercises their upper extremities during data entry and word processing thereby maximizing the excursion (range of motion) of the joints involved directly and indirectly in computer operation. Approaches have included 1) specialized target means with optional counters which serves as "goals" or marks towards which the hands of the typist are directed during prolonged key entry, 2) software that directs the movement of the limbs to and from the keyboard, and 3) software that individualizes the frequency and intensity of the exercise sequence.

Others have included a wrist-resting device having one or both of a heater and a vibrator in the device wherein a control system is provided for monitoring user activity and weighting each instance of activity according to stored parameters to accumulate data on user stress level. In the event a prestored stress threshold is reached, a media player is invoked to provide rest and exercise for the user.

Others have introduced biometrics authentication devices to identify characteristics of a body from captured images of the body and to perform individual authentication. The device guides a user, at the time of verification, to the image capture state at the time of registration of biometrics characteristic data. At the time of registration of biometrics characteristic data, body image capture state data is extracted from an image captured by an image capture unit and is registered in a storage unit, and at the time of verification the registered image capture state data is read from the storage unit and is compared with image capture state data extracted at the time of verification, and guidance of the body is provided. Alternatively, an outline of the body at the time of registration, taken from image capture state data at the time of registration, is displayed.

Others have introduced mechanical models of human bodies having rigid segments connected with joints. Such models include articulated rigid-multibody models used as a tool for investigation of the injury mechanism during car crash events. Approaches can be semi-analytical and can be based on symbolic derivatives of the differential equations of motion. They can illustrate the intrinsic effect of human body geometry and other influential parameters on head acceleration.

Some have introduced methods of effecting an analysis of behaviors of substantially all of a plurality of real segments together constituting a whole human body, by conducting a simulation of the behaviors using a computer under a predetermined simulation analysis condition, on the basis of a numerical whole human body model provided by modeling on the computer the whole human body in relation to a skeleton structure thereof including a plurality of bones, and in relation to a joining structure of the whole human body which joins at least two real segments of the whole human body and which is constructed to have at least one real segment of the whole human body, the at least one real segment being selected from at least one ligament, at least one tendon, and at least one muscle, of the whole human body.

Others have introduced spatial body position detection to calculate information on a relative distance or positional relationship between an interface section and an item by detecting an electromagnetic wave transmitted through the interface section, and using the electromagnetic wave from the item to detect a relative position of the item with respective to the interface section. Information on the relative spatial position of an item with respect to an interface section that has an arbitrary shape and deals with transmission of information or signal from one side to the other side of the interface section is detected with a spatial position detection method. An electromagnetic wave radiated from the item and transmitted through the interface section is detected by an electromagnetic wave detection section, and based on the detection result; information on spatial position coordinates of the item is calculated by a position calculation section.

Some introduced a template-based approach to detecting human silhouettes in a specific walking pose with templates having short sequences of 2D silhouettes obtained from motion capture data. Motion information is incorporated into the templates to help distinguish actual people who move in a predictable way from static objects whose outlines roughly resemble those of humans. During the training phase we use statistical learning techniques to estimate and store the relevance of the different silhouette parts to the recognition task. At run-time, Chamfer distance is converted to meaningful probability estimates. Particular templates handle six different camera views, excluding the frontal and back view, as well as different scales and are particularly useful for both indoor and outdoor sequences of people walking in front of cluttered backgrounds and acquired with a moving camera, which makes techniques such as background subtraction impractical.

Further discussion of approaches introduced by others can be found in U.S. Pat. Nos. 5,792,025; 5,868,647; 6,161,806; 6,352,516; 6,673,026; 6,834,436; 7,210,240; 7,248,995; 7,248,995; and 7,353,151; U.S. Patent Application Nos. 20040249872, and 20080226136; "Sensitivity Analysis of the Human Body Mechanical Model", *Zeitschrift für angewandte Mathematik und Mechanik*, 2000, vol. 80, pp. S343-S344, SUP2 (6 ref.); and "Human Body Pose Detection Using Bayesian Spatio-Temporal Templates," *Computer Vision and Image Understanding*, Volume 104, Issues 2-3, November-December 2006, Pages 127-139 M. Dimitrijevic, V. Lepetit and P. Fua Exemplary implementations of the system 100 can also include an advisory output 104, a status determination unit 106, one or more sensors 108, a sensing unit 110, and communication unit 112. In some implementations, the advisory output 104 receives messages containing advisory information from the advisory resource unit 102. In response to the received advisory information, the advisory output 104 sends an advisory to the subject 10 in a suitable form containing information such as related to spatial aspects of the subject and/or one or more of the objects 12.

A suitable form of the advisory can include visual, audio, touch, temperature, vibration, flow, light, radio frequency, other electromagnetic, and/or other aspects, media, and/or indicators that could serve as a form of input to the subject 10.

Spatial aspects can be related to posture and/or other spatial aspects and can include location, position, orientation, visual placement, visual appearance, and/or conformation of one or more portions of one or more of the subject 10 and/or one or more portions of one or more of the object 12. Location can involve information related to landmarks or other objects. Position can involve information related to a coordinate system or other aspect of cartography. Orientation can involve information related to a three dimensional axis system. Visual placement can involve such aspects as placement of display features, such as icons, scene windows, scene widgets, graphic or video content, or other visual features on a display such as a display monitor. Visual appearance can involve such aspects as appearance, such as sizing, of display features, such as icons, scene windows, scene widgets, graphic or video content, or other visual features on a display such as a display monitor. Conformation can involve how various portions including appendages are arranged with respect to one another. For instance, one of the objects 12 may be able to be folded or have movable arms or other structures or portions that can be moved or re-oriented to result in different conformations.

Examples of such advisories can include but are not limited to aspects involving re-positioning, re-orienting, and/or re-configuring the subject 10 and/or one or more of the objects 12. For instance, the subject 10 may use some of the objects 12 through vision of the subject and other of the objects through direct contact by the subject. A first positioning of the objects 12 relative to one another may cause the subject 10 to have a first posture in order to accommodate the subject's visual or direct contact interaction with the objects. An advisory may include content to inform the subject 10 to change to a second posture by re-positioning the objects 12 to a second position so that visual and direct contact use of the objects 12 can be performed in the second posture by the subject. Advisories that involve one or more of the objects 12 as display devices may involve spatial aspects such as visual placement and/or visual appearance and can include, for example, modifying how or what content is being displayed on one or more of the display devices.

The system 100 can also include a status determination unit (SDU) 106 that can be configured to determine physical status of the objects 12 and also in some implementations determine physical status of the subject 10 as well. Physical status can include spatial aspects such as location, position, orientation, visual placement, visual appearance, and/or conformation of the objects 12 and optionally the subject 10. In some implementations, physical status can include other aspects as well.

Figure 2:
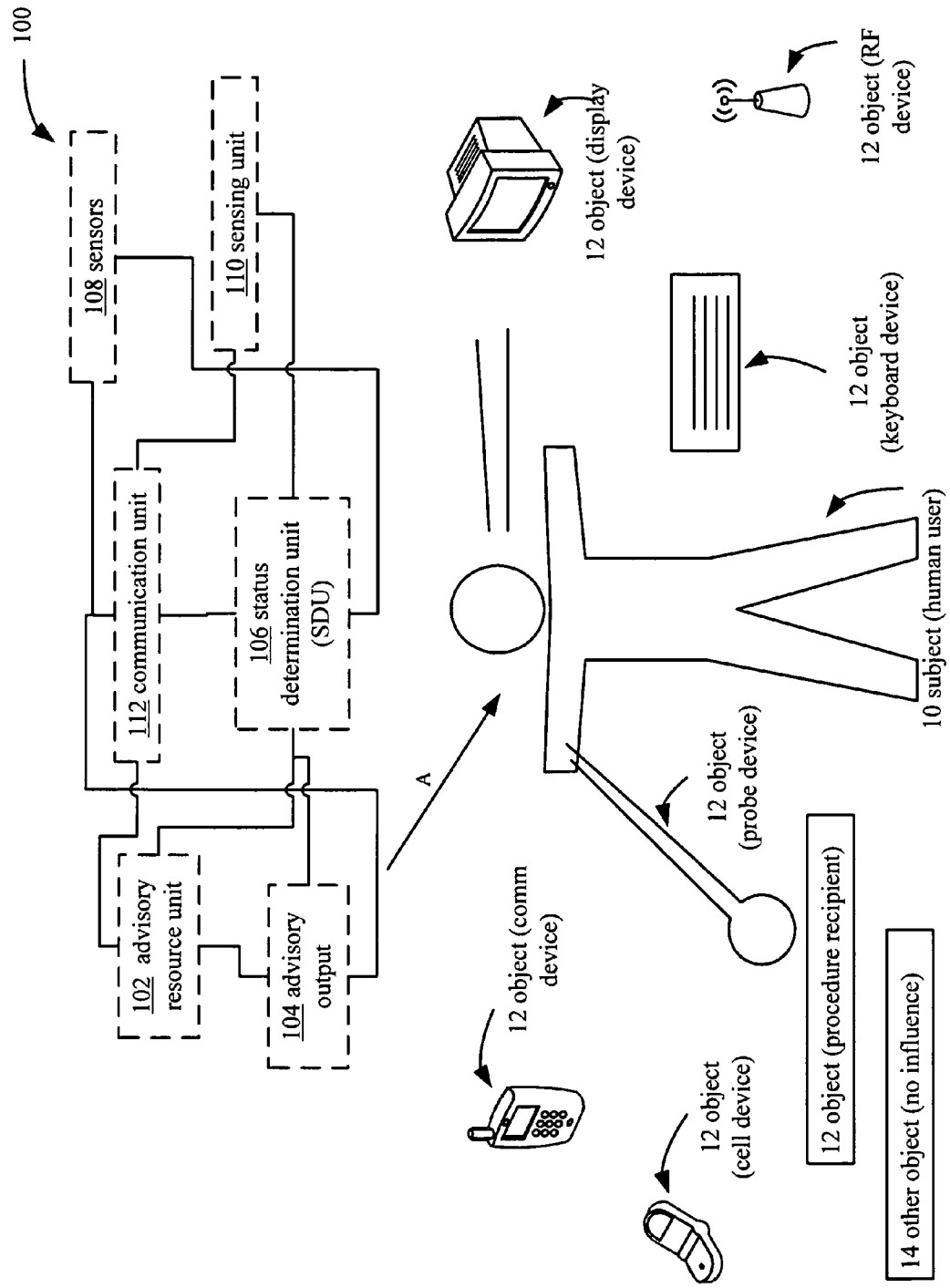
FIG. 2 is a schematic diagram depicting an exemplary environment suitable for application of a first exemplary implementation of the general exemplary implementation of the postural information system of FIG. 1.

The status determination unit 106 can furnish determined physical status that the advisory resource unit 102 can use to provide appropriate messages to the advisory output 104 to generate advisories for the subject 10 regarding posture or other spatial aspects of the subject with respect to the objects 12. In implementations, the status determination unit 106 can use information regarding the objects 12 and in some cases the subject 10 from one or more of the sensors 108 and/or the sensing unit 110 to determine physical status As shown in FIG. 2, an exemplary implementation of the system 100 is applied to an environment in which the objects 12 include a communication device, a cellular device, a probe device servicing a procedure recipient, a keyboard device, a display device, and an RF device and wherein the subject 10 is a human. Also shown is an other object 14 that does not influence the physical status of the subject 10, for instance, the subject is not required to view, touch, or otherwise interact with the other object as to affect the physical status of the subject due to an interaction. The environment depicted in FIG. 2 is merely exemplary and is not intended to limit what types of the subject 10, the objects 12, and the environments can be involved with the system 100. The environments that can be used with the system 100 are far ranging and can include any sort of situation in which the subject 10 is being influenced regarding posture or other spatial aspects of the subject by one or more spatial aspects of the objects 12.

Figure 3:
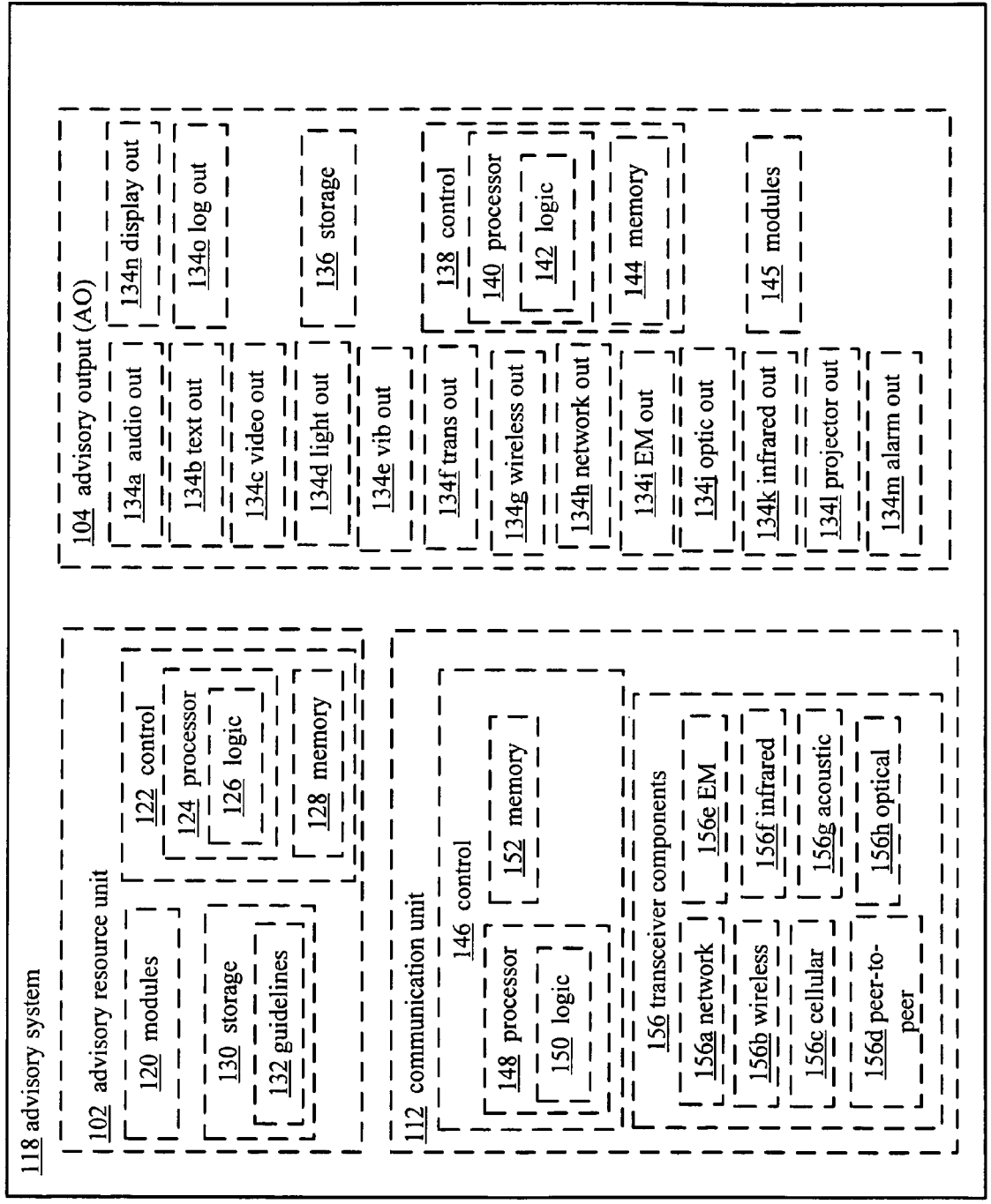
FIG. 3 is a block diagram of an exemplary implementation of an advisory system forming a portion of an implementation of the general exemplary implementation of the postural information system of FIG. 1.

An advisory system 118 is shown in FIG. 3 to optionally include instances of the advisory resource unit 102, the advisory output 104 and a communication unit 112. The advisory resource unit 102 is depicted to have modules 120, a control unit 122 including a processor 124, a logic unit 126, and a memory unit 128, and having a storage unit 130 including guidelines 132. The advisory output 104 is depicted to include an audio output 134a, a textual output 134b, a video output 134c, a light output 134d, a vibrator output 134e, a transmitter output 134f, a wireless output 134g, a network output 134h, an electromagnetic output 134i, an optic output 134j, an infrared output 134k, a projector output 134l, an alarm output 134m, a display output 134n, and a log output 134o, a storage unit 136, a control 138, a processor 140 with a logic unit 142, a memory 144, and modules 145.

The communication unit 112 is depicted in FIG. 3 to optionally include a control unit 146 including a processor 148, a logic unit 150, and a memory 152 and to have transceiver components 156 including a network component 156a, a wireless component 156b, a cellular component 156c, a peer-to-peer component 156d, an electromagnetic (EM) component 156e, an infrared component 156f, an acoustic component 156g, and an optical component 156h. In general, similar or corresponding systems, units, components, or other parts are designated with the same reference number throughout, but each with the same reference number can be internally composed differently. For instance, the communication unit 112 is depicted in various Figures as being used by various components, systems, or other items such as in instances of the advisory system in FIG. 3, in the status determination system of FIG. 6, and in the object of FIG. 10, but is not intended that the same instance or copy of the communication unit 112 is used in all of these cases, but rather various versions of the communication unit having different internal composition can be used to satisfy the requirements of each specific instance.

Figure 4:
FIG. 4 is a block diagram of an exemplary implementation of modules for an advisory resource unit 102 of the advisory system 118 of FIG. 3.

The modules 120 is further shown in FIG. 4 to optionally include a determining device location module 120a, a determining user location module 120b, a determining device orientation module 120c, a determining user orientation module 120d, a determining device position module 120e, a determining user position module 120f, a determining device conformation module 120g, a determining user conformation module 120h, a determining device schedule module 120i, a determining user schedule module 120j, a determining use duration module 120k, a determining user duration module 120l, a determining postural adjustment module 120m, a determining ergonomic adjustment module 120n, a determining robotic module 120p, a determining advisory module 120q, and an other modules 120r.

Figure 5:
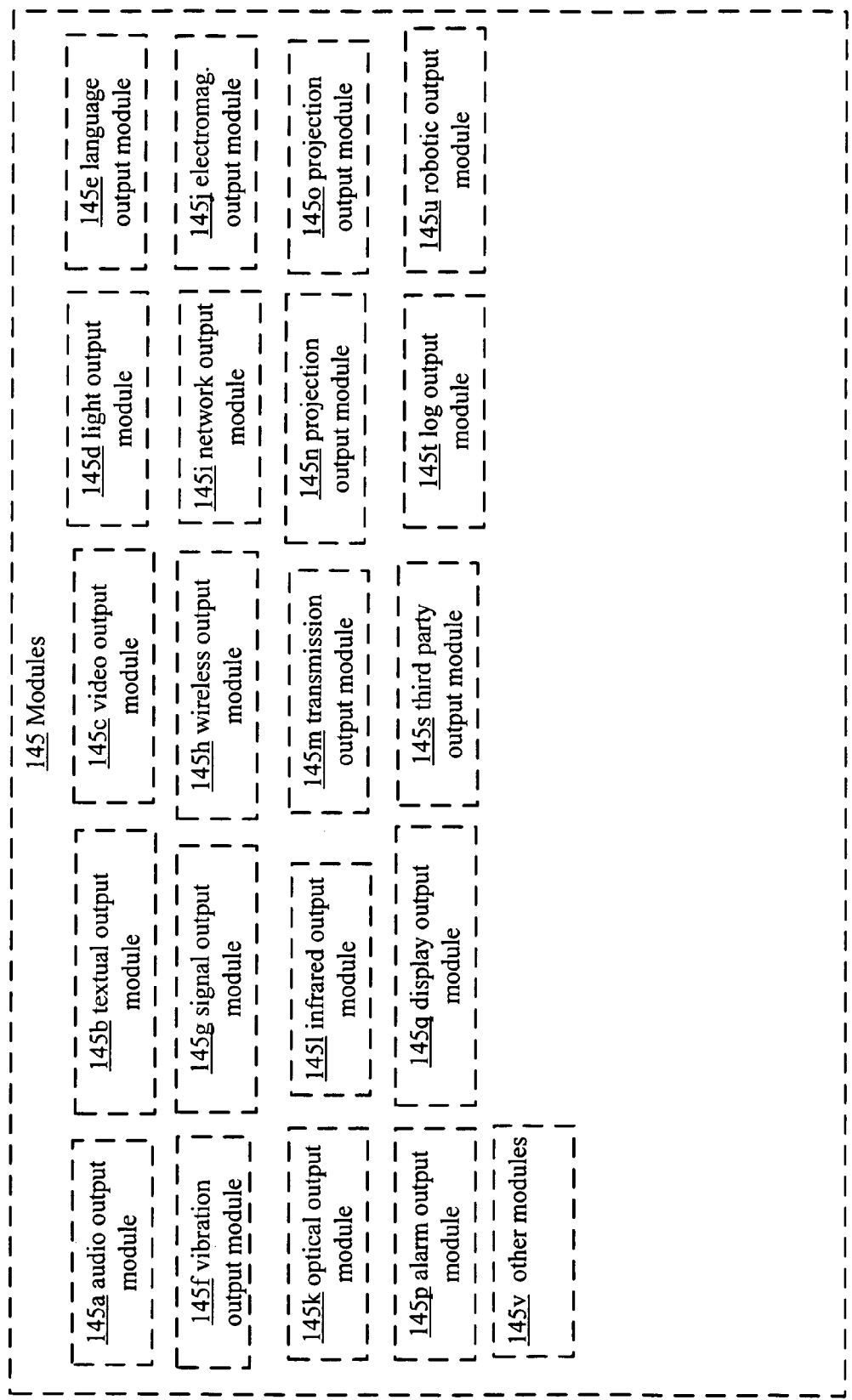
FIG. 5 is a block diagram of an exemplary implementation of modules for an advisory output 104 of the advisory system 118 of FIG. 3.

The modules 145 is further shown in FIG. 5 to optionally include an audio output module 145a, a textual output module 145b, a video output module 145c, a light output module 145d, a language output module 145e, a vibration output module 145f, a signal output module 145g, a wireless output module 145h, a network output module 145i, an electromagnetic output module 145j, an optical output module 145k, an infrared output module 145l, a transmission output module 145m, a projection output module 145n, a projection output module 145o, an alarm output module 145p, a display output module 145q, a third party output module 145s, a log output module 145t, a robotic output module 145u, and an other modules 145v.

Figure 6:
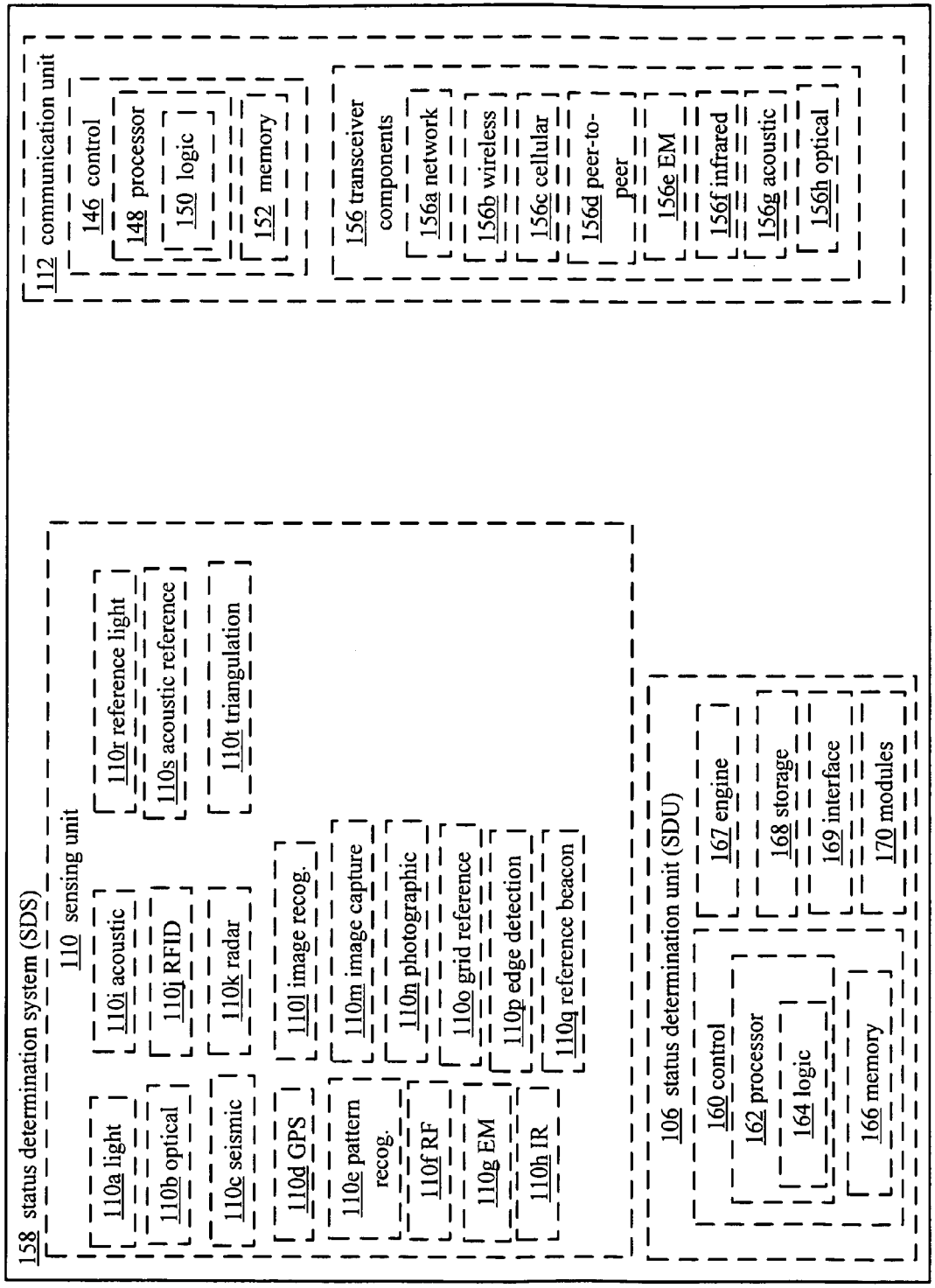
FIG. 6 is a block diagram of an exemplary implementation of a status determination system (SPS) forming a portion of an implementation of the general exemplary implementation of the postural information system of FIG. 1.

A status determination system (SDS) 158 is shown n FIG. 6 to optionally include the communication unit 112, the sensing unit 110, and the status determination unit 106. The sensing unit 110 is further shown to optionally include a light based sensing component 110a, an optical based sensing component 110b, a seismic based sensing component 110c, a global positioning system (GPS) based sensing component 110d, a pattern recognition based sensing component 110e, a radio frequency based sensing component 110f, an electromagnetic (EM) based sensing component 110g, an infrared (IR0 sensing component 110h, an acoustic based sensing component 110i, a radio frequency identification (RFID) based sensing component 110j, a radar based sensing component 110k, an image recognition based sensing component 110l, an image capture based sensing component 110m, a photographic based sensing component 110n, a grid reference based sensing component 110o, an edge detection based sensing component 110p, a reference beacon based sensing component 110q, a reference light based sensing component 110r, an acoustic reference based sensing component 110s, and a triangulation based sensing component 110t.

The sensing unit 110 can include use of one or more of its various based sensing components to acquire information on physical status of the subject 10 and the objects 12 even when the subject and the objects maintain a passive role in the process. For instance, the light based sensing component 110a can include light receivers to collect light from emitters or ambient light that was reflected off or otherwise have interacted with the subject 10 and the objects 12 to acquire physical status information regarding the subject and the objects. The optical based sensing component 110b can include optical based receivers to collect light from optical emitters that have interacted with the subject 10 and the objects 12 to acquire physical status information regarding the subject and the objects.

For instance, the seismic based sensing component 110c can include seismic receivers to collect seismic waves from seismic emitters or ambient seismic waves that have interacted with the subject 10 and the objects 12 to acquire physical status information regarding the subject and the objects. The global positioning system (GPS) based sensing component 110d can include GPS receivers to collect GPS information associated with the subject 10 and the objects 12 to acquire physical status information regarding the subject and the objects. The pattern recognition based sensing component 110e can include pattern recognition algorithms to operate with the determination engine 167 of the status determination unit 106 to recognize patterns in information received by the sensing unit 110 to acquire physical status information regarding the subject and the objects.

For instance, the radio frequency based sensing component 110f can include radio frequency receivers to collect radio frequency waves from radio frequency emitters or ambient radio frequency waves that have interacted with the subject 10 and the objects 12 to acquire physical status information regarding the subject and the objects. The electromagnetic (EM) based sensing component 110g, can include electromagnetic frequency receivers to collect electromagnetic frequency waves from electromagnetic frequency emitters or ambient electromagnetic frequency waves that have interacted with the subject 10 and the objects 12 to acquire physical status information regarding the subject and the objects. The infrared sensing component 110h can include infrared receivers to collect infrared frequency waves from infrared frequency emitters or ambient infrared frequency waves that have interacted with the subject 10 and the objects 12 to acquire physical status information regarding the subjects and the objects.

For instance, the acoustic based sensing component 110 can include acoustic frequency receivers to collect acoustic frequency waves from acoustic frequency emitters or ambient acoustic frequency waves that have interacted with the subject 10 and the objects 12 to acquire physical status information regarding the subjects and the objects. The radio frequency identification (RFID) based sensing component 110j can include radio frequency receivers to collect radio frequency identification signals from RFID emitters associated with the subject 10 and the objects 12 to acquire physical status information regarding the subjects and the objects. The radar based sensing component 110k can include radar frequency receivers to collect radar frequency waves from radar frequency emitters or ambient radar frequency waves that have interacted with the subject 10 and the objects 12 to acquire physical status information regarding the subjects and the objects.

The image recognition based sensing component 110l can include image receivers to collect images of the subject 10 and the objects 12 and one or more image recognition algorithms to recognition aspects of the collected images optionally in conjunction with use of the determination engine 167 of the status determination unit 106 to acquire physical status information regarding the subjects and the objects.

The image capture based sensing component 110m can include image receivers to collect images of the subject 10 and the objects 12 to acquire physical status information regarding the subjects and the objects. The photographic based sensing component 110n can include photographic cameras to collect photographs of the subject 10 and the objects 12 to acquire physical status information regarding the subjects and the objects.

The grid reference based sensing component 110o can include a grid of sensors (such as contact sensors, photodetectors, optical sensors, acoustic sensors, infrared sensors, or other sensors) adjacent to, in close proximity to, or otherwise located to sense one or more spatial aspects of the objects 12 such as location, position, orientation, visual placement, visual appearance, and/or conformation. The grid reference based sensing component 110o can also include processing aspects to prepare sensed information for the status determination unit 106.

The edge detection based sensing component 110p can include one or more edge detection sensors (such as contact sensors, photo-detectors, optical sensors, acoustic sensors, infrared sensors, or other sensors) adjacent to, in close proximity to, or otherwise located to sense one or more spatial aspects of the objects 12 such as location, position, orientation, visual placement, visual appearance, and/or conformation. The edge detection based sensing component 110p can also include processing aspects to prepare sensed information for the status determination unit 106.

The reference beacon based sensing component 110q can include one or more reference beacon emitters and receivers (such as acoustic, light, optical, infrared, or other) located to send and receive a reference beacon to calibrate and/or otherwise detect one or more spatial aspects of the objects 12 such as location, position, orientation, visual placement, visual appearance, and/or conformation. The reference beacon based sensing component 110q can also include processing aspects to prepare sensed information for the status determination unit 106.

The reference light based sensing component 110r can include one or more reference light emitters and receivers located to send and receive a reference light to calibrate and/or otherwise detect one or more spatial aspects of the objects 12 such as location, position, orientation, visual placement, visual appearance, and/or conformation. The reference light based sensing component 110r can also include processing aspects to prepare sensed information for the status determination unit 106.

The acoustic reference based sensing component 110s can include one or more acoustic reference emitters and receivers located to send and receive an acoustic reference signal to calibrate and/or otherwise detect one or more spatial aspects of the objects 12 such as location, position, orientation, visual placement, visual appearance, and/or conformation. The acoustic reference based sensing component 110s can also include processing aspects to prepare sensed information for the status determination unit 106.

The triangulation based sensing component 110t can include one or more emitters and receivers located to send and receive signals to calibrate and/or otherwise detect using triangulation methods one or more spatial aspects of the objects 12 such as location, position, orientation, visual placement, visual appearance, and/or conformation. The triangulation based sensing component 110t can also include processing aspects to prepare sensed information for the status determination unit 106.

The status determination unit 106 is further shown in FIG. 6 to optionally include a control unit 160, a processor 162, a logic unit 164, a memory 166, a determination engine 167, a storage unit 168, an interface 169, and modules 170.

Figure 7:
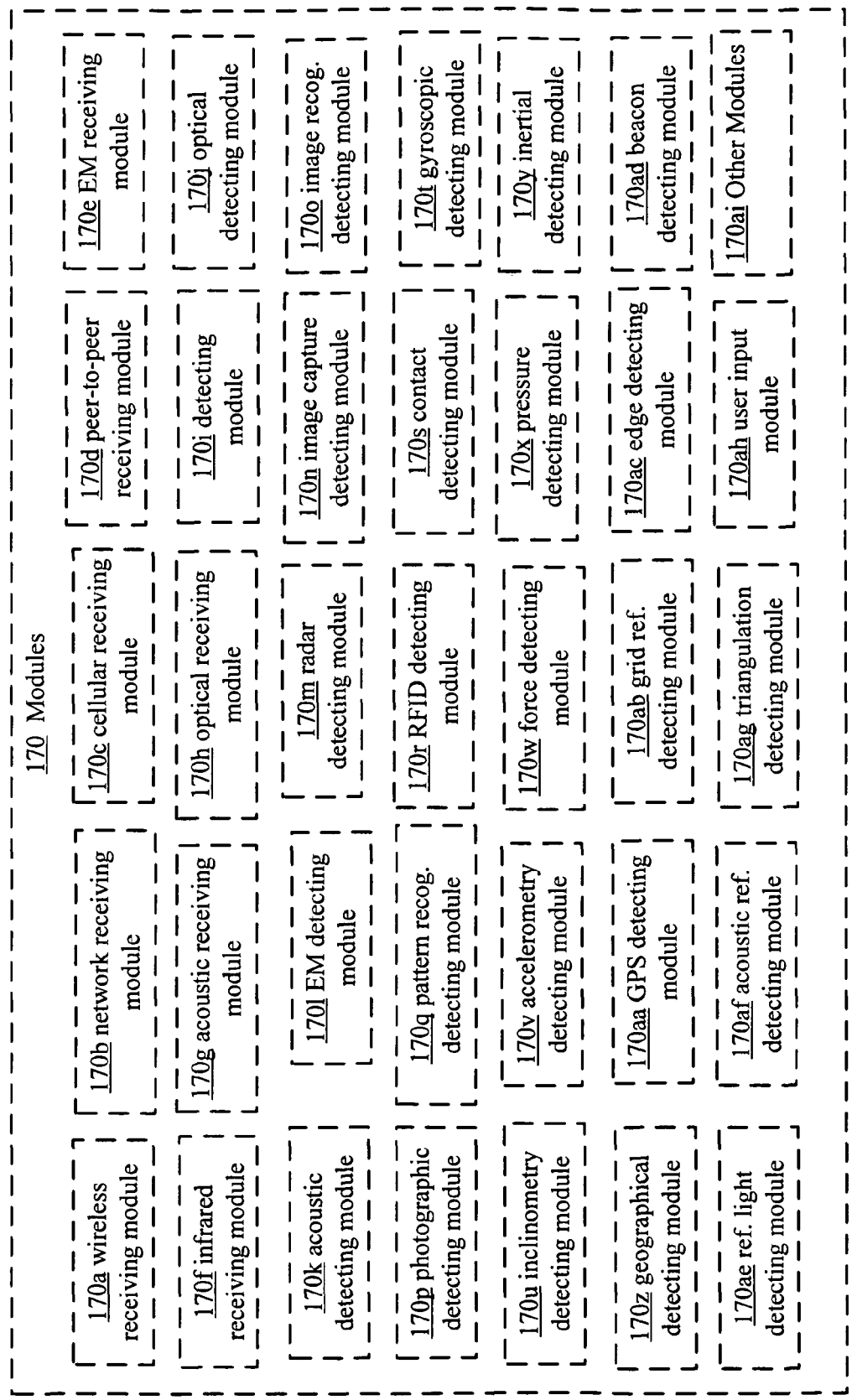
FIG. 7 is a block diagram of an exemplary implementation of modules for a status determination unit 106 of the status determination system 158 of FIG. 6.

The modules 170 is further shown in FIG. 7 to optionally include a wireless receiving module 170a, a network receiving module 170b, cellular receiving module 170c, a peer-to-peer receiving module 170d, an electromagnetic receiving module 170e, an infrared receiving module 170f, an acoustic receiving module 170g, an optical receiving module 170h, a detecting module 170i, an optical detecting module 170j, an acoustic detecting module 170k, an electromagnetic detecting module 170l, a radar detecting module 170m, an image capture detecting module 170n, an image recognition detecting module 170o, a photographic detecting module 170p, a pattern recognition detecting module 170q, a radiofrequency detecting module 170r, a contact detecting module 170s, a gyroscopic detecting module 170*t*, an inclinometry detecting module 170*u*, an accelerometry detecting module 170*v*, a force detecting module 170*w*, a pressure detecting module 170*x*, an inertial detecting module 170*y*, a geographical detecting module 170*z*, a global positioning system (GPS) detecting module 170*aa*, a grid reference detecting module 170*ab*, an edge detecting module 170*ac*, a beacon detecting module 170*ad*, a reference light detecting module 170*ae*, an acoustic reference detecting module 170*af*, a triangulation detecting module 170*ag*, a user input module 170*ah*, and an other modules 170*ai*.

Figure 8:
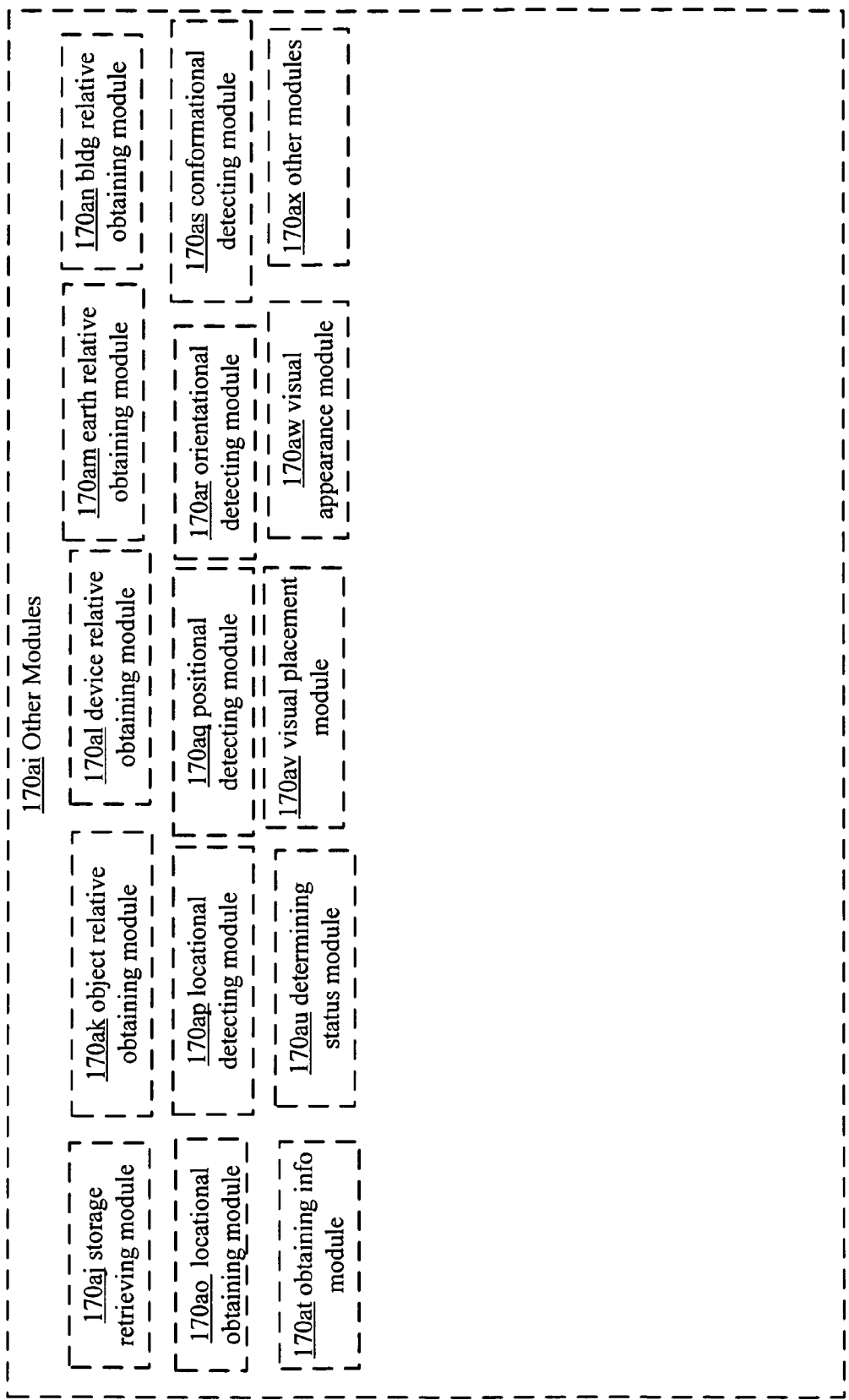
FIG. 8 is a block diagram of an exemplary implementation of modules for a status determination unit 106 of the status determination system 158 of FIG. 6.

The other modules 170*ai* is shown n FIG. 8 to further include a storage retrieving module 170*aj*, an object relative obtaining module 170*ak*, a device relative obtaining module 170*al*, an earth relative obtaining module 170*am*, a building relative obtaining module 170*an*, a locational obtaining module 170*ao*, a locational detecting module 170*ap*, a positional detecting module 170*aq*, an orientational detecting module 170*ar*, a conformational detecting module 170*as*, an obtaining information module 170*at*, a determining status module 170*au*, a visual placement module 170*av*, a visual appearance module 170*aw*, and an other modules 170*ax*.

Figure 9:
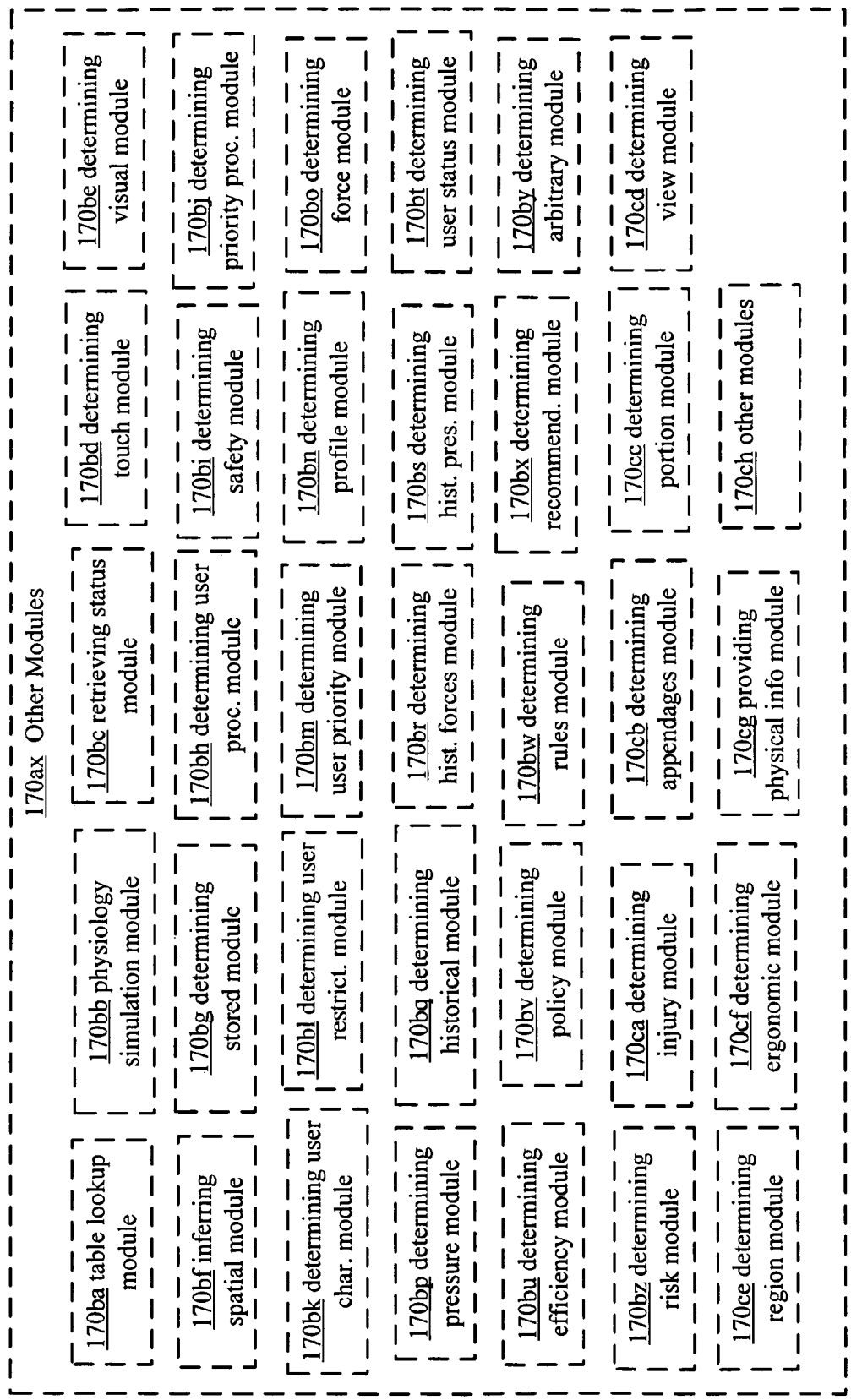
FIG. 9 is a block diagram of an exemplary implementation of modules for a status determination unit 106 of the status determination system 158 of FIG. 6.

The other modules 170*ax* is shown in FIG. 9 to further include a table lookup module 170*ba*, a physiology simulation module 170*bb*, a retrieving status module 170*bc*, a determining touch module 170*bd*, a determining visual module 170*ba*, an inferring spatial module 170*bf*, a determining stored module 170*bg*, a determining user procedure module 170*bh*, a determining safety module 170*bi*, a determining priority procedure module 170*bj*, a determining user characteristics module 170*bk*, a determining user restrictions module 170*bl*, a determining user priority module 170*bm*, a determining profile module 170*bn*, a determining force module 170*bo*, a determining pressure module 170*bp*, a determining historical module 170*bq*, a determining historical forces module 170*br*, a determining historical pressures module 170*bs*, a determining user status module 170*bt*, a determining efficiency module 170*bu*, a determining policy module 170*bv*, a determining rules module 170*bw*, a determining recommendation module 170*bx*, a determining arbitrary module 170*by*, a determining risk module 170*bz*, a determining injury module 170*ca*, a determining appendages module 170*cb*, a determining portion module 170*cc*, a determining view module 170*cd*, a determining region module 170*ce*, a determining ergonomic module 170*cf*, a providing physical information module 170*cg*, and an other modules 170*ch*.

Figure 10:
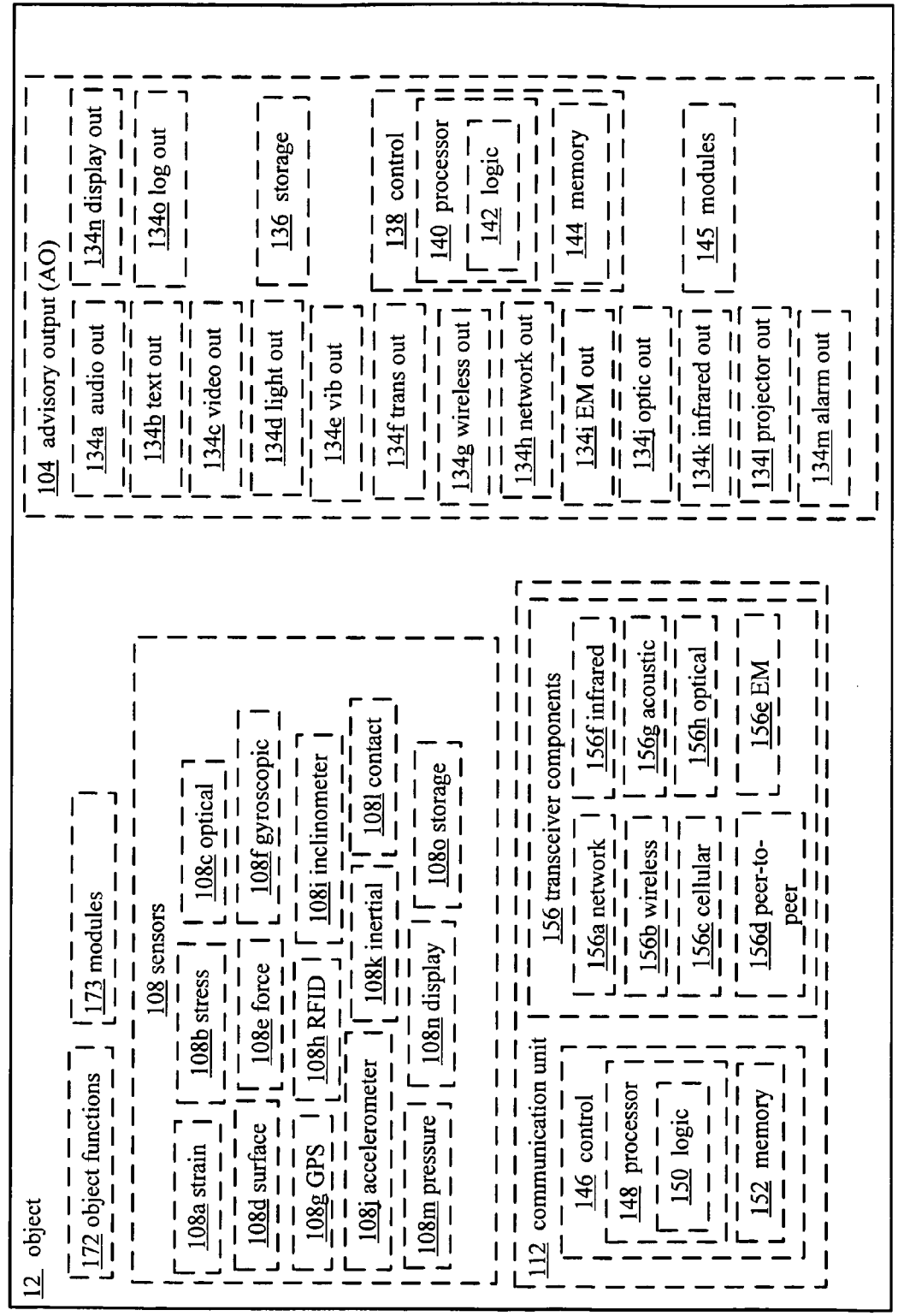
FIG. 10 is a block diagram of an exemplary implementation of an object forming a portion of an implementation of the general exemplary implementation of the postural information system of FIG. 1.

An exemplary version of the object 12 is shown in FIG. 10 to optionally include the advisory output 104, the communication unit 112, an exemplary version of the sensors 108, object functions 172, and modules 173. The sensors 108 optionally include a strain sensor 108*a*, a stress sensor 108*b*, an optical sensor 108*c*, a surface sensor 108*d*, a force sensor 108*e*, a gyroscopic sensor 108*f*, a GPS sensor 108*g*, an RFID sensor 108*h*, a inclinometer sensor 108*i*, an accelerometer sensor 108*j*, an inertial sensor 1/08*k*, a contact sensor 108*l*, a pressure sensor 108*m*, a display sensor 108*n*, and storage 108*o*.

Figure 11:
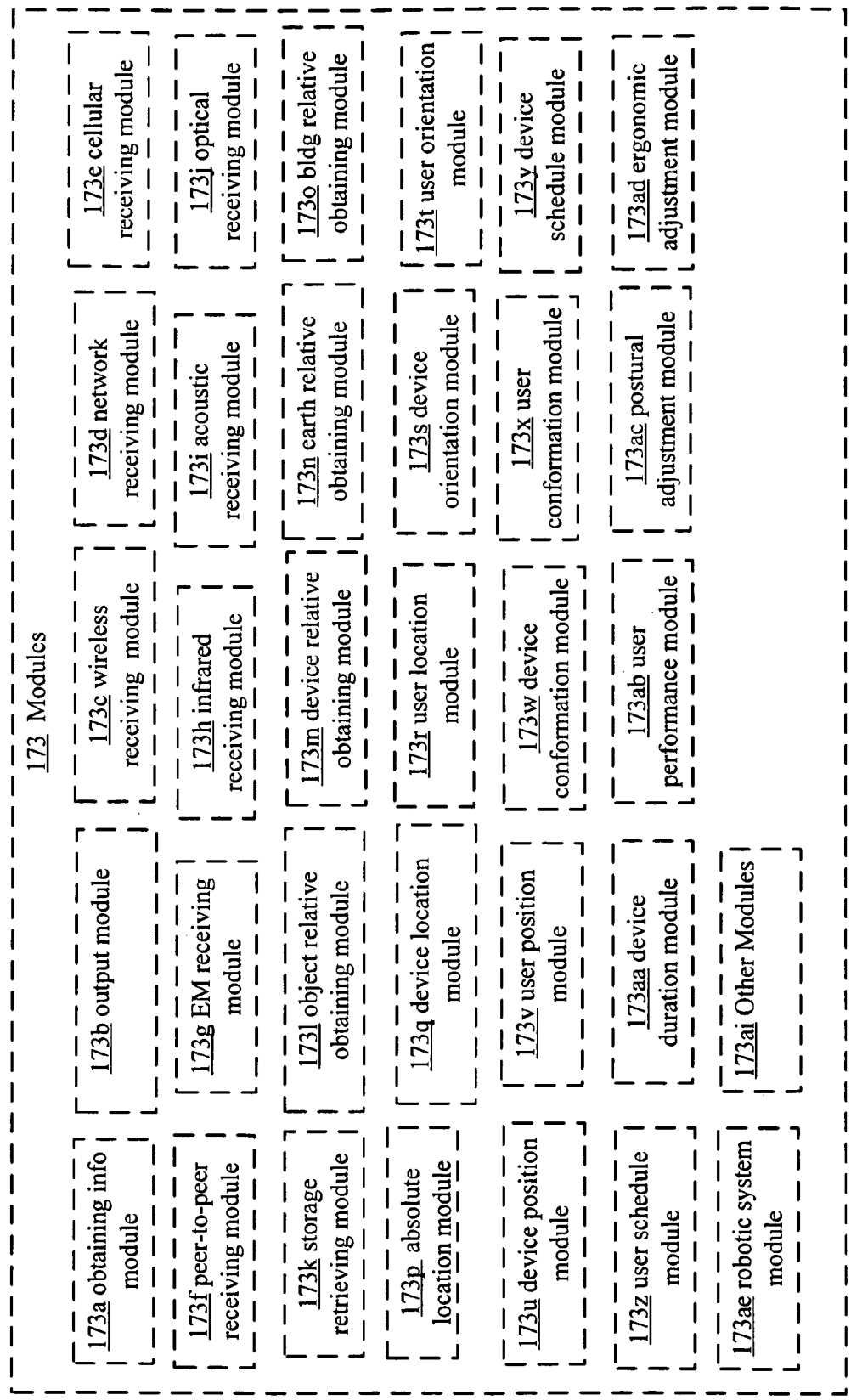
FIG. 11 is a block diagram of an exemplary implementation of modules for the object 12 of FIG. 10.

The modules 173 is shown in FIG. 11 to include an obtaining information module 173*a*, an output module 173*b*, a wireless receiving module 173*c*, a network receiving module 173*d*, a cellular receiving module 173*e*, a peer-to-peer receiving module 173*f*, an EM receiving module 173*g*, an infrared receiving module 173*h*, an acoustic receiving module 173*i*, an optical receiving module 173*j*, a storage retrieving module 173*k*, an object relative obtaining module 173*l*, a device relative obtaining module 173*m*, an earth relative obtaining module 173*n*, a building relative obtaining module 173*o*, an absolute location module 173*p*, a device location module 173*q*, a user location module 173*r*, a device orientation module 173*s*, a user orientation module 173*t*, a device position module 173*u*, a user position module 173*v*, a device conformation module 173*w*, a user conformation module 173*x*, a device schedule module 173*y*, a user schedule module 173*z*, a device duration module 173*aa*, a user performance module 173*ab*, a postural adjustment module 173*ac*, an ergonomic adjustment module 173*ad*, a robotic system module 173*ae*, and other modules 173*ai*.

Figure 12:
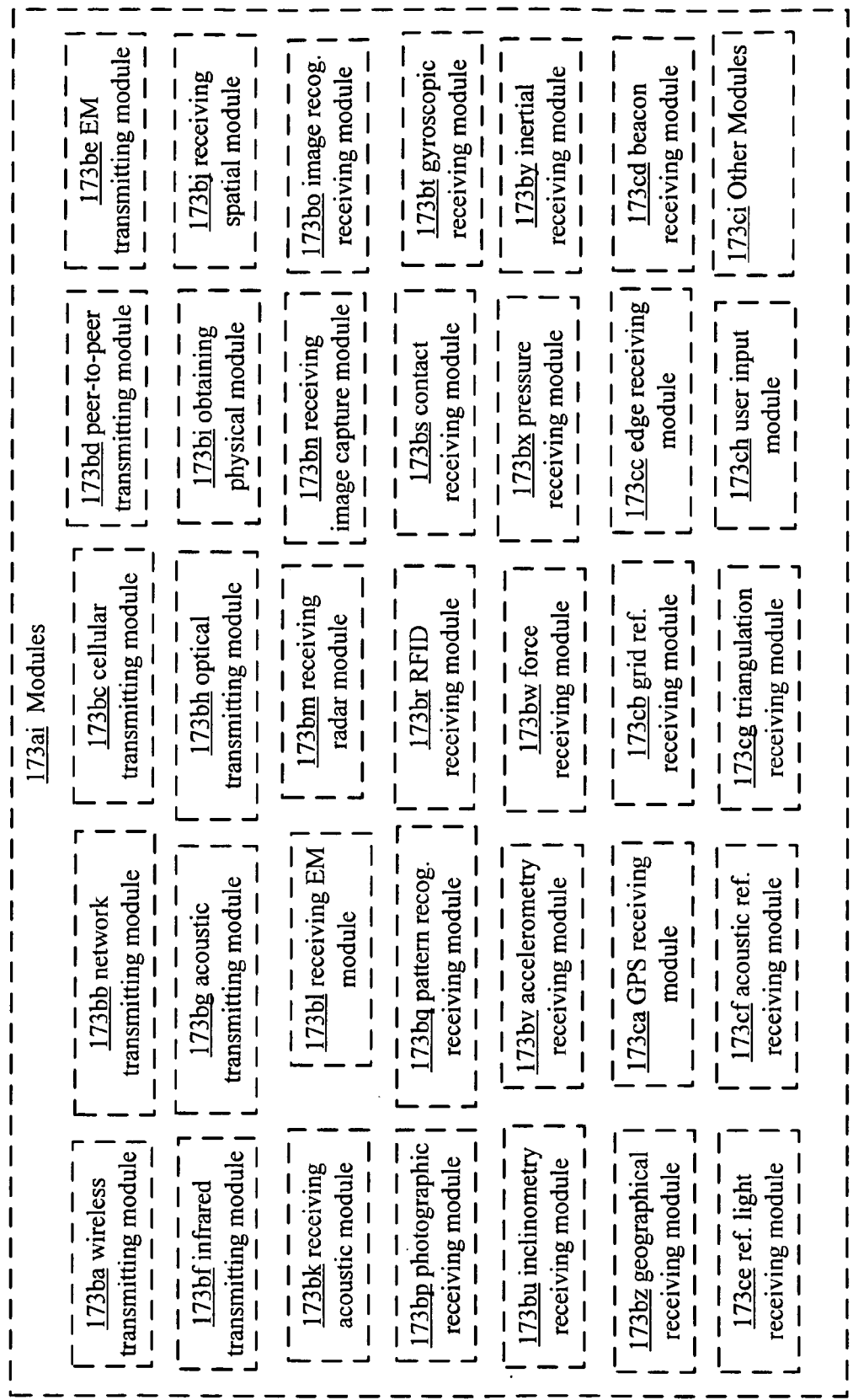
FIG. 12 is a block diagram of an exemplary implementation of modules for the object 12 of FIG. 10.

The other modules 173*ai* is shown in FIG. 12 to include a wireless transmitting module 173*ba*, a network transmitting module 173*bb*, a cellular transmitting module 173*bc*, a peer-to-peer transmitting module 173*bd*, an EM transmitting module 173*be*, an infrared transmitting module 173*bf*, an acoustic transmitting module 173*bg*, an optical transmitting module 173*bh*, an obtaining physical module 173*bi*, a receiving spatial module 173*bj*, a receiving acoustic module 173*bk*, a receiving EM module 173*bl*, a receiving radar module 173*bm*, a receiving image capture module 173*bn*, an image recognition receiving module 173*bo*, a photographic receiving module 173*bp*, a pattern recognition receiving module 173*bq*, an RFID receiving module 173*br*, a contact receiving module 173*bs*, a gyroscopic receiving module 173*bt*, an inclinometry receiving module 173*bu*, a accelerometry receiving module 173*bv*, a force receiving module 173*bw*, a pressure receiving module 173*bx*, an inertial receiving module 173*by*, a geographical receiving module 173*bz*, a GPS receiving module 173*ca*, a grid reference receiving module 173*cb*, an edge receiving module 173*cc*, a beacon receiving module 173*cd*, a reference light receiving module 173*ce*, an acoustic reference receiving module 173*cf*, a triangulation receiving module 173*cg*, a user input module 173*ch*, and other modules 173*ci*.

Figure 13:
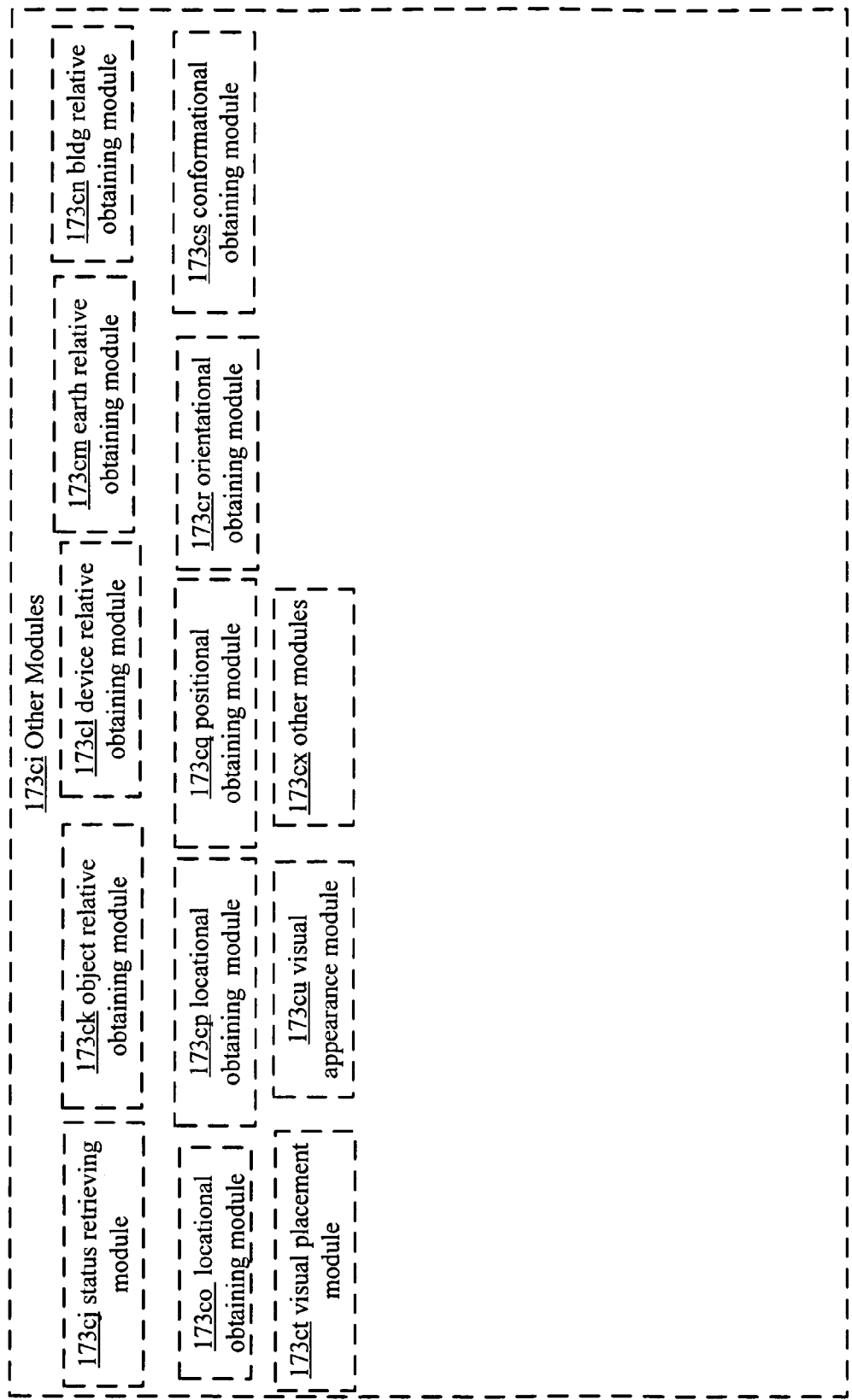
FIG. 13 is a block diagram of an exemplary implementation of modules for the object 12 of FIG. 10.

The other modules 173*ci* is shown in FIG. 13 to include a status retrieving module 173*cj*, an object relative obtaining module 173*ck*, a device relative obtaining module 173*cl*, an earth relative obtaining module 173*cm*, a building relative obtaining module 173*cn*, a locational obtaining module 173*co*, a locational obtaining module 173*cp*, a positional obtaining module 173*cq*, an orientational obtaining module 173*cr*, a conformational obtaining module 173*cs*, a visual placement module 173*ct*, a visual appearance module 173*cu*, and other modules 173*cx*.

Figure 14:
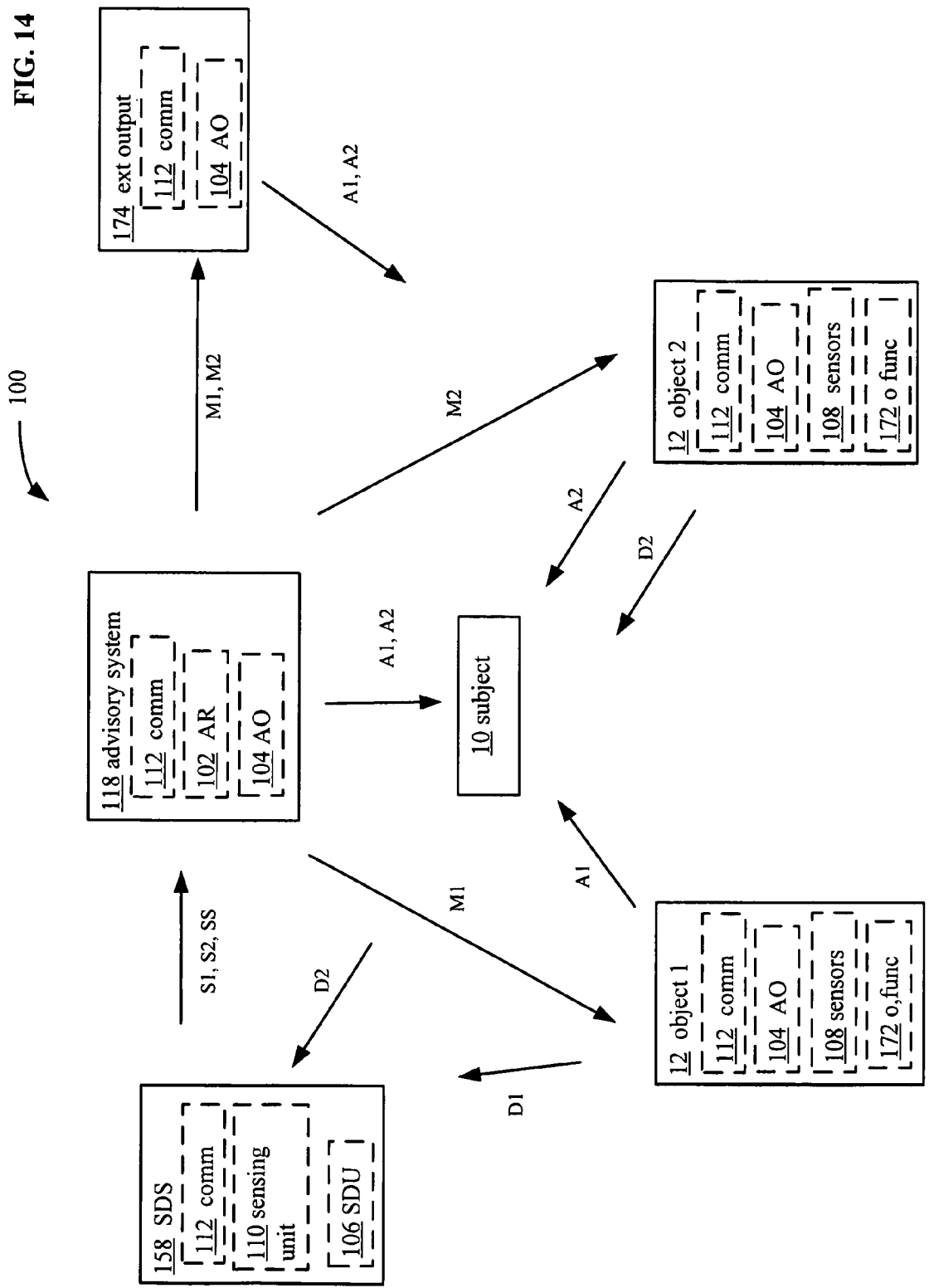
FIG. 14 is a block diagram of a second exemplary implementation of the general exemplary implementation of the postural information system of FIG. 1.

An exemplary configuration of the system 100 is shown in FIG. 14 to include an exemplary versions of the status determination system 158, the advisory system 118, and with two instances of the object 12. The two instances of the object 12 are depicted as "object 1" and "object 2," respectively. The exemplary configuration is shown to also include an external output 174 that includes the communication unit 112 and the advisory output 104.

As shown in FIG. 14, the status determination system 158 can receive physical status information D1 and D2 as acquired by the sensors 108 of the objects 12, namely, object 1 and object 2, respectively. The physical status information D1 and D2 are acquired by one or more of the sensors 108 of the respective one of the objects 12 and sent to the status determination system 158 by the respective one of the communication unit 112 of the objects. Once the status determination system 158 receives the physical status information D1 and D2, the status determination unit 106, better shown in FIG. 6, uses the control unit 160 to direct determination of status of the objects 12 and the subject 10 through a combined use of the determination engine 167, the storage unit 168, the interface 169, and the modules 170 depending upon the circumstances involved. Status of the subject 10 and the objects 12 can include their spatial status including positional, locational, orientational, and conformational status. In particular, physical status of the subject 10 is of interest since advisories can be subsequently generated to adjust such physical status. Advisories can contain information to also guide adjustment of physical status of the objects 12, such as location, since this can influence the physical status of the subject 10, such as through requiring the subject to view or touch the objects.

Continuing on with FIG. 14, alternatively or in conjunction with receiving the physical status information D1 and D2 from the objects 12, the status determination system 158 can use the sensing unit 110 to acquire information regarding physical status of the objects without necessarily requiring use of the sensors 108 found with the objects. The physical status information acquired by the sensing unit 110 can be sent to the status determination unit 106 through the communication unit 112 for subsequent determination of physical status of the subject 10 and the objects 12.

For the configuration depicted in FIG. 14, once determined, the physical status information SS of the subject 10 as a user of the objects 12 and the physical status information S1 for the object 1 and the physical status information S2 for the object 2 is sent by the communication unit 112 of the status determination system 158 to the communication unit 112 of the advisory system 118. The advisory system 118 then uses this physical status information in conjunction with information and/or algorithms and/or other information processing of the advisory resource unit 102 to generate advisory based content to be included in messages labeled M1 and M2 to be sent to the communication units of the objects 12 to be used by the advisory outputs 104 found in the objects, to the communication units of the external output 174 to be used by the advisory output found in the external output, and/or to be used by the advisory output internal to the advisory system.

If the advisory output 104 of the object 12 (1) is used, it will send an advisory (labeled as A1) to the subject 10 in one or more physical forms (such as light, audio, video, vibration, electromagnetic, textual and/or another indicator or media) directly to the subject or to be observed indirectly by the subject. If the advisory output 104 of the object 12 (2) is used, it will send an advisory (labeled as A2) to the subject 10 in one or more physical forms (such as light, audio, video, vibration, electromagnetic, textual and/or another indicator or media) directly to the subject or to be observed indirectly by the subject. If the advisory output 104 of the external output 174 is used, it will send advisories (labeled as A1 and A2) in one or more physical forms (such as light, audio, video, vibration, electromagnetic, textual and/or another indicator or media) directly to the subject 10 or to be observed indirectly by the subject. If the advisory output 104 of the advisory system 118 is used, it will send advisories (labeled as A1 and A2) in one or more physical forms (such as light, audio, video, vibration, electromagnetic, textual and/or another indicator or media) directly to the subject 10 or to be observed indirectly by the subject. As discussed, an exemplary intent of the advisories is to inform the subject 10 of an alternative configuration for the objects 12 that would allow, encourage, or otherwise support a change in the physical status, such as the posture, of the subject.

Figure 15:
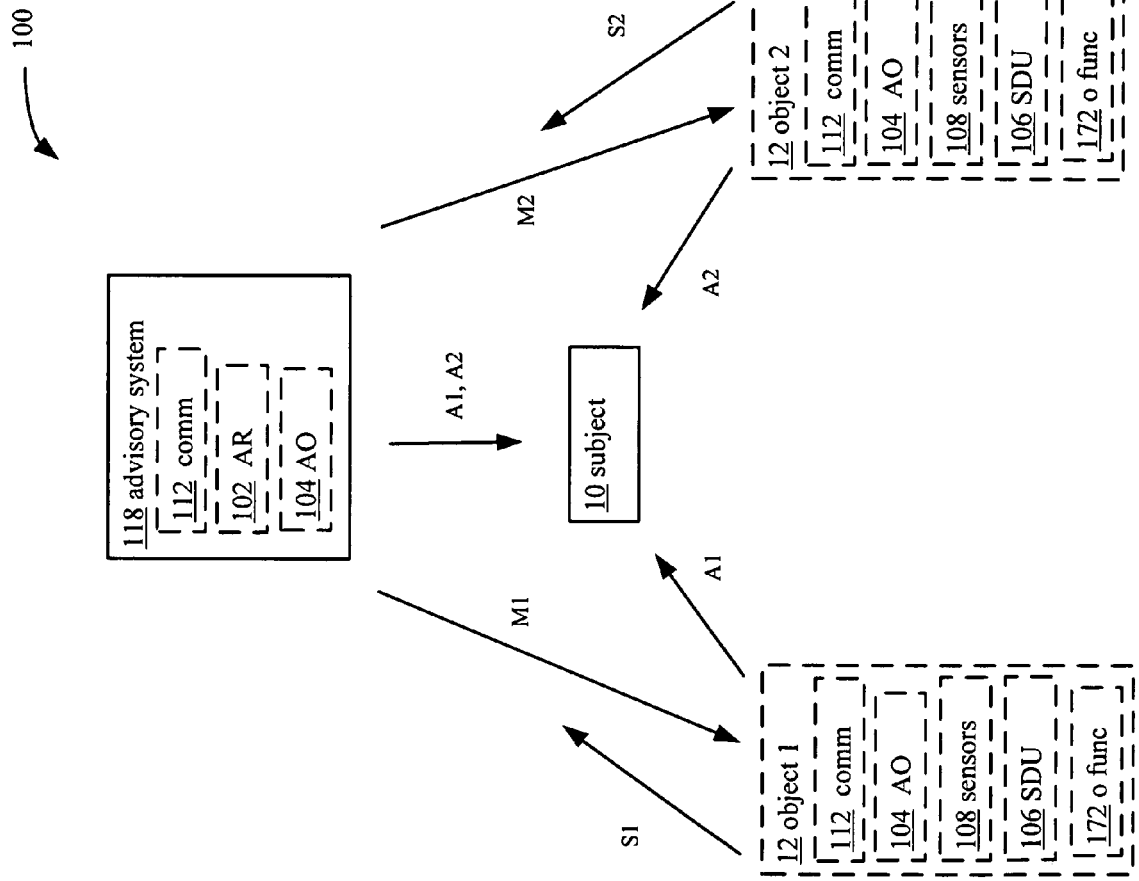
FIG. 15 is a block diagram of a third exemplary implementation of the general exemplary implementation of the postural information system of FIG. 1.

An exemplary alternative configuration for the system 100 is shown in FIG. 15 to include an advisory system 118 and versions of the objects 12 that include the status determination unit 106. Each of the objects 12 are consequently able to determine their physical status through use of the status determination unit from information collected by the one or more sensors 108 found in each of the objects. The physical status information is shown being sent from the objects 12 (labeled as S1 and S2 for that being sent from the object 1 and object 2, respectively) to the advisory system 118. In implementations of the advisory system 118 where an explicit physical status of the subject 10 is not received, the advisory system can infer the physical status of the subject 10 from the physical status received of the objects 12. Instances of the advisory output 104 are found in the advisory system 118 and/or the objects 12 so that the advisories A1 and A2 are sent from the advisory system and/or the objects to the subject 10.

Figure 16:
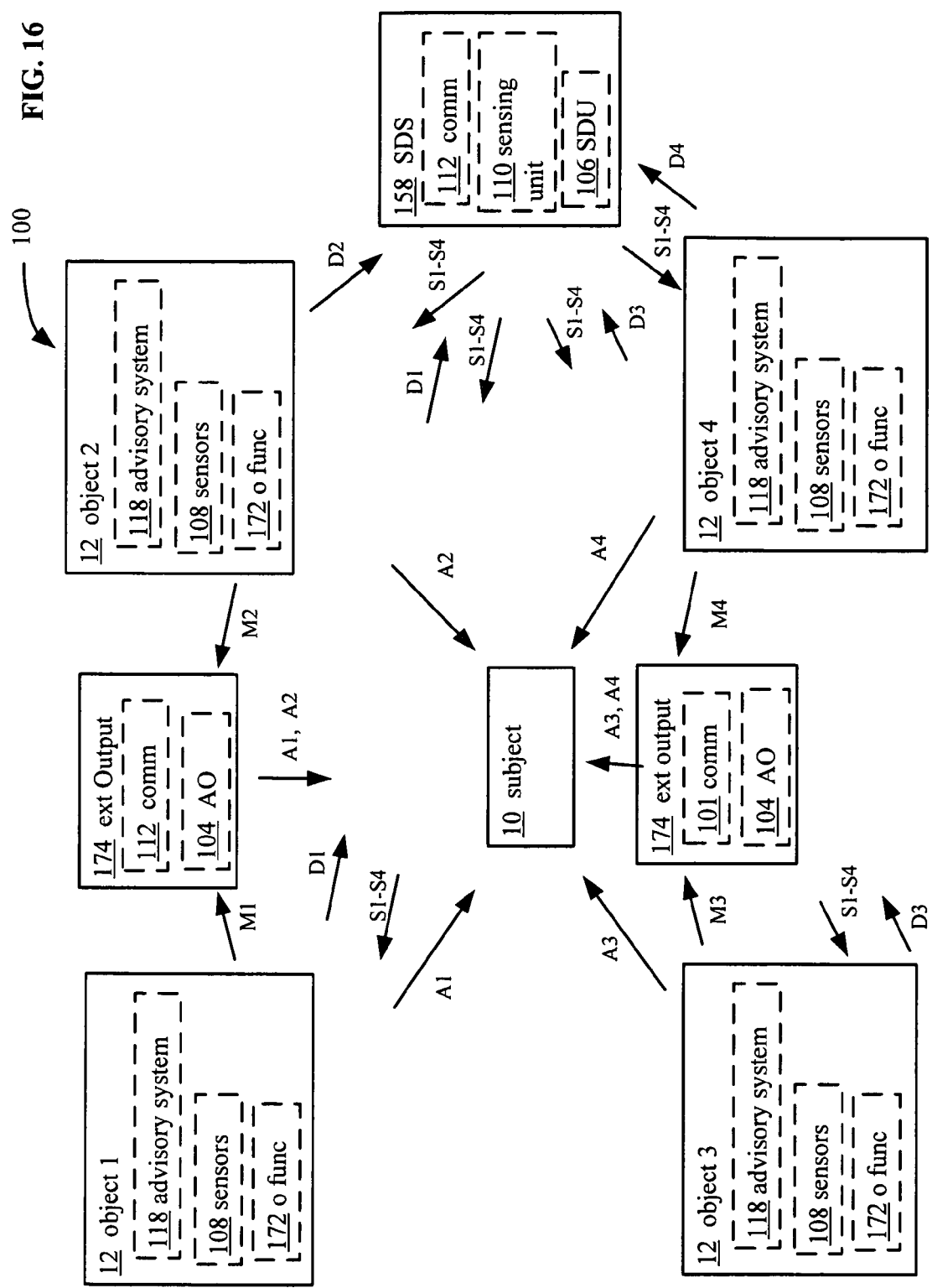
FIG. 16 is a block diagram of a fourth exemplary implementation of the general exemplary implementation of the postural information system of FIG. 1.

An exemplary alternative configuration for the system 100 is shown in FIG. 16 to include the status determination system 158, two instances of the external output 174, and four instances of the objects 12, which include the advisory system 118. With this configuration, some implementations of the objects 12 can send physical status information D1-D4 as acquired by the sensors 108 found in the objects 12 to the status determination system 158. Alternatively, or in conjunction with the sensors 108 on the objects 12, the sensing unit 110 of the status determination system 158 can acquire information regarding physical status of the objects 12.

Based upon the acquired information of the physical status of the objects 12, the status determination system 158 determines physical status information S1-S4 of the objects 12 (S1-S4 for object 1-object 4, respectively). In some alternatives, all of the physical status information S1-S4 is sent by the status determination system 158 to each of the objects 12 whereas in other implementations different portions are sent to different objects. The advisory system 118 of each of the objects 12 uses the received physical status to determine and to send advisory information either to its respective advisory output 104 or to one of the external outputs 174 as messages M1-M4. In some implementations, the advisory system 118 will infer physical status for the subject 10 based upon the received physical status for the objects 12. Upon receipt of the messages M1-M4, each of the advisory outputs 104 transmits a respective one of the messages M1-M4 to the subject 10.

Figure 17:
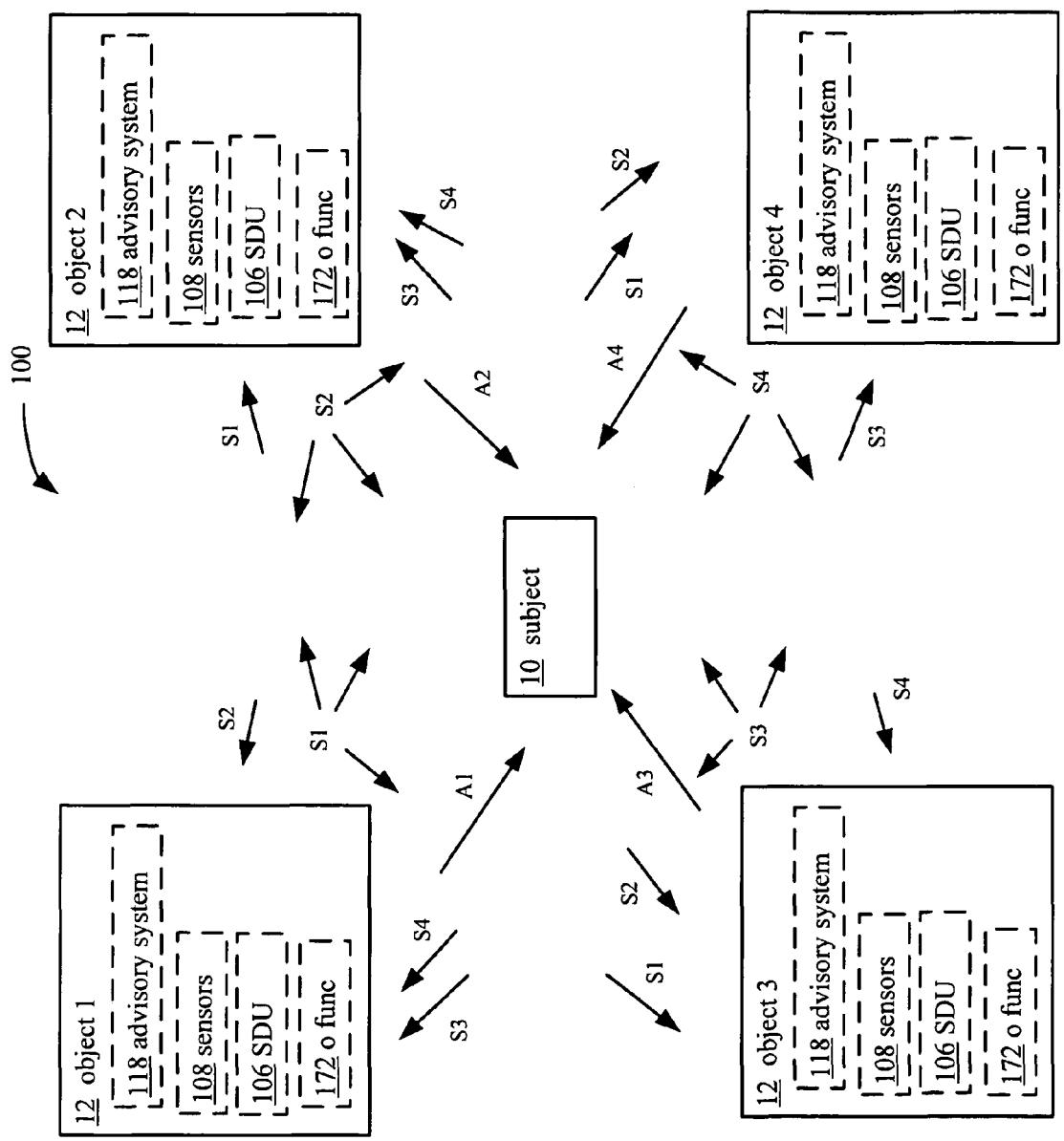
FIG. 17 is a block diagram of a fifth exemplary implementation of the general exemplary implementation of the postural information system of FIG. 1.

An exemplary alternative configuration for the system 100 is shown in FIG. 17 to include four of the objects 12. Each of the objects 12 includes the status determination unit 106, the sensors 108, and the advisory system 118. Each of the objects 12 obtains physical status information through its instance of the sensors 108 to be used by its instance of the status determination unit 106 to determine physical status of the object. Once determined, the physical status information (S1-S4) of each of the objects 12 is shared with all of the objects 12, but in other implementations need not be shared with all of the objects. The advisory system 118 of each of the objects 12 uses the physical status determined by the status determination unit 106 of the object and the physical status received by the object to generate and to send an advisory (A1-A4) from the object to the subject 10.

The various components of the system 100 with implementations including the advisory resource unit 102, the advisory output 104, the status determination unit 106, the sensors 108, the sensing unit 110, and the communication unit 112 and their sub-components and the other exemplary entities depicted may be embodied by hardware, software and/or firmware. For example, in some implementations the system 100 including the advisory resource unit 102, the advisory output 104, the status determination unit 106, the sensors 108, the sensing unit 110, and the communication unit 112 may be implemented with a processor (e.g., microprocessor, controller, and so forth) executing computer readable instructions (e.g., computer program product) stored in a storage medium (e.g., volatile or non-volatile memory) such as a signal-bearing medium. Alternatively, hardware such as application specific integrated circuit (ASIC) may be employed in order to implement such modules in some alternative implementations.

Figure 18:
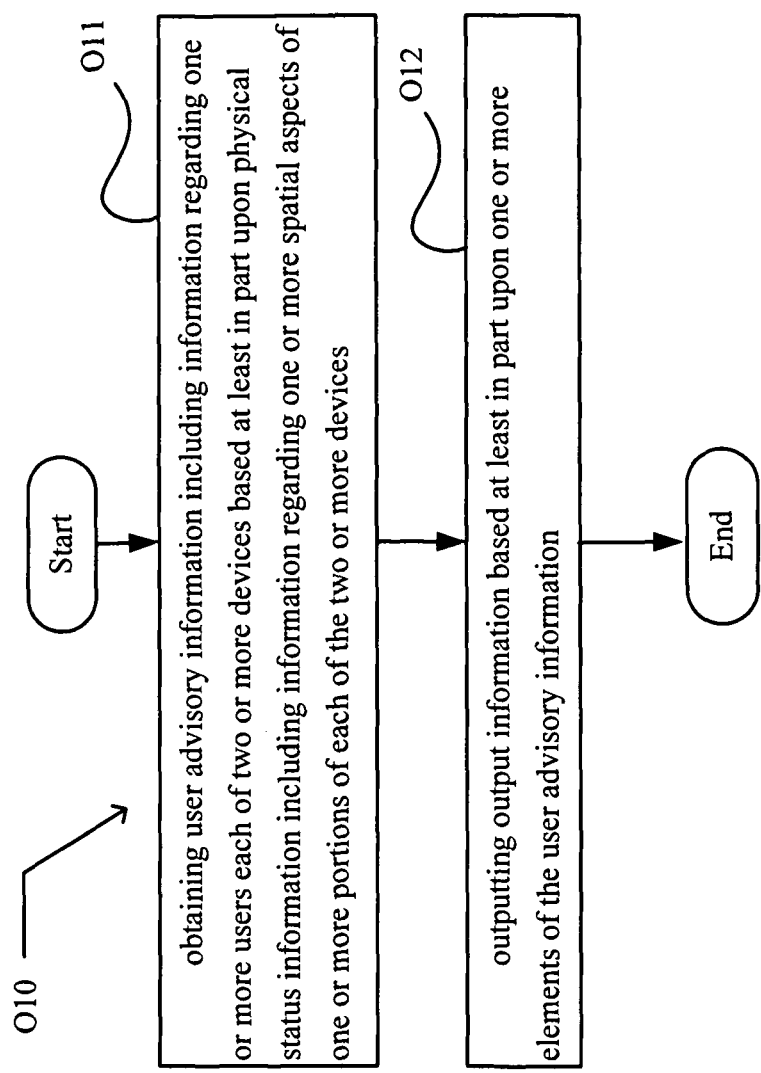
FIG. 18 is a high-level flowchart illustrating an operational flow O10 representing exemplary operations related to obtaining user advisory information including information regarding one or more users each of two or more devices based at least in part upon physical status information including information regarding one or more spatial aspects of one or more portions of each of the two or more devices, and outputting output information based at least in part upon one or more elements of the user advisory information at least associated with the depicted exemplary implementations of the postural information system.

An operational flow O10 as shown in FIG. 18 represents example operations related to obtaining physical status information, determining user status information, and determining user advisory information. In cases where the operational flows involve users and devices, as discussed above, in some implementations, the objects 12 can be devices and the subjects 10 can be users of the devices. FIG. 18 and those figures that follow may have various examples of operational flows, and explanation may be provided with respect to the above-described examples of FIGS. 1-17 and/or with respect to other examples and contexts. Nonetheless, it should be understood that the operational flows may be executed in a number of other environments and contexts, and/or in modified versions of FIGS. 1-17. Furthermore, although the various operational flows are presented in the sequence(s) illustrated, it should be understood that the various operations may be performed in other orders than those which are illustrated, or may be performed concurrently.

FIG. 18

In FIG. 18 and those figures that follow, various operations may be depicted in a box-within-a-box manner. Such depictions may indicate that an operation in an internal box may comprise an optional exemplary implementation of the operational step illustrated in one or more external boxes. However, it should be understood that internal box operations may be viewed as independent operations separate from any associated external boxes and may be performed in any sequence with respect to all other illustrated operations, or may be performed concurrently.

After a start operation, the operational flow O10 may move to an operation O11, where obtaining user advisory information including information regarding one or more users each of two or more devices based at least in part upon physical status information including information regarding one or more spatial aspects of one or more portions of each of the two or more devices may be, executed by, for example, the obtaining information module 173a of FIG. 11 directing the communication unit 112 of the object 12 of FIG. 10 to receive through one or more of the transceiver components 156 user advisory information (e.g. including M1 and M2 as depicted in FIG. 14 and in FIG. 15) from the advisory system 118 of FIG. 3. In implementations the user advisory information can include information regarding one or more users each of two or more devices based at least in part upon physical status information including information regarding one or more spatial aspects of one or more portions of each of the two or more devices (e.g. S1 and S2 depicted as being sent from the objects 12 in FIG. 15).

The operational flow O10 may then move to operation O12, where outputting output information based at least in part upon one or more elements of the user advisory information may be executed by, the advisory output 104 of FIG. 1. An exemplary implementation may include the output module 173b of FIG. 11 directing the advisory output 104 to receive information containing advisory based content from the advisory system 118 either externally (such as "M" depicted in FIG. 14) and internally (such as from the advisory resource 102 to the advisory output within the advisory system, for instance, shown in FIG. 14). After receiving the information containing advisory based content, the output module 173b of FIG. 11 can direct the advisory output 104 to output information (e.g. A1 and A2 of FIG. 14 and FIG. 15) based at least in part upon one or more elements of the user advisory information.

FIG. 19

Figure 19:
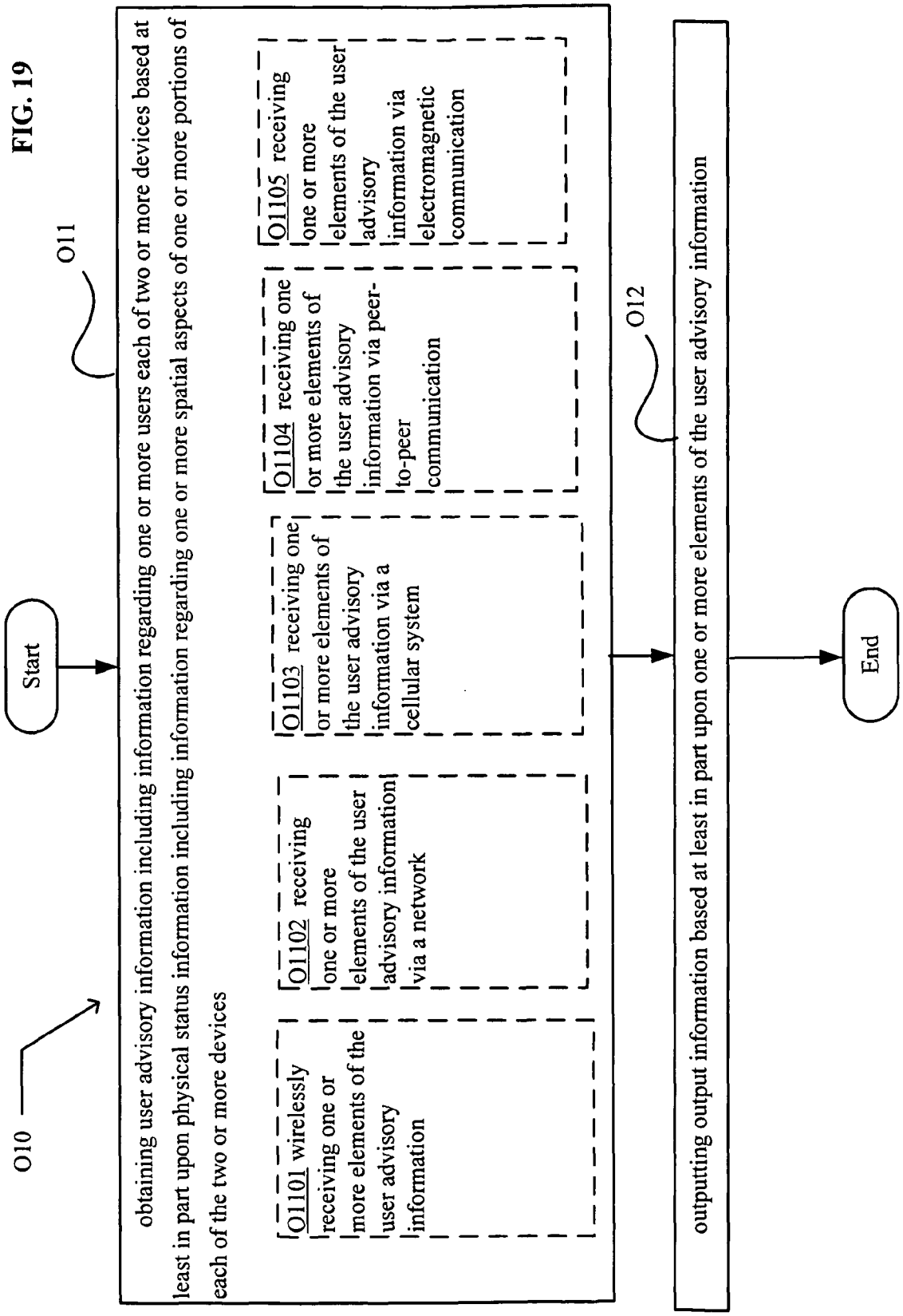
FIG. 19 is a high-level flowchart including exemplary implementations of operation O11 of FIG. 18.

FIG. 19 illustrates various implementations of the exemplary operation O11 of FIG. 18. In particular, FIG. 19 illustrates example implementations where the operation O11 includes one or more additional operations including, for example, operations O1101, O1102, O1103, O1104, and/or O1105, which may be executed generally by, in some instances, one or more of the transceiver components 156 of the communication unit 112 of the status determining system 158 of FIG. 6.

For instance, in some implementations, the exemplary operation O11 may include the operation of O1101 for wirelessly receiving one or more elements of the user advisory information. An exemplary implementation may include the wireless receiving module 173c of FIG. 11 directing one or more of the wireless transceiver components 156b of the communication unit 112 of the object 12 of FIG. 10 to receive one or more elements of the user advisory information (e.g. including M1 and M2 as depicted in FIG. 14 and in FIG. 15) from the wireless transceiver components 156b of the advisory system 118 of FIG. 3. In implementations the one or more elements of the user advisory information can include information regarding one or more users each of two or more devices based at least in part upon physical status information including information regarding one or more spatial aspects of one or more portions of each of the two or more devices (e.g. S1 and S2 depicted as being sent from the objects 12 in FIG. 15).

For instance, in some implementations, the exemplary operation O11 may include the operation of O1102 for receiving one or more elements of the user advisory information via a network. An exemplary implementation may include the network receiving module 173d of FIG. 11 directing one or more of the network transceiver components 156a of the communication unit 112 of the object 12 of FIG. 10 to receive one or more elements of the user advisory information (e.g. including M1 and M2 as depicted in FIG. 14 and in FIG. 15) from the network transceiver components 156a of the advisory system 118 of FIG. 3. In implementations the one or more elements of the user advisory information can include information regarding one or more users each of two or more devices based at least in part upon physical status information including information regarding one or more spatial aspects of one or more portions of each of the two or more devices (e.g. S1 and S2 depicted as being sent from the objects 12 in FIG. 15).

For instance, in some implementations, the exemplary operation O11 may include the operation of O1103 for receiving one or more elements of the user advisory information via a cellular system. An exemplary implementation may include the cellular receiving module 173e of FIG. 11 directing one or more of the cellular transceiver components 156c of the communication unit 112 of the object 12 of FIG. 10 to receive one or more elements of the user advisory information (e.g. including M1 and M2 as depicted in FIG. 14 and in FIG. 15) from the cellular transceiver components 156c of the advisory system 118 of FIG. 3. In implementations the one or more elements of the user advisory information can include information regarding one or more users each of two or more devices based at least in part upon physical status information including information regarding one or more spatial aspects of one or more portions of each of the two or more devices (e.g. S1 and S2 depicted as being sent from the objects 12 in FIG. 15).

For instance, in some implementations, the exemplary operation O11 may include the operation of O1104 for receiving one or more elements of the user advisory information via peer-to-peer communication. An exemplary implementation may include the peer-to-peer receiving module 173f of FIG. 11 directing one or more of the peer-to-peer transceiver components 156d of the communication unit 112 of the object 12 of FIG. 10 to receive one or more elements of the user advisory information (e.g. including M1 and M2 as depicted in FIG. 14 and in FIG. 15) from the peer-to-peer transceiver components 156d of the advisory system 118 of FIG. 3. In implementations the one or more elements of the user advisory information can include information regarding one or more users each of two or more devices based at least in part upon physical status information including information regarding one or more spatial aspects of one or more portions of each of the two or more devices (e.g. S1 and S2 depicted as being sent from the objects 12 in FIG. 15).

For instance, in some implementations, the exemplary operation O11 may include the operation of O1105 for receiving one or more elements of the user advisory information via electromagnetic communication. An exemplary implementation may include the EM receiving module 173g of FIG. 11 directing one or more of the electromagnetic communication transceiver components 156e of the communication unit 112 of the object 12 of FIG. 10 to receive one or more elements of the user advisory information (e.g. including M1 and M2 as depicted in FIG. 14 and in FIG. 15) from the electromagnetic communication transceiver components 156e of the advisory system 118 of FIG. 3. In implementations the one or more elements of the user advisory information can include information regarding one or more users each of two or more devices based at least in part upon physical status information including information regarding one or more spatial aspects of one or more portions of each of the two or more devices (e.g. S1 and S2 depicted as being sent from the objects 12 in FIG. 15).

FIG. 20

Figure 20:
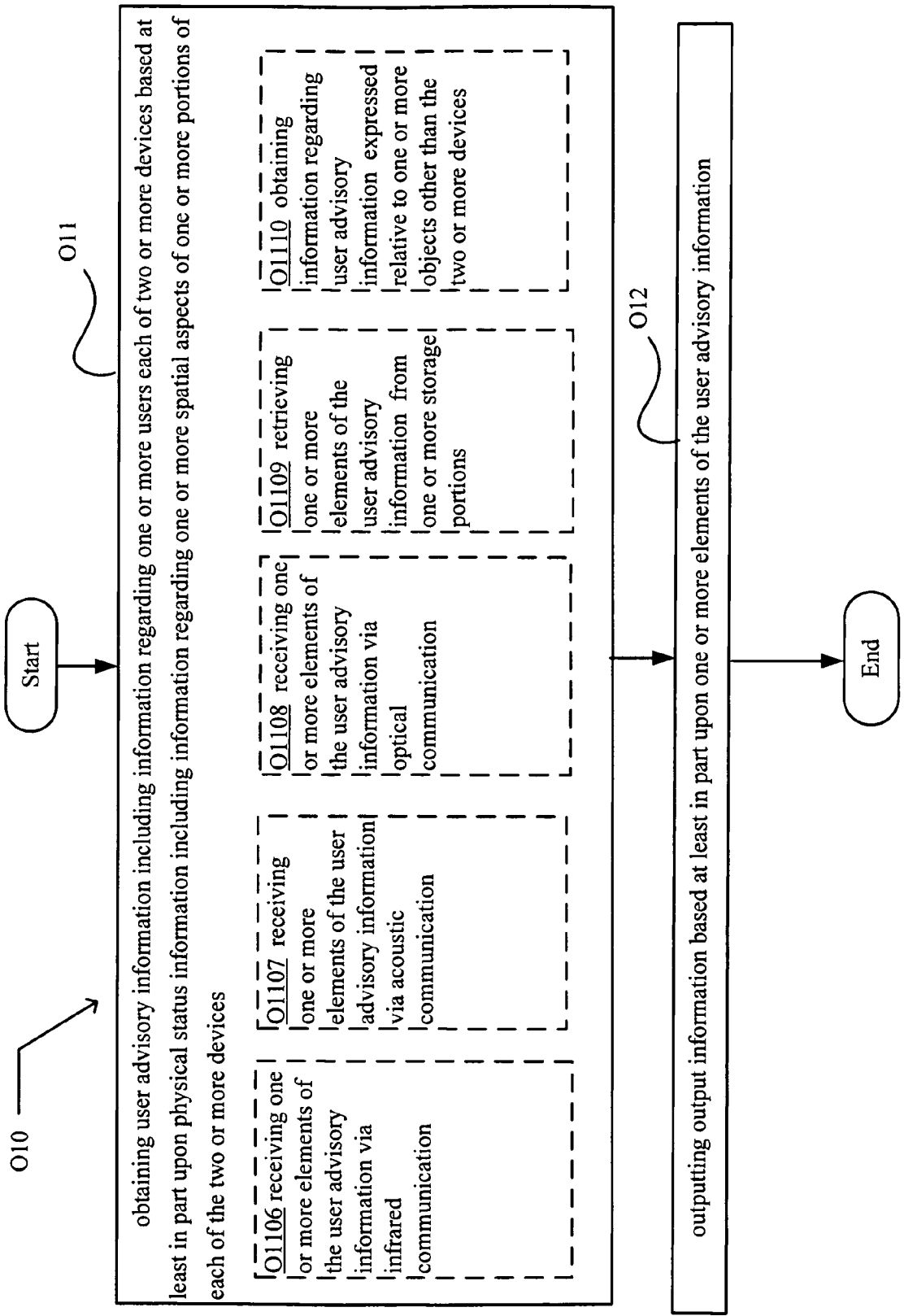
FIG. 20 is a high-level flowchart including exemplary implementations of operation O11 of FIG. 18.

FIG. 20 illustrates various implementations of the exemplary operation O11 of FIG. 20. In particular, FIG. 20 illustrates example implementations where the operation O11 includes one or more additional operations including, for example, operations O1106, O1107, O1108, O1109, and/or O1110, which may be executed generally by, in some instances, one or more of the transceiver components 156 of the communication unit 112 or one or more sensing components of the sensing unit 110 of the status determination system 158 of FIG. 6.

For instance, in some implementations, the exemplary operation O11 may include the operation of O1106 for receiving one or more elements of the user advisory information via infrared communication. An exemplary implementation may include the infrared receiving module 173h of FIG. 11 directing one or more of the infrared transceiver components 156f of the communication unit 112 of the object 12 of FIG. 10 to receive one or more elements of the user advisory information (e.g. including M1 and M2 as depicted in FIG. 14 and in FIG. 15) from the infrared transceiver components 156f of the advisory system 118 of FIG. 3. In implementations the one or more elements of the user advisory information can include information regarding one or more users each of two or more devices based at least in part upon physical status information including information regarding one or more spatial aspects of one or more portions of each of the two or more devices (e.g. S1 and S2 depicted as being sent from the objects 12 in FIG. 15).

For instance, in some implementations, the exemplary operation O11 may include the operation of O1107 for receiving one or more elements of the user advisory information via acoustic communication. An exemplary implementation may include the acoustic receiving module 173i of FIG. 11 directing one or more of the acoustic transceiver components 156g of the communication unit 112 of the object 12 of FIG. 10 to receive one or more elements of the user advisory information (e.g. including M1 and M2 as depicted in FIG. 14 and in FIG. 15) from the acoustic transceiver components 156g of the advisory system 118 of FIG. 3. In implementations the one or more elements of the user advisory information can include information regarding one or more users each of two or more devices based at least in part upon physical status information including information regarding one or more spatial aspects of one or more portions of each of the two or more devices (e.g. S1 and S2 depicted as being sent from the objects 12 in FIG. 15).

For instance, in some implementations, the exemplary operation O11 may include the operation of O1108 for receiving one or more elements of the user advisory information via optical communication. An exemplary implementation may include the optical receiving module 173j of FIG. 11 directing one or more of the optical transceiver components 156h of the communication unit 112 of the object 12 of FIG. 10 to receive one or more elements of the user advisory information (e.g. including M1 and M2 as depicted in FIG. 14 and in FIG. 15) from the optical transceiver components 156h of the advisory system 118 of FIG. 3. In implementations the one or more elements of the user advisory information can include information regarding one or more users each of two or more devices based at least in part upon physical status information including information regarding one or more spatial aspects of one or more portions of each of the two or more devices (e.g. S1 and S2 depicted as being sent from the objects 12 in FIG. 15).

For instance, in some implementations, the exemplary operation O11 may include the operation of O1109 for retrieving one or more elements of the user advisory information from one or more storage portions. An exemplary implementation can include the storage retrieving module 173k of FIG. 11 directing the object 12 of FIG. 10 to retrieve one or more elements of the user advisory information from one or more storage portions of the storage 136 of the advisory output 104 of FIG. 10. Retrieval could be based at least in part upon physical status information including information regarding one or more spatial aspects of one or more portions of each of the two or more devices received by the object 12 through the communication unit 112 or obtained by the object by one or more of the sensors 108.

For instance, in some implementations, the exemplary operation O11 may include the operation of O1110 for obtaining information regarding user advisory information expressed relative to one or more objects other than the two or more devices and may be, executed by, for example, the object relative obtaining module 173l of FIG. 11 directing the communication unit 112 of the object 12 of FIG. 10 to receive through one or more of the transceiver components 156 user advisory information (e.g. including M1 and M2 as depicted in FIG. 14 and in FIG. 15) from the advisory system 118 of FIG. 3. In implementations the user advisory information can based at least in part upon physical status information including information regarding one or more spatial aspects of one or more portions of each of the two or more devices received by the object 12 through the communication unit 112 or obtained by the object by one or more of the sensors 108 and expressed relative to one or more objects other than the objects 12 as devices. For instance, in some implementations the obtained information can be related to positional or other spatial aspects of the objects 12 as related to one or more of the other objects 14 (such as structural members of a building, artwork, furniture, or other objects) that are not being used by the subject 10 or are otherwise not involved with influencing the subject regarding physical status of the subject, such as posture. For instance, the spatial information obtained can be expressed in terms of distances between the objects 12 and the other objects 14.

FIG. 21

Figure 21:
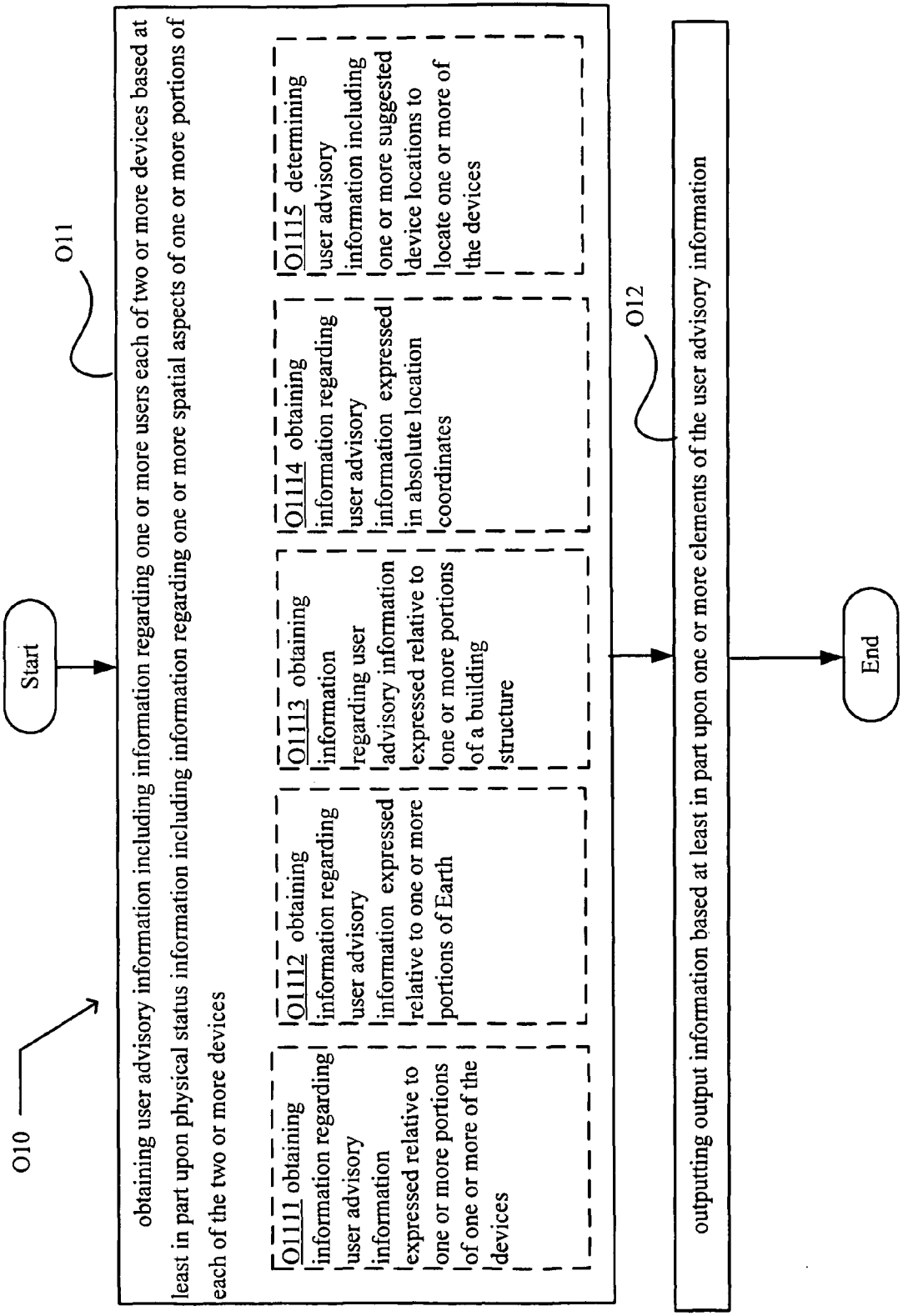
FIG. 21 is a high-level flowchart including exemplary implementations of operation O11 of FIG. 18.

FIG. 21 illustrates various implementations of the exemplary operation O11 of FIG. 18. In particular, FIG. 21 illustrates example implementations where the operation O11 includes one or more additional operations including, for example, operations O1111, O1112, O1113, O1114, and/or O1115, which may be executed generally by, in some instances, In particular, one or more sensing components of the sensing unit 110 of the status determination system 158 of FIG. 6.

For instance, in some implementations, the exemplary operation O11 may include the operation of O1111 for obtaining information regarding user advisory information expressed relative to one or more portions of one or more of the devices and may be, executed by, for example, the device relative obtaining module 173m of FIG. 11 directing the communication unit 112 of the object 12 of FIG. 10 to receive through one or more of the transceiver components 156 user advisory information (e.g. including M1 and M2 as depicted in FIG. 14 and in FIG. 15) from the advisory system 118 of FIG. 3. In implementations the user advisory information can be based at least in part upon physical status information including information regarding one or more spatial aspects of one or more portions of each of the two or more devices received by the object 12 through the communication unit 112 or obtained by the object by one or more of the sensors 108 and expressed relative to one or more portions of one or more of the objects 12 as devices. For instance, in some implementations the obtained information can be related to positional or other spatial aspects of the objects 12 as related to each other (such as structural members of a building, artwork, furniture, or other objects) that are not being used by the subject 10 or are otherwise not involved with influencing the subject regarding physical status of the subject, such as posture. For instance, the spatial information obtained can be expressed in terms of distances between the objects 12.

For instance, in some implementations, the exemplary operation O11 may include the operation of O1112 for obtaining information regarding user advisory information expressed relative to one or more portions of Earth and may be, executed by, for example, the earth relative obtaining module 173n of FIG. 11 directing the communication unit 112 of the object 12 of FIG. 10 to receive through one or more of the transceiver components 156 user advisory information (e.g. including M1 and M2 as depicted in FIG. 14 and in FIG. 15) from the advisory system 118 of FIG. 3. In implementations the user advisory information can be based at least in part upon physical status information including information regarding one or more spatial aspects of one or more portions of each of the two or more devices received by the object 12 through the communication unit 112 or obtained by the object by one or more of the sensors 108 and expressed relative to one or more portions of Earth. For instance, in some implementations the obtained information can be expressed relative to global positioning system (GPS) coordinates, geographical features or other aspects, or otherwise expressed relative to one or more portions of Earth.

For instance, in some implementations, the exemplary operation O11 may include the operation of O1113 for obtaining information regarding user advisory information expressed relative to one or more portions of a building structure. and may be, executed by, for example, the building relative obtaining module 173o of FIG. 11 directing the communication unit 112 of the object 12 of FIG. 10 to receive through one or more of the transceiver components 156 user advisory information (e.g. including M1 and M2 as depicted in FIG. 14 and in FIG. 15) from the advisory system 118 of FIG. 3. In implementations the user advisory information can be based at least in part upon physical status information including information regarding one or more spatial aspects of one or more portions of each of the two or more devices received by the object 12 through the communication unit 112 or obtained by the object by one or more of the sensors 108 and expressed relative to one or more portions of a building structure. For instance, in some implementations the obtained information can be expressed relative to one or more portions of a building structure that houses the subject 10 and the objects 12 or is nearby to the subject and the objects.

For instance, in some implementations, the exemplary operation O11 may include the operation of O1114 for obtaining information regarding user advisory information expressed in absolute location coordinates and may be, executed by, for example, the absolute location module 173p of FIG. 11 directing the communication unit 112 of the object 12 of FIG. 10 to receive through one or more of the transceiver components 156 user advisory information (e.g. including M1 and M2 as depicted in FIG. 14 and in FIG. 15) from the advisory system 118 of FIG. 3. In implementations the user advisory information can be based at least in part upon physical status information including information regarding one or more spatial aspects of one or more portions of each of the two or more devices received by the object 12 through the communication unit 112 or obtained by the object by one or more of the sensors 108 and expressed in absolute location coordinates. For instance, in some implementations the obtained information can be expressed in terms of global positioning system (GPS) coordinates.

For instance, in some implementations, the exemplary operation O11 may include the operation of O1115 for determining user advisory information including one or more suggested device locations to locate one or more of the devices. An exemplary implementation may include the device location module 173q of FIG. 11 directing the advisory system 118 of the objects 12 as devices of FIG. 16 internally to receive physical status information from the sensors 108 of the object as shown in FIG. 16. In implementations, the control 122 of the advisory resource unit 102 of the advisory system 118 can access the memory 128 and/or the storage unit 130 of the advisory resource unit for retrieval or can otherwise use an algorithm contained in the memory to generate a suggested posture or other suggested status for the subject 10 as a user. Based upon the suggested status for the subject 10 as a user and the physical status information regarding the objects 12 as devices, the control 122 can run an algorithm contained in the memory 128 of the advisory resource unit 102 to generate one or more suggested locations that one or more of the objects as devices could be moved to in order to allow the posture or other status of the subject as a user of the object to be changed as advised. As a result, the advisory resource unit 102 can perform determining user advisory information including one or more suggested device locations to locate one or more of the objects 12 as devices.

FIG. 22

Figure 22:
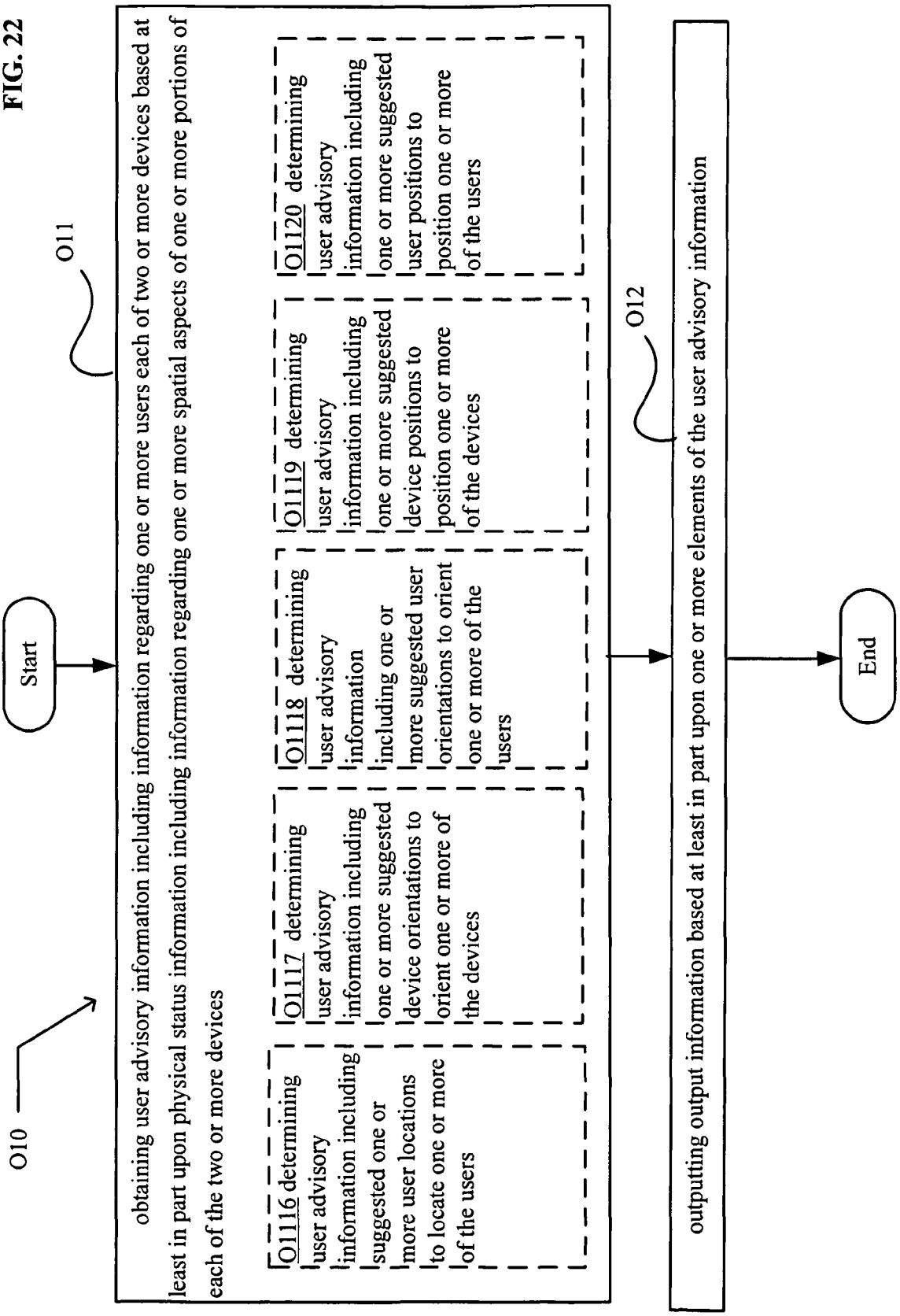
FIG. 22 is a high-level flowchart including exemplary implementations of operation O11 of FIG. 18.

FIG. 22 illustrates various implementations of the exemplary operation O11 of FIG. 18. In particular, FIG. 22 illustrates example implementations where the operation O11 includes one or more additional operations including, for example, operations O1116, O1117, O1118, O1119, and/or O1120, which may be executed generally by, in some instances, one or more of the sensors 108 of the object 12 of FIG. 10 or one or more sensing components of the sensing unit 110 of the status determination system 158 of FIG. 6.

For instance, in some implementations, the exemplary operation O11 may include the operation of O1116 for determining user advisory information including suggested one or more user locations to locate one or more of the users. An exemplary implementation may include the user location module 173r of FIG. 11 directing the advisory system 118 of the objects 12 as devices of FIG. 16 internally to receive physical status information from the sensors 108 of the object as shown in FIG. 16. In implementations, the control 122 of the advisory resource unit 102 of the advisory system 118 can access the memory 128 and/or the storage unit 130 of the advisory resource unit for retrieval or can otherwise use an algorithm contained in the memory to generate a suggested posture or other suggested status for the subject 10 as a user. Based upon the suggested status for the subject 10 as a user and the physical status information regarding the objects 12 as devices, the control 122 can run an algorithm contained in the memory 128 of the advisory resource unit 102 to generate one or more suggested device locations that the objects as devices could be moved to in order to allow the posture or other status of the subject as a user of the object to be changed as advised. As a result, the advisory resource unit 102 can perform determining user advisory information including one or more suggested device locations to locate one or more of the objects 12 as devices.

For instance, in some implementations, the exemplary operation O11 may include the operation of O1117 for determining user advisory information including one or more suggested device orientations to orient one or more of the devices. An exemplary implementation may include the device orientation module 173s of FIG. 11 directing the advisory system 118 of the objects 12 as devices of FIG. 16 internally to receive physical status information from the sensors 108 of the object as shown in FIG. 16. In implementations, the control 122 of the advisory resource unit 102 of the advisory system 118 can access the memory 128 and/or the storage unit 130 of the advisory resource unit for retrieval or can otherwise use an algorithm contained in the memory to generate a suggested posture or other suggested status for the subject 10 as a user. Based upon the suggested status for the subject 10 as a user and the physical status information regarding the objects 12 as devices, the control 122 can run an algorithm contained in the memory 128 of the advisory resource unit 102 to generate one or more suggested device orientations that the objects as devices could be oriented at in order to allow the posture or other status of the subject as a user of the object to be changed as advised. As a result, the advisory resource unit 102 can perform determining user advisory information including one or more suggested device orientations to orient one or more of the objects 12 as devices.

For instance, in some implementations, the exemplary operation O11 may include the operation of O1118 for determining user advisory information including one or more suggested user orientations to orient one or more of the users. An exemplary implementation may include the user orientation module 173t of FIG. 11 directing the advisory system 118 of the objects 12 as devices of FIG. 16 internally to receive physical status information from the sensors 108 of the object as shown in FIG. 16. In implementations, the control 122 of the advisory resource unit 102 of the advisory system 118 can access the memory 128 and/or the storage unit 130 of the advisory resource unit for retrieval or can otherwise use an algorithm contained in the memory to generate a suggested posture or other suggested status for the subject 10 as a user. Based upon the suggested status for the subject 10 as a user and the physical status information regarding the objects 12 as devices, the control 122 can run an algorithm contained in the memory 128 of the advisory resource unit 102 to generate one or more suggested user orientations that the subject 10 as a user could be oriented at in order to allow the posture or other status of the subject as a user of the object to be changed as advised. As a result, the advisory resource unit 102 can perform determining user advisory information including one or more suggested user orientations to orient one or more of the subjects 10 as users.

For instance, in some implementations, the exemplary operation O11 may include the operation of O1119 for determining user advisory information including one or more suggested device positions to position one or more of the devices. An exemplary implementation may include the device position module 173u of FIG. 11 directing the advisory system 118 of the objects 12 as devices of FIG. 16 internally to receive physical status information from the sensors 108 of the object as shown in FIG. 16. In implementations, the control 122 of the advisory resource unit 102 of the advisory system 118 can access the memory 128 and/or the storage unit 130 of the advisory resource unit for retrieval or can otherwise use an algorithm contained in the memory to generate a suggested posture or other suggested status for the subject 10 as a user. Based upon the suggested status for the subject 10 as a user and the physical status information regarding the objects 12 as devices, the control 122 can run an algorithm contained in the memory 128 of the advisory resource unit 102 to generate one or more suggested device positions that the object 12 as a device could be positioned to in order to allow the posture or other status of the subject as a user of the object to be changed as advised. As a result, the advisory resource unit 102 can perform determining user advisory information including one or more suggested device positions to position one or more of the objects 12 as devices.

For instance, in some implementations, the exemplary operation O11 may include the operation of O1120 for determining user advisory information including one or more suggested user positions to position one or more of the users. An exemplary implementation may include the user position module 173v of FIG. 11 directing the advisory system 118 of the objects 12 as devices of FIG. 16 internally to receive physical status information from the sensors 108 of the object as shown in FIG. 16. In implementations, the control 122 of the advisory resource unit 102 of the advisory system 118 can access the memory 128 and/or the storage unit 130 of the advisory resource unit for retrieval or can otherwise use an algorithm contained in the memory to generate a suggested posture or other suggested status for the subject 10 as a user. Based upon the suggested status for the subject 10 as a user and the physical status information regarding the objects 12 as devices, the control 122 can run an algorithm contained in the memory 128 of the advisory resource unit 102 to generate one or more suggested user positions that the subject 10 as a user could be positioned to in order to allow the posture or other status of the subject as a user of the object to be changed as advised. As a result, the advisory resource unit 102 can perform determining user advisory information including one or more suggested user positions to position one or more of the subjects 10 as users.

FIG. 23

Figure 23:
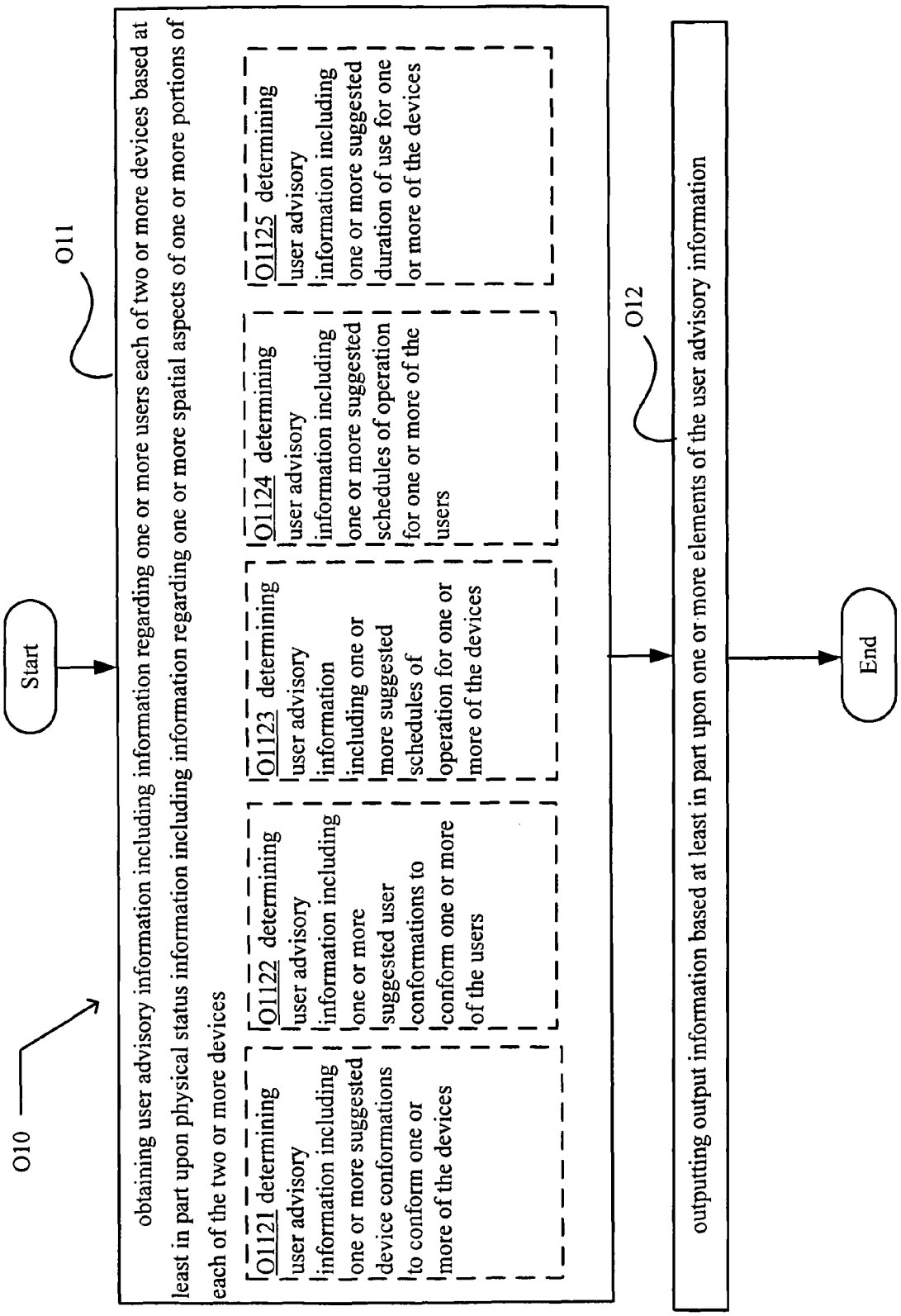
FIG. 23 is a high-level flowchart including exemplary implementations of operation O11 of FIG. 18.

FIG. 23 illustrates various implementations of the exemplary operation O11 of FIG. 18. In particular, FIG. 23 illustrates example implementations where the operation O11 includes one or more additional operations including, for example, operations O1121, O1122, O1123, O1124, and/or O1125, which may be executed generally by, in some instances, one or more of the sensors 108 of the object 12 of FIG. 10.

For instance, in some implementations, the exemplary operation O11 may include the operation of O1121 for determining user advisory information including one or more suggested device conformations to conform one or more of the devices. An exemplary implementation may include the device conformation module 173w of FIG. 11 directing the advisory system 118 of the objects 12 as devices of FIG. 16 internally to receive physical status information from the sensors 108 of the object as shown in FIG. 16. In implementations, the control 122 of the advisory resource unit 102 of the advisory system 118 can access the memory 128 and/or the storage unit 130 of the advisory resource unit for retrieval or can otherwise use an algorithm contained in the memory to generate a suggested posture or other suggested status for the subject 10 as a user. Based upon the suggested status for the subject 10 as a user and the physical status information regarding the objects 12 as devices, the control 122 can run an algorithm contained in the memory 128 of the advisory resource unit 102 to generate one or more suggested device conformations that the objects 12 as one or more devices could be conformed to in order to allow the posture or other status of the subject as a user of the object to be changed as advised. As a result, the advisory resource unit 102 can perform determining user advisory information including one or more suggested device conformations to conform one or more of the objects 12 as devices.

For instance, in some implementations, the exemplary operation O11 may include the operation of O1122 for determining user advisory information including one or more suggested user conformations to conform one or more of the users. An exemplary implementation may include the user conformation module 173x of FIG. 11 directing the advisory system 118 of the objects 12 as devices of FIG. 16 internally to receive physical status information from the sensors 108 of the object as shown in FIG. 16. In implementations, the control 122 of the advisory resource unit 102 of the advisory system 118 can access the memory 128 and/or the storage unit 130 of the advisory resource unit for retrieval or can otherwise use an algorithm contained in the memory to generate a suggested posture or other suggested status for the subject 10 as a user. Based upon the suggested status for the subject 10 as a user and the physical status information regarding the objects 12 as devices, the control 122 can run an algorithm contained in the memory 128 of the advisory resource unit 102 to generate one or more suggested user conformations that the subjects 10 as one or more users could be conformed to in order to allow the posture or other status of the subject as a user of the object to be changed as advised. As a result, the advisory resource unit 102 can perform determining user advisory information including one or more suggested user conformations to conform one or more of the subjects 10 as users.

For instance, in some implementations, the exemplary operation O11 may include the operation of O1123 for determining user advisory information including one or more suggested schedules of operation for one or more of the devices. An exemplary implementation may include the device schedule module 173y of FIG. 11 directing the advisory system 118 of the objects 12 as devices of FIG. 16 internally to receive physical status information from the sensors 108 of the object as shown in FIG. 16. In implementations, the control 122 of the advisory resource unit 102 of the advisory system 118 can access the memory 128 and/or the storage unit 130 of the advisory resource unit for retrieval or can otherwise use an algorithm contained in the memory to generate a suggested posture or other suggested status for the subject 10 as a user. Based upon the suggested status for the subject 10 as a user and the physical status information regarding the objects 12 as devices, the control 122 can run an algorithm contained in the memory 128 of the advisory resource unit 102 to generate one or more suggested user conformations that the subjects 10 as one or more users could be conformed to in order to allow the posture or other status of the subject as a user of the object to be changed as advised. As a result, the advisory resource unit 102 can perform determining user advisory information including one or more suggested user conformations to conform one or more of the subjects 10 as users.

For instance, in some implementations, the exemplary operation O11 may include the operation of O1124 for determining user advisory information including one or more suggested schedules of operation for one or more of the users. An exemplary implementation may include the user schedule module 173z of FIG. 11 directing the advisory system 118 of the objects 12 as devices of FIG. 16 internally to receive physical status information from the sensors 108 of the object as shown in FIG. 16. In implementations, the control 122 of the advisory resource unit 102 of the advisory system 118 can access the memory 128 and/or the storage unit 130 of the advisory resource unit for retrieval or can otherwise use an algorithm contained in the memory to generate a suggested schedule to assume a suggested posture or a suggested schedule to assume other suggested status for the subject 10 as a user. Based upon the suggested schedule to assume a status for the subject 10 as a user and the physical status information regarding the objects 12 as devices, the control 122 can run an algorithm contained in the memory 128 of the advisory resource unit 102 to generate a suggested schedule to operate the objects as devices to allow for the suggested schedule to assume the suggested posture or other status of the subject as a user of the objects. As a result, the advisory resource unit 102 can perform determining user advisory information including one or more suggested schedules of operation for one or more of the subjects 10 as users.

For instance, in some implementations, the exemplary operation O11 may include the operation of O1125 for determining user advisory information including one or more suggested duration of use for one or more of the devices. An exemplary implementation may include the device duration module 173aa of FIG. 11 directing the advisory system 118 of the objects 12 as devices of FIG. 16 internally to receive physical status information from the sensors 108 of the object as shown in FIG. 16. In implementations, the control 122 of the advisory resource unit 102 of the advisory system 118 can access the memory 128 and/or the storage unit 130 of the advisory resource unit for retrieval or can otherwise use an algorithm contained in the memory to generate a suggested duration to assume a suggested posture or a suggested duration to assume other suggested status for the subject 10 as a user. Based upon the suggested duration to assume a status for the subject 10 as a user and the physical status information regarding the objects 12 as devices, the control 122 can run an algorithm contained in the memory 128 of the advisory resource unit 102 to generate a suggested duration to operate the objects as devices to allow for the suggested duration to assume the suggested posture or other status of the subject as a user of the objects. As a result, the advisory resource unit 102 can perform determining user advisory information including one or more suggested duration of use for one or more of the objects 12 as devices.

FIG. 24

Figure 24:
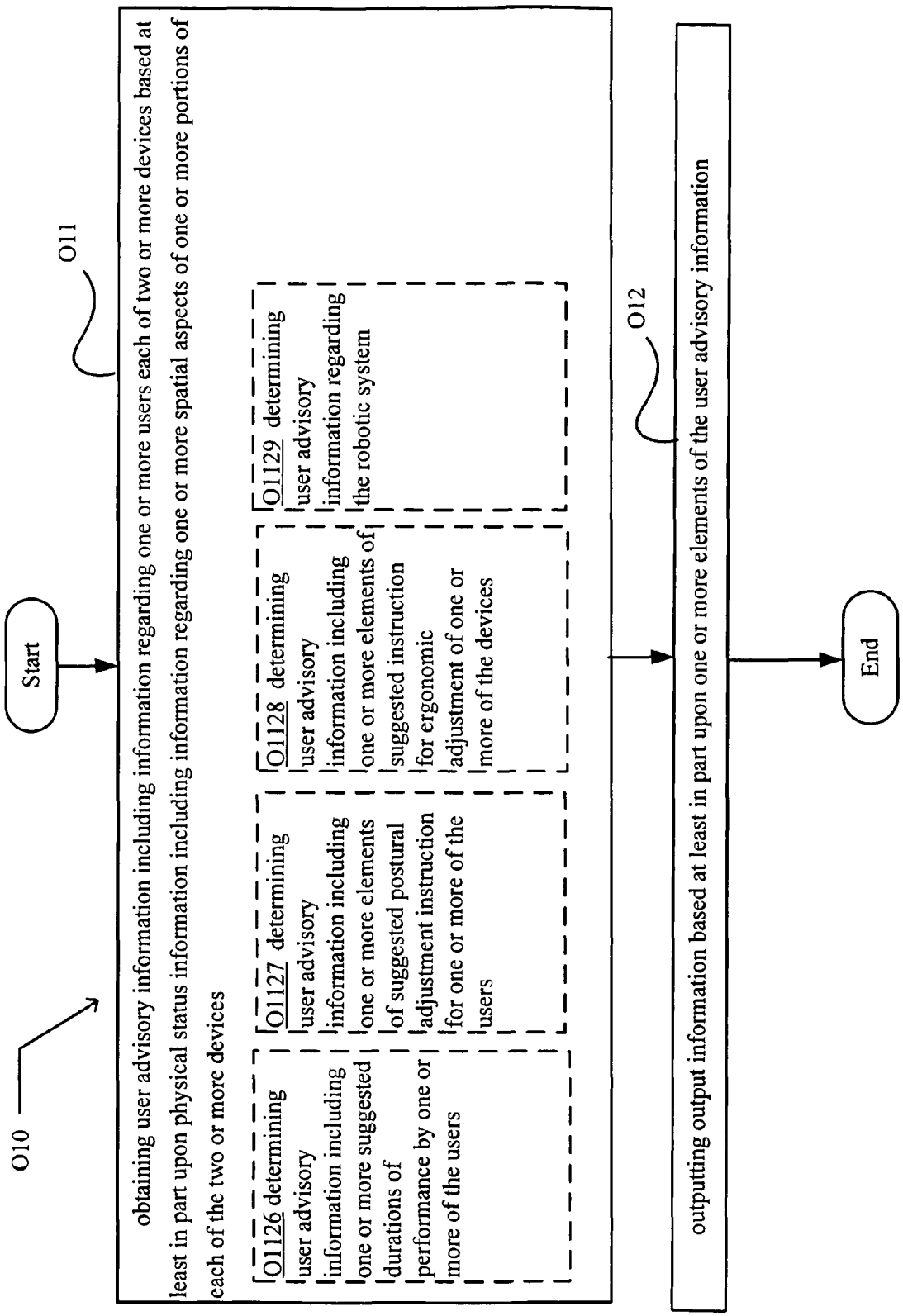
FIG. 24 is a high-level flowchart including exemplary implementations of operation O11 of FIG. 18.

FIG. 24 illustrates various implementations of the exemplary operation O11 of FIG. 18. In particular, FIG. 24 illustrates example implementations where the operation O11 includes one or more additional operations including, for example, operations O1126, O1127, O1128, and/or O1129, which may be executed generally by, in some instances, one or more of the sensors 108 of the object 12 of FIG. 10 or one or more sensing components of the sensing unit 110 of the status determination system 158 of FIG. 6.

For instance, in some implementations, the exemplary operation O11 may include the operation of O1126 for determining user advisory information including one or more suggested durations of performance by one or more of the users. An exemplary implementation may include the user performance module 173ab of FIG. 11 directing the advisory system 118 of the objects 12 as devices of FIG. 16 internally to receive physical status information from the sensors 108 of the object as shown in FIG. 16. In implementations, the control 122 of the advisory resource unit 102 of the advisory system 118 can access the memory 128 and/or the storage unit 130 of the advisory resource unit for retrieval or can otherwise use an algorithm contained in the memory to generate a suggested duration to assume a suggested posture or a suggested duration to assume other suggested status for the subject 10 as a user. Based upon the suggested duration to assume a status for the subject 10 as a user and the physical status information regarding the objects 12 as devices, the control 122 can run an algorithm contained in the memory 128 of the advisory resource unit 102 to generate a suggested duration of performance by one or more of the users to operate the objects as devices to allow for the suggested duration to assume the suggested posture or other status of the subject as a user of the objects. As a result, the advisory resource unit 102 can perform determining user advisory information including one or more suggested durations of performance by one or more of the subjects 10 as users.

For instance, in some implementations, the exemplary operation O11 may include the operation of O1127 for determining user advisory information including one or more elements of suggested postural adjustment instruction for one or more of the users. An exemplary implementation may include the postural adjustment module 173ac of FIG. 11 directing the advisory system 118 of the objects 12 as devices of FIG. 16 internally to receive physical status information from the sensors 108 of the object as shown in FIG. 16. In implementations, the control 122 of the advisory resource unit 102 of the advisory system 118 can access the memory 128 and/or the storage unit 130 of the advisory resource unit for retrieval or can otherwise use an algorithm contained in the memory to generate one or more elements of suggested postural status or other status for one or more of the subjects 10 as users. Based upon the suggested postural status or other status for the subject 10 as a user and the physical status information regarding the objects 12 as devices, the control 122 can run an algorithm contained in the memory 128 of the advisory resource unit 102 to generate one or more elements of suggested postural adjustment instruction of ether subject 10 as a user to allow for postural status or other status as advised. As a result, the advisory resource unit 102 can perform determining user advisory information including one or more one or more elements of suggested postural adjustment instruction for one or more of the subjects 10 as users.

For instance, in some implementations, the exemplary operation O11 may include the operation of O1128 for determining user advisory information including one or more elements of suggested instruction for ergonomic adjustment of one or more of the devices. An exemplary implementation may include the ergonomic adjustment module 173ad of FIG. 11 directing the advisory system 118 of the objects 12 as devices of FIG. 16 internally receiving physical status information from the sensors 108 of the object as shown in FIG. 16. In implementations, the control 122 of the advisory resource unit 102 of the advisory system 118 can access the memory 128 and/or the storage unit 130 of the advisory resource unit for retrieval or can otherwise use an algorithm contained in the memory to generate a suggested postural status or other suggested status to assume for the subject 10 as a user. Based upon the suggested postural status or other suggested status assume for the subject 10 as a user and the physical status information regarding the objects 12 as devices, the control 122 can run an algorithm contained in the memory 128 of the advisory resource unit 102 to generate one or more elements of suggested instruction for ergonomic adjustment of one or more of the objects as devices to allow for the suggested duration to assume the suggested postural status or other status of the subject as a user of the objects. As a result, the advisory resource unit 102 can perform determining user advisory information including one or more elements of suggested instruction for ergonomic of one or more of the objects 12 as devices.

For instance, in some implementations, the exemplary operation O11 may include the operation of O1129 for determining user advisory information regarding the robotic system. An exemplary implementation may include the robotic system module 173ae of FIG. 11 directing the advisory system 118 of the objects 12 as devices of FIG. 16 internally receiving physical status information from the sensors 108 of the object as shown in FIG. 16. In implementations, the control 122 of the advisory resource unit 102 of the advisory system 118 can access the memory 128 and/or the storage unit 130 of the advisory resource unit for retrieval or can otherwise use an algorithm contained in the memory to generate one or more elements of suggested postural status or other status for one or more of the subjects 10 as robotic systems. Based upon the suggested postural status or other status for the subject 10 as a user and the physical status information regarding the objects 12 as devices, the control 122 can run an algorithm contained in the memory 128 of the advisory resource unit 102 to generate one or more elements of suggested user advisory information regarding the subject 10 as a user to allow for postural status or other status as advised. As a result, the advisory resource unit 102 can perform determining user advisory information regarding the robotic system as one or more of the subjects 10.

FIG. 25

Figure 25:
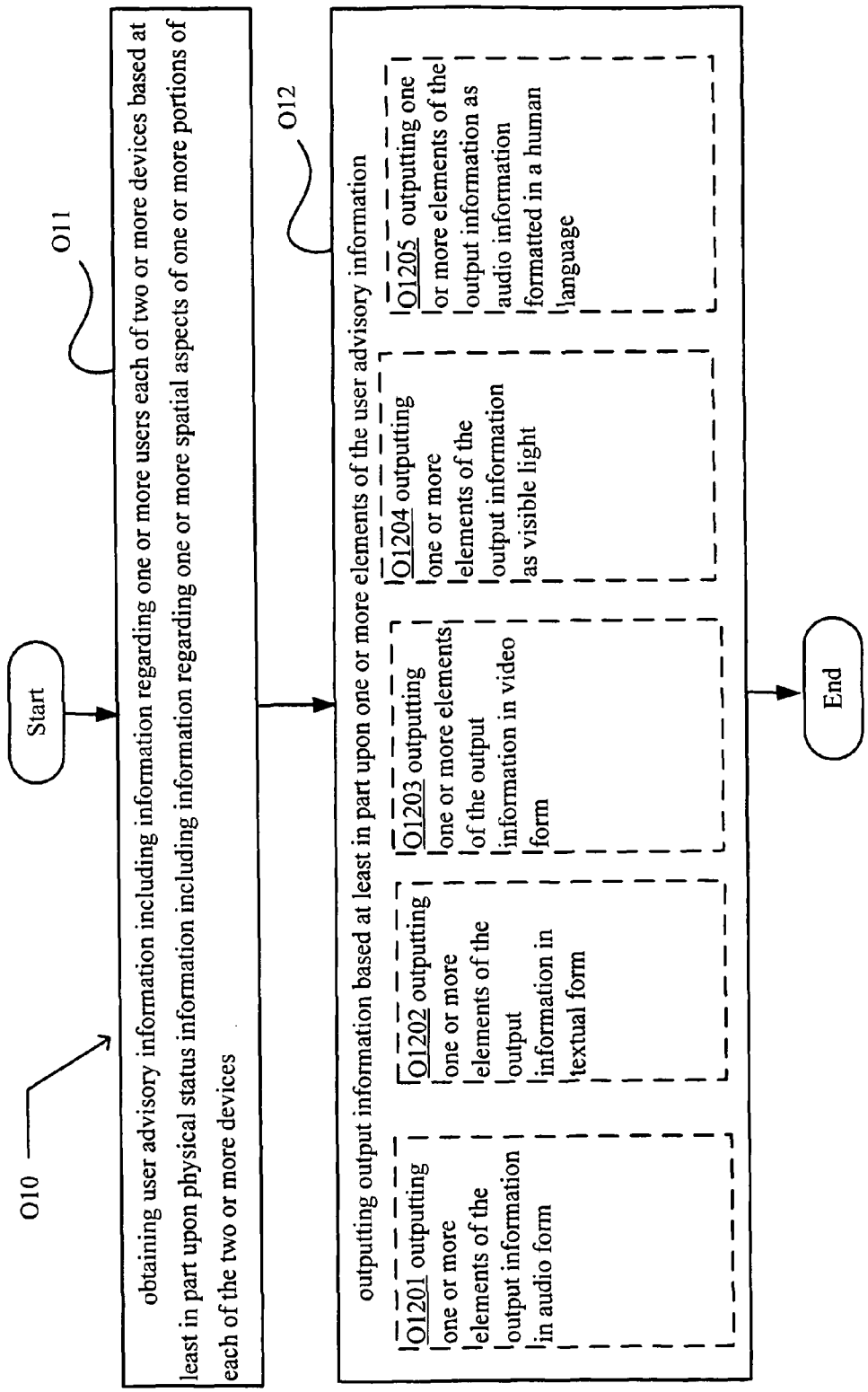
FIG. 25 is a high-level flowchart including exemplary implementations of operation O12 of FIG. 18.

FIG. 25 illustrates various implementations of the exemplary operation O12 of FIG. 18. In particular, FIG. 25 illustrates example implementations where the operation O12 includes one or more additional operations including, for example, operations O1201, O1202, O1203, O1204, and O1205, which may be executed generally by, in some instances, the status determination unit 106 of the status determination system 158 of FIG. 6.

For instance, in some implementations, the exemplary operation O12 may include the operation of O1201 for outputting one or more elements of the output information in audio form. An exemplary implementation may include the audio output module 145a of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the audio output 134*a* (such as an audio speaker or alarm) of the advisory output 104 can output one or more elements of the output information in audio form.

For instance, in some implementations, the exemplary operation O12 may include the operation of O1202 for outputting one or more elements of the output information in textual form. An exemplary implementation may include the textual output module 145*b* directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the textual output 134*b* (such as a display showing text or a printer) of the advisory output 104 can output one or more elements of the output information in textual form.

For instance, in some implementations, the exemplary operation O12 may include the operation of O1203 for outputting one or more elements of the output information in video form. An exemplary implementation may include the video output module 145*c* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the video output 134*c* (such as a display) of the advisory output 104 can output one or more elements of the output information in video form.

For instance, in some implementations, the exemplary operation O12 may include the operation of O1204 for outputting one or more elements of the output information as visible light. An exemplary implementation may include the light output module 145*d* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the light output 134*d* (such as a light, flashing, colored variously, or a light of some other form) of the advisory output 104 can output one or more elements of the output information as visible light.

For instance, in some implementations, the exemplary operation O12 may include the operation of O1205 for outputting one or more elements of the output information as audio information formatted in a human language. An exemplary implementation may include the language output module 145*e* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the control 140 of the advisory output 104 may process the advisory based content into an audio based message formatted in a human language and output the audio based message through the audio output 134*a* (such as an audio speaker) so that the advisory output can output one or more elements of the output information as audio information formatted in a human language.

FIG. 26

Figure 26:
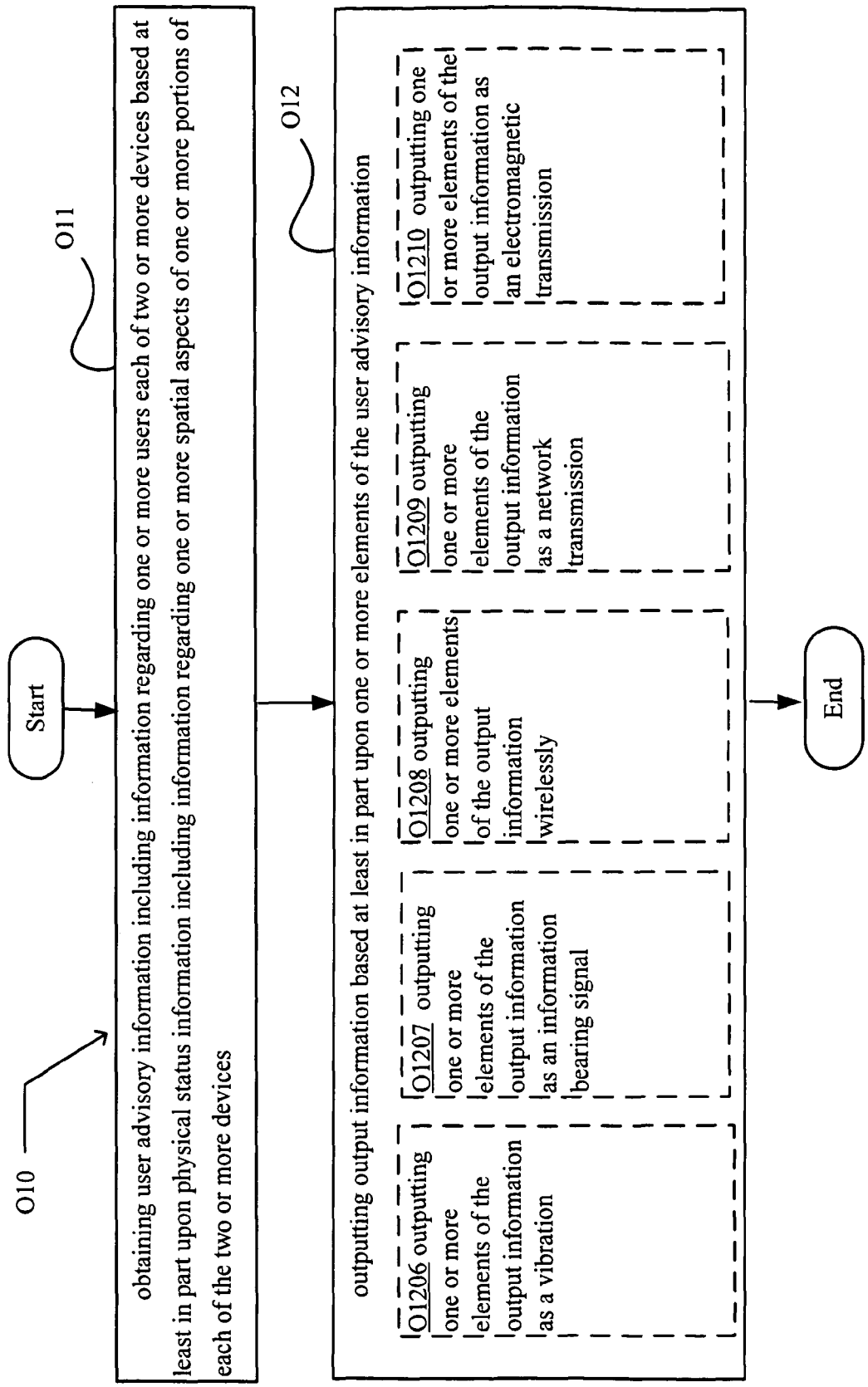
FIG. 26 is a high-level flowchart including exemplary implementations of operation O12 of FIG. 18.

FIG. 26 illustrates various implementations of the exemplary operation O12 of FIG. 18. In particular, FIG. 26 illustrates example implementations where the operation O12 includes one or more additional operations including, for example, operation O1206, O1207, O1208, O1209, and O1210, which may be executed generally by the advisory system 118 of FIG. 3.

For instance, in some implementations, the exemplary operation O12 may include the operation of O1206 for outputting one or more elements of the output information as a vibration. An exemplary implementation may include the vibration output module 145*f* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the vibrator output 134*e* of the advisory output 104 can output one or more elements of the output information as a vibration.

For instance, in some implementations, the exemplary operation O12 may include the operation of O1207 for outputting one or more elements of the output information as an information bearing signal. An exemplary implementation may include the signal output module 145*g* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the transmitter output 134*f* of the advisory output 104 can output one or more elements of the output information as an information bearing signal.

For instance, in some implementations, the exemplary operation O12 may include the operation of O1208 for outputting one or more elements of the output information wirelessly. An exemplary implementation may include the wireless output module 145*h* of FIG. 5 directing the wireless output module 145*h* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the wireless output 134*g* of the advisory output 104 can output one or more elements of the output information wirelessly.

For instance, in some implementations, the exemplary operation O12 may include the operation of O1209 for outputting one or more elements of the output information as a network transmission. An exemplary implementation may include the network output module 145*i* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the network output 134*h* of the advisory output 104 can output one or more elements of the output information as a network transmission.

For instance, in some implementations, the exemplary operation O12 may include the operation of O1210 for outputting one or more elements of the output information as an electromagnetic transmission. An exemplary implementation may include the electromagnetic output module 145*j* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the electromagnetic output1 134*i* of the advisory output 104 can output one or more elements of the output information as an electromagnetic transmission.

FIG. 27

Figure 27:
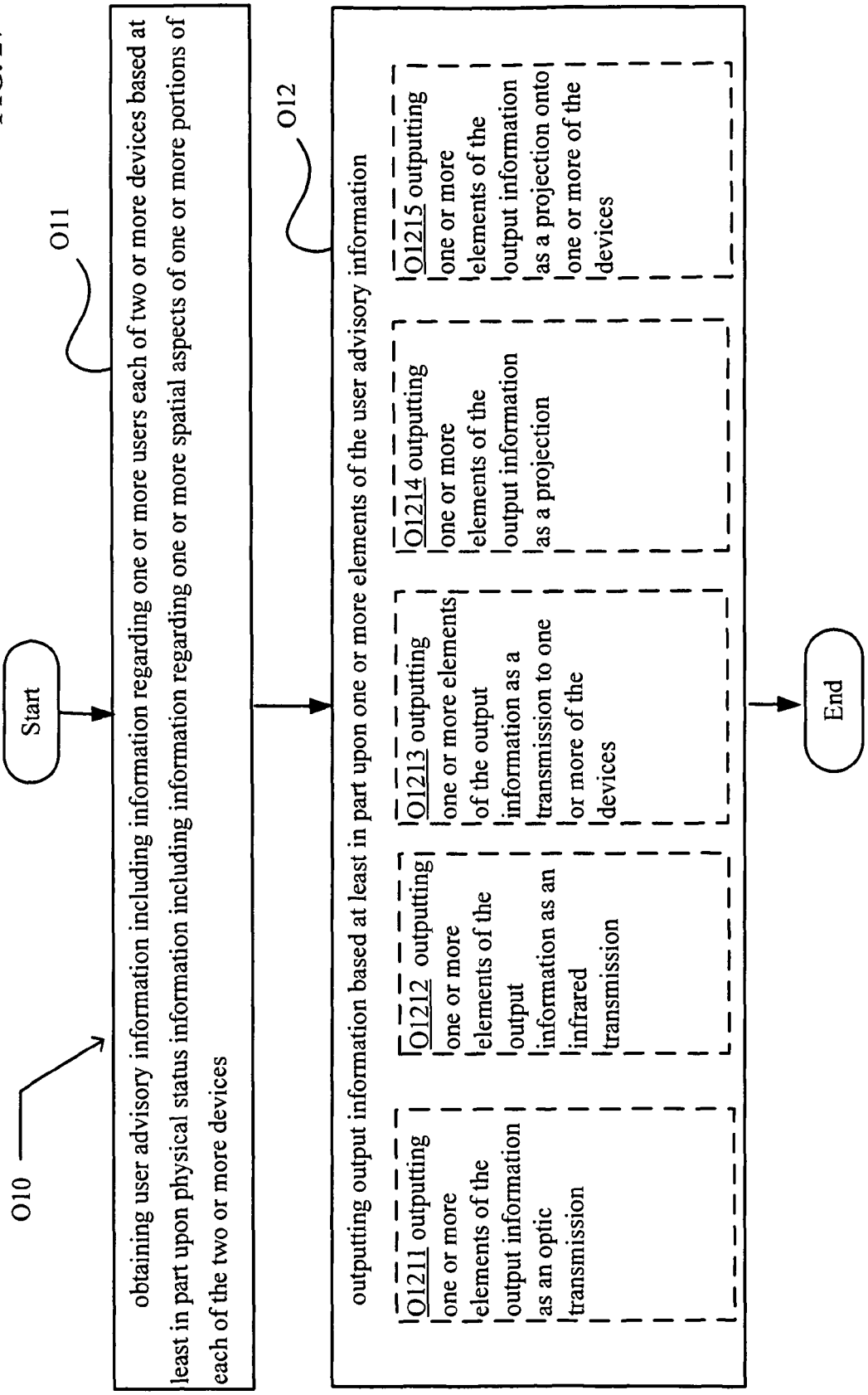
FIG. 27 is a high-level flowchart including exemplary implementations of operation O12 of FIG. 18.

FIG. 27 illustrates various implementations of the exemplary operation O12 of FIG. 18. In particular, FIG. 27 illustrates example implementations where the operation O12 includes one or more additional operations including, for example, operation O1211, O1212, O1213, O1214, and O1215, which may be executed generally by the advisory system 118 of FIG. 3.

For instance, in some implementations, the exemplary operation O12 may include the operation of O1211 for outputting one or more elements of the output information as an optic transmission. An exemplary implementation may include the optical output module 145*k* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the optic output 134*j* of the advisory output 104 can output one or more elements of the output information as optic transmission.

For instance, in some implementations, the exemplary operation O12 may include the operation of O1212 for outputting one or more elements of the output information as an infrared transmission. An exemplary implementation may include the infrared output module 145*l* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the infrared output 134*k* of the advisory output 104 can output one or more elements of the output information as infrared transmission.

For instance, in some implementations, the exemplary operation O12 may include the operation of O1213 for outputting one or more elements of the output information as a transmission to one or more of the devices. An exemplary implementation may include the transmission output module 145*m* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the transmitter output 134*f* of the advisory output 104 to the communication unit 112 of one or more of the objects 12 as devices so can output one or more elements of the output information as a transmission to one or more devices.

For instance, in some implementations, the exemplary operation O12 may include the operation of O1214 for outputting one or more elements of the output information as a projection. An exemplary implementation may include the projection output module 145*n* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the projector transmitter output 134*l* of the advisory output 104 can output one or more elements of the output information as a projection.

For instance, in some implementations, the exemplary operation O12 may include the operation of O1215 for outputting one or more elements of the output information as a projection onto one or more of the devices. An exemplary implementation may include the projection output module 145*o* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the projector output 134*l* of the advisory output 104 can project unto one or more of the objects 12 as devices one or more elements of the output information as a projection unto one or more of the objects as devices.

FIG. 28

Figure 28:
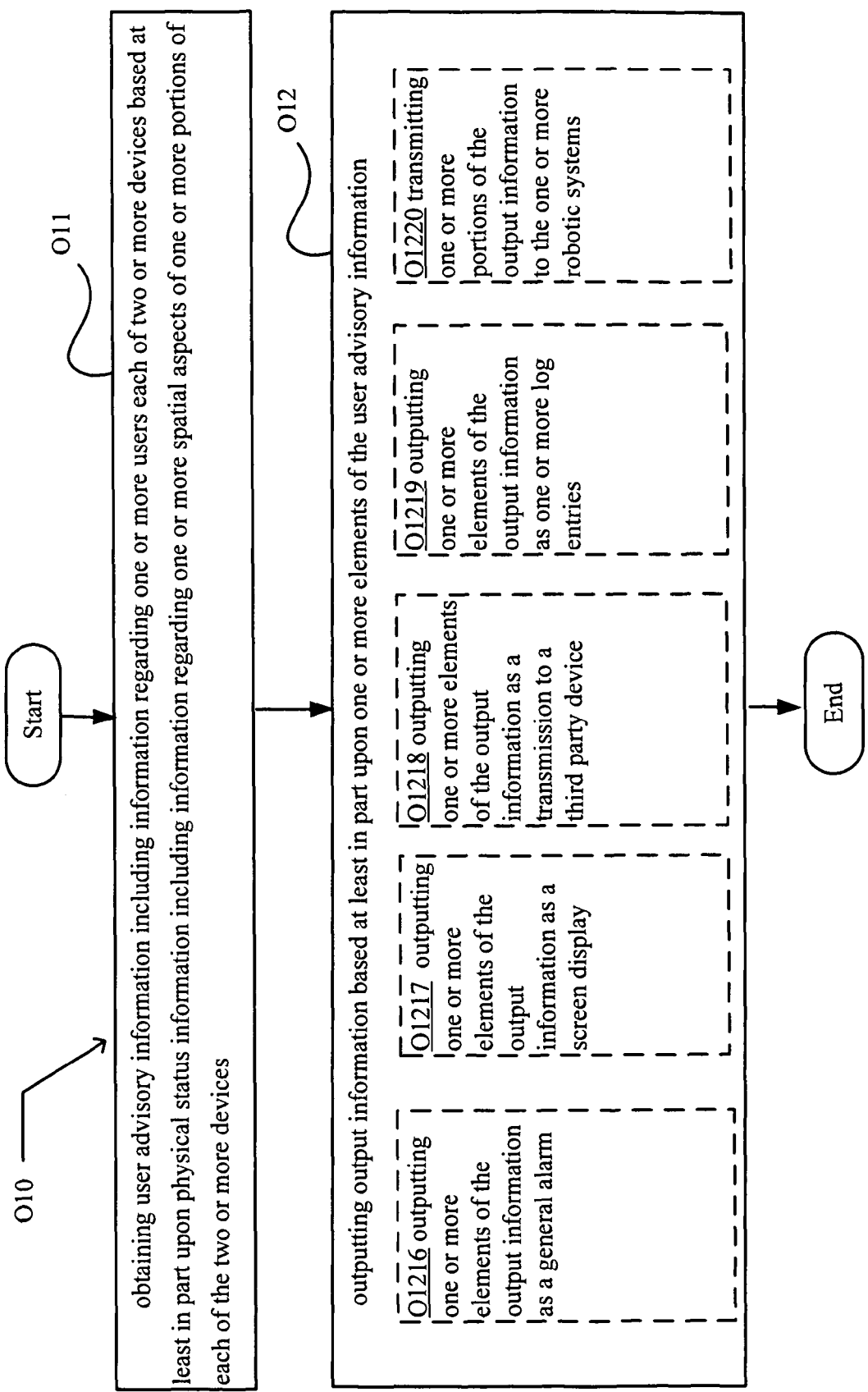
FIG. 28 is a high-level flowchart including exemplary implementations of operation O12 of FIG. 18.

FIG. 28 illustrates various implementations of the exemplary operation O12 of FIG. 18. In particular, FIG. 28 illustrates example implementations where the operation O12 includes one or more additional operations including, for example, operation O1216, O1217, O1218, O1219, and O1220, which may be executed generally by the advisory system 118 of FIG. 3.

For instance, in some implementations, the exemplary operation O12 may include the operation of O1216 for outputting one or more elements of the output information as a general alarm. An exemplary implementation may include the alarm output module 145*p* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the alarm output 134*m* of the advisory output 104 can output one or more elements of the output information as a general alarm.

For instance, in some implementations, the exemplary operation O12 may include the operation of O1217 for outputting one or more elements of the output information as a screen display. An exemplary implementation may include the display output module 145*q* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the display output 134*n* of the advisory output 104 can output one or more elements of the output information as a screen display.

For instance, in some implementations, the exemplary operation O12 may include the operation of O1218 for outputting one or more elements of the output information as a transmission to a third party device. An exemplary implementation may include the third party output module 145*s* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the transmitter output 134*f* of the advisory output 104 can output to the other object 12 one or more elements of the output information as a transmission to a third party device.

For instance, in some implementations, the exemplary operation O12 may include the operation of O1219 for outputting one or more elements of the output information as one or more log entries. An exemplary implementation may include the log output module 145*t* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, the log output 134*o* of the advisory output 104 can output one or more elements of the output information as one or more log entries.

For instance, in some implementations, the exemplary operation O12 may include the operation of O1220 for transmitting one or more portions of the output information to the one or more robotic systems. An exemplary implementation may include the robotic output module 145*u* of FIG. 5 directing the advisory output 104 of the object 12 of FIG. 10 to receive information containing advisory based content from the advisory system 118 either externally (such as "M" depicted in FIG. 14) and internally (such as from the advisory resource 102 to the advisory output within the advisory system of the object, for instance, shown in FIG. 16). After receiving the information containing advisory based content, in some implementations, the transmitter output 134*f* of the advisory output 104 can transmit one or more portions of the output information to the communication units 112 of one or more of the objects 12 as robotic systems.

FIG. 29

Figure 29:
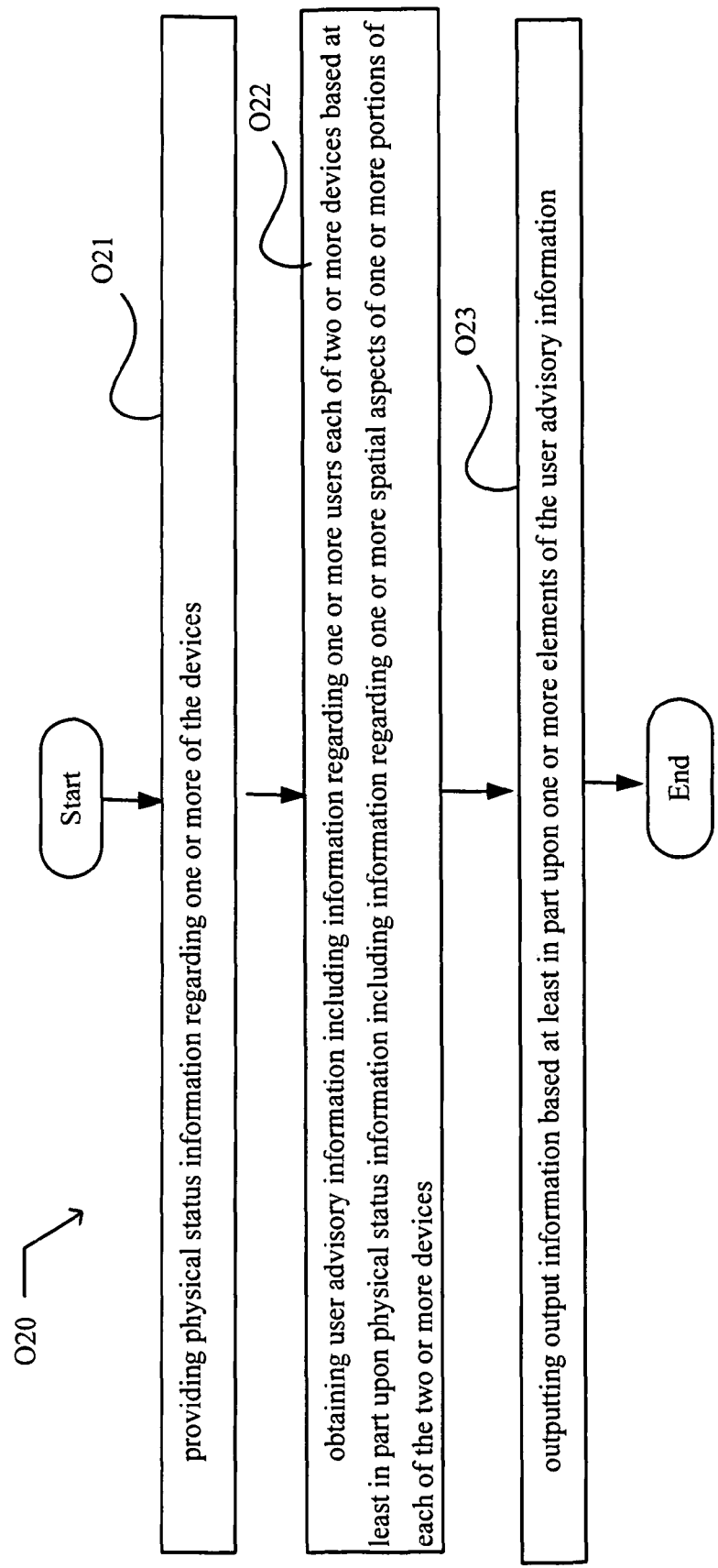
FIG. 29 is a high-level flowchart illustrating an operational flow O20 representing exemplary operations related to providing physical status information regarding one or more of the devices, obtaining user advisory information including information regarding one or more users each of two or more devices based at least in part upon physical status information including information regarding one or more spatial aspects of one or more portions of each of the two or more devices, and outputting output information based at least in part upon one or more elements of the user advisory information at least associated with the depicted exemplary implementations of the postural information system.

In FIG. 29 and those figures that follow, various operations may be depicted in a box-within-a-box manner. Such depictions may indicate that an operation in an internal box may comprise an optional exemplary implementation of the operational step illustrated in one or more external boxes. However, it should be understood that internal box operations may be viewed as independent operations separate from any associated external boxes and may be performed in any sequence with respect to all other illustrated operations, or may be performed concurrently.

After a start operation, the operational flow O20 may move to an operation O21, where providing physical status information regarding one or more of the devices may be, executed by, for example, the providing physical information module 170*cg* of FIG. 9 directing the one of the sensing components of the sensing unit 110 of the status determination unit 158 of FIG. 6, such as the radar based sensing component 110*k*, in which, for example, in some implementations, locations of instances 1 through n of the objects 12 of FIG. 1 can be obtained by the radar based sensing component. In other implementations, other sensing components of the sensing unit 110 of FIG. 6 can be used to obtain physical status information regarding one or more portions for each of the one or more first devices with respect to one or more portions of the second device, including information regarding one or more spatial aspects of the one or more portions of the device, such as information regarding location, position, orientation, visual placement, visual appearance, and/or conformation of the devices. In other implementations, one or more of the sensors 108 of FIG. 10 found on one or more of the objects 12 can be used to in a process of obtained physical status information of the objects, including information regarding one or more spatial aspects of the one or more portions of the device. For example, in some implementations, the gyroscopic sensor 108*f* can be located on one or more instances of the objects 12 can be used in obtaining physical status information including information regarding orientational information of the objects. In other implementations, for example, the accelerometer 108*j* located on one or more of the objects 12 can be used in obtaining conformational information of the objects such as how certain portions of each of the objects are positioned relative to one another. For instance, the object 12 of FIG. 2 entitled "cell device" is shown to have two portions connected through a hinge allowing for closed and open conformations of the cell device. To assist in obtaining the physical status information, for each of the objects 12, the communication unit 112 of the object of FIG. 10 can transmit the physical status information acquired by one or more of the sensors 108 to be received by the communication unit 112 of the status determination system 158 of FIG. 6.

The operational flow O20 may then move to operation O22, where obtaining user advisory information including information regarding one or more users each of two or more devices based at least in part upon physical status information including information regarding one or more spatial aspects of one or more portions of each of the two or more devices may be, executed by, for example, the obtaining information module 173*a* of FIG. 11 directing the communication unit 112 of the object 12 of FIG. 10 to receive through one or more of the transceiver components 156 user advisory information (e.g. including M1 and M2 as depicted in FIG. 14 and in FIG. 15) from the advisory system 118 of FIG. 3. In implementations the user advisory information can include information regarding one or more users each of two or more devices based at least in part upon physical status information including information regarding one or more spatial aspects of one or more portions of each of the two or more devices (e.g. S1 and S2 depicted as being sent from the objects 12 in FIG. 15).

The operational flow O20 may then move to operation O23, where outputting output information based at least in part upon one or more elements of the user advisory information may be executed by, the advisory output 104 of FIG. 1. An exemplary implementation may include the output module 173*b* of FIG. 11 directing the advisory output 104 to receive information containing advisory based content from the advisory system 118 either externally (such as "M" depicted in FIG. 14) and internally (such as from the advisory resource 102 to the advisory output within the advisory system, for instance, shown in FIG. 14). After receiving the information containing advisory based content, the output module 173*b* of FIG. 11 can direct the advisory output 104 to output information (e.g. A1 and A2 of FIG. 14 and FIG. 15) based at least in part upon one or more elements of the user advisory information.

FIG. 30

Figure 30:
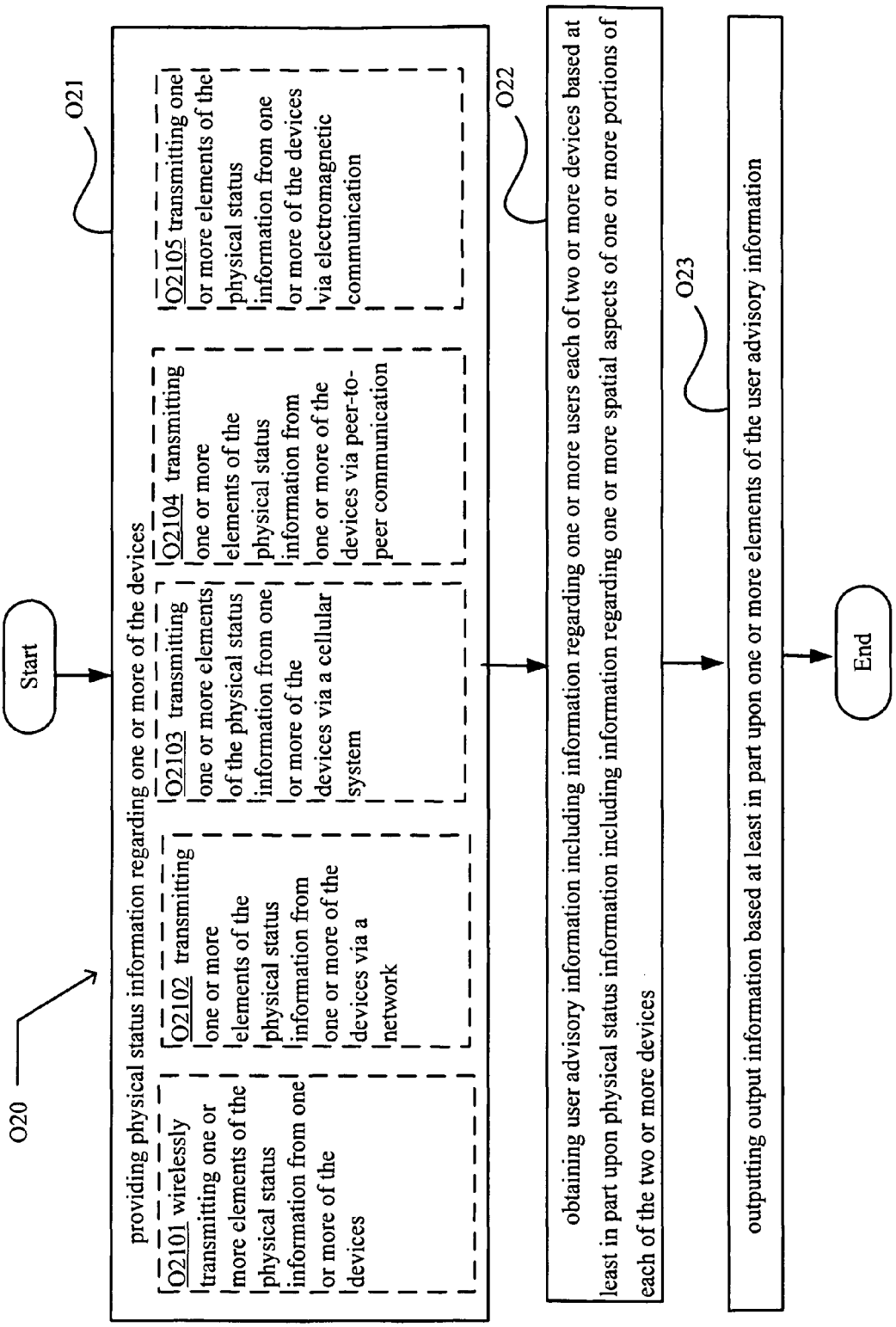
FIG. 30 is a high-level flowchart including exemplary implementations of operation O21 of FIG. 29.

FIG. 30 illustrates various implementations of the exemplary operation O21 of FIG. 29. In particular, FIG. 30 illustrates example implementations where the operation O21 includes one or more additional operations including, for example, operations O2101, O2102, O2103, O2104, and/or O2105, which may be executed generally by, in some instances, one or more of the transceiver components 156 of the communication unit 112 of the status determining system 158 of FIG. 6.

For instance, in some implementations, the exemplary operation O21 may include the operation of O2101 for wirelessly transmitting one or more elements of the physical status information from one or more of the devices. An exemplary implementation may include the wireless transmitting module 173ba of FIG. 12 directing the one or more of the wireless transceiver components 156b of the communication unit 112 of the status determination system 158 of FIG. 6 to receive wireless transmissions transmitted from each wireless transceiver component 156b of FIG. 10 of the communication unit 112 of the objects 12. For example, in some implementations, the transmission D1 from object 1 carrying physical status information regarding object 1 and the transmission D2 from object 2 carrying physical status information about object 2 to the status determination system 158, as shown in FIG. 14, can be sent and received by the wireless transceiver components 156b of the objects 12 and the status determination system 158, respectively, as wireless transmissions such that the objects can be wirelessly transmitting one or more elements of the physical status information from one or more of the objects as devices.

For instance, in some implementations, the exemplary operation O21 may include the operation of O2102 for transmitting one or more elements of the physical status information from one or more of the devices via a network. An exemplary implementation may include the network transmitting module 173bb of FIG. 12 directing the one or more of the network transceiver components 156a of the communication unit 112 of the status determination system 158 of FIG. 6 to receive network transmissions from each network transceiver component 156a of FIG. 10 of the communication unit 112 of the objects 12. For example, in some implementations, the transmission D1 from object 1 carrying physical status information regarding object 1 and the transmission D2 from object 2 carrying physical status information about object 2 to the status determination system 158, as shown in FIG. 14, can be sent and received by the network transceiver components 156a of the objects 12 and the status determination system 158, respectively, as network transmissions such that the objects can be transmitting one or more elements of the physical status information from one or more of the objects as devices via a network.

For instance, in some implementations, the exemplary operation O21 may include the operation of O2103 for transmitting one or more elements of the physical status information from one or more of the devices via a cellular system. An exemplary implementation may include the cellular transmitting module 173bc of FIG. 12 directing the one or more of the cellular transceiver components 156c of the communication unit 112 of the status determination system 158 of FIG. 6 to receive cellular transmissions from each cellular transceiver component 156a of FIG. 10 of the communication unit 112 of the objects 12. For example, in some implementations, the transmission D1 from object 1 carrying physical status information regarding object 1 and the transmission D2 from object 2 carrying physical status information about object 2 to the status determination system 158, as shown in FIG. 14, can be sent and received by the cellular transceiver components 156c of the objects 12 and the status determination system 158, respectively, as cellular transmissions such that the objects can be transmitting one or more elements of the physical status information from one or more of the objects as devices via a cellular network.

For instance, in some implementations, the exemplary operation O21 may include the operation of O2104 for transmitting one or more elements of the physical status information from one or more of the devices via peer-to-peer communication. An exemplary implementation may include the peer-to-peer transmitting module 173bd of FIG. 12 directing the one or more of the peer-to-peer transceiver components 156d of the communication unit 112 of the status determination system 158 of FIG. 6 to receive peer-to-peer transmissions from each peer-to-peer transceiver component 156d of FIG. 10 of the communication unit 112 of the objects 12. For example, in some implementations, the transmission D1 from object 1 carrying physical status information regarding object 1 and the transmission D2 from object 2 carrying physical status information about object 2 to the status determination system 158, as shown in FIG. 14, can be sent and received by the peer-to-peer transceiver components 156d of the objects 12 and the status determination system 158, respectively, as peer-to-peer transmissions such that the objects can be transmitting one or more elements of the physical status information from one or more of the objects as devices via peer-to-peer communication.

For instance, in some implementations, the exemplary operation O21 may include the operation of O2105 for transmitting one or more elements of the physical status information from one or more of the devices via electromagnetic communication. An exemplary implementation may include the EM transmitting module 173be of FIG. 12 directing the one or more of the electromagnetic communication transceiver components 156e of the communication unit 112 of the status determination system 158 of FIG. 6 to receive electromagnetic communication transmissions from each electromagnetic communication transceiver component 156a of FIG. 10 of the communication unit 112 of the objects 12. For example, in some implementations, the transmission D1 from object 1 carrying physical status information regarding object 1 and the transmission D2 from object 2 carrying physical status information about object 2 to the status determination system 158, as shown in FIG. 14, can be sent and received by the electromagnetic communication transceiver components 156c of the objects 12 and the status determination system 158, respectively, as electromagnetic communication transmissions such that the objects can be transmitting one or more elements of the physical status information from one or more of the objects as devices via electromagnetic communication.

FIG. 31

Figure 31:
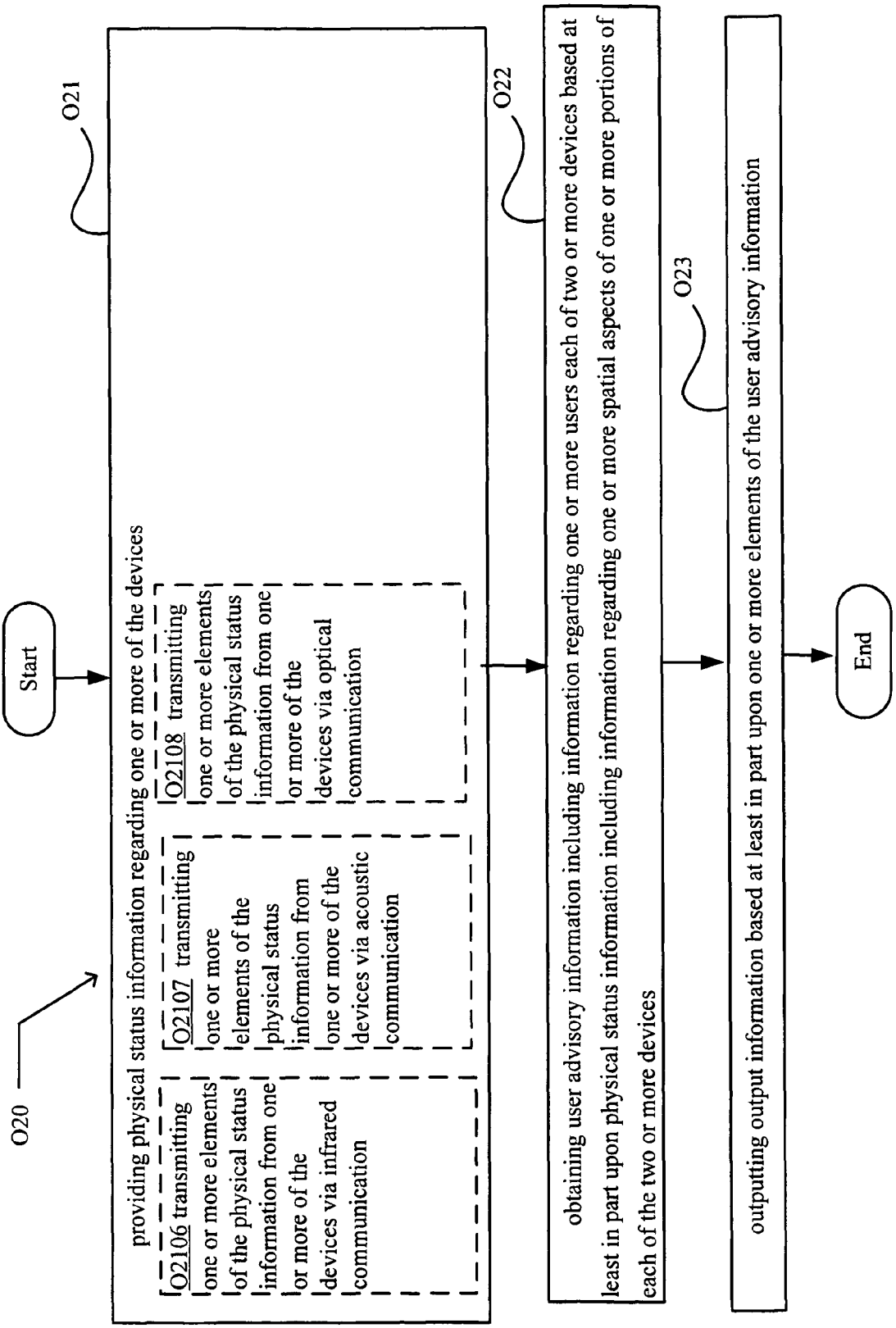
FIG. 31 is a high-level flowchart including exemplary implementations of operation O21 of FIG. 29.

FIG. 31 illustrates various implementations of the exemplary operation O21 of FIG. 29. In particular, FIG. 31 illustrates example implementations where the operation O21 includes one or more additional operations including, for example, operations O2106, O2107, and/or O2108, which may be executed generally by, in some instances, one or more of the transceiver components 156 of the communication unit 112 or one or more sensing components of the sensing unit 110 of the status determination system 158 of FIG. 6.

For instance, in some implementations, the exemplary operation O21 may include the operation of O2106 for transmitting one or more elements of the physical status information from one or more of the devices via infrared communication. An exemplary implementation may include the infrared transmitting module 173bf of FIG. 12 directing the one or more of the infrared transceiver components 156*f* of the communication unit 112 of the status determination system 158 of FIG. 6 receiving infrared transmissions from each infrared transceiver component 156*f* of FIG. 10 of the communication unit 112 of the objects 12. For example, in some implementations, the transmission D1 from object 1 carrying physical status information regarding object 1 and the transmission D2 from object 2 carrying physical status information about object 2 to the status determination system 158, as shown in FIG. 14, can be sent and received by the infrared transceiver components 156*c* of the objects 12 and the status determination system 158, respectively, as infrared transmissions such that the objects can be transmitting one or more elements of the physical status information from one or more of the objects as devices via infrared communication.

For instance, in some implementations, the exemplary operation O21 may include the operation of O2107 for transmitting one or more elements of the physical status information from one or more of the devices via acoustic communication. An exemplary implementation may include the acoustic transmitting module 173*bg* of FIG. 12 directing the one or more of the acoustic transceiver components 156*g* of the communication unit 112 of the status determination system 158 of FIG. 6 to receive acoustic transmissions from each acoustic transceiver component 156*g* of FIG. 10 of the communication unit 112 of the objects 12. For example, in some implementations, the transmission D1 from object 1 carrying physical status information regarding object 1 and the transmission D2 from object 2 carrying physical status information about object 2 to the status determination system 158, as shown in FIG. 14, can be sent and received by the acoustic transceiver components 156*g* of the objects 12 and the status determination system 158, respectively, as acoustic transmissions such that the objects can be transmitting one or more elements of the physical status information from one or more of the objects as devices via acoustic communication.

For instance, in some implementations, the exemplary operation O21 may include the operation of O2108 for transmitting one or more elements of the physical status information from one or more of the devices via optical communication. An exemplary implementation may include the optical transmitting module 173*bh* of FIG. 12 directing the one or more of the optical transceiver components 156*h* of the communication unit 112 of the status determination system 158 of FIG. 6 receiving optical transmissions from each optical transceiver component 156*h* of FIG. 10 of the communication unit 112 of the objects 12. For example, in some implementations, the transmission D1 from object 1 carrying physical status information regarding object 1 and the transmission D2 from object 2 carrying physical status information about object 2 to the status determination system 158, as shown in FIG. 14, can be sent and received by the optical transceiver components 156*h* of the objects 12 and the status determination system 158, respectively, as optical transmissions such that the objects can be transmitting one or more elements of the physical status information from one or more of the objects as devices via a optical communication.

FIG. 32

Figure 32:
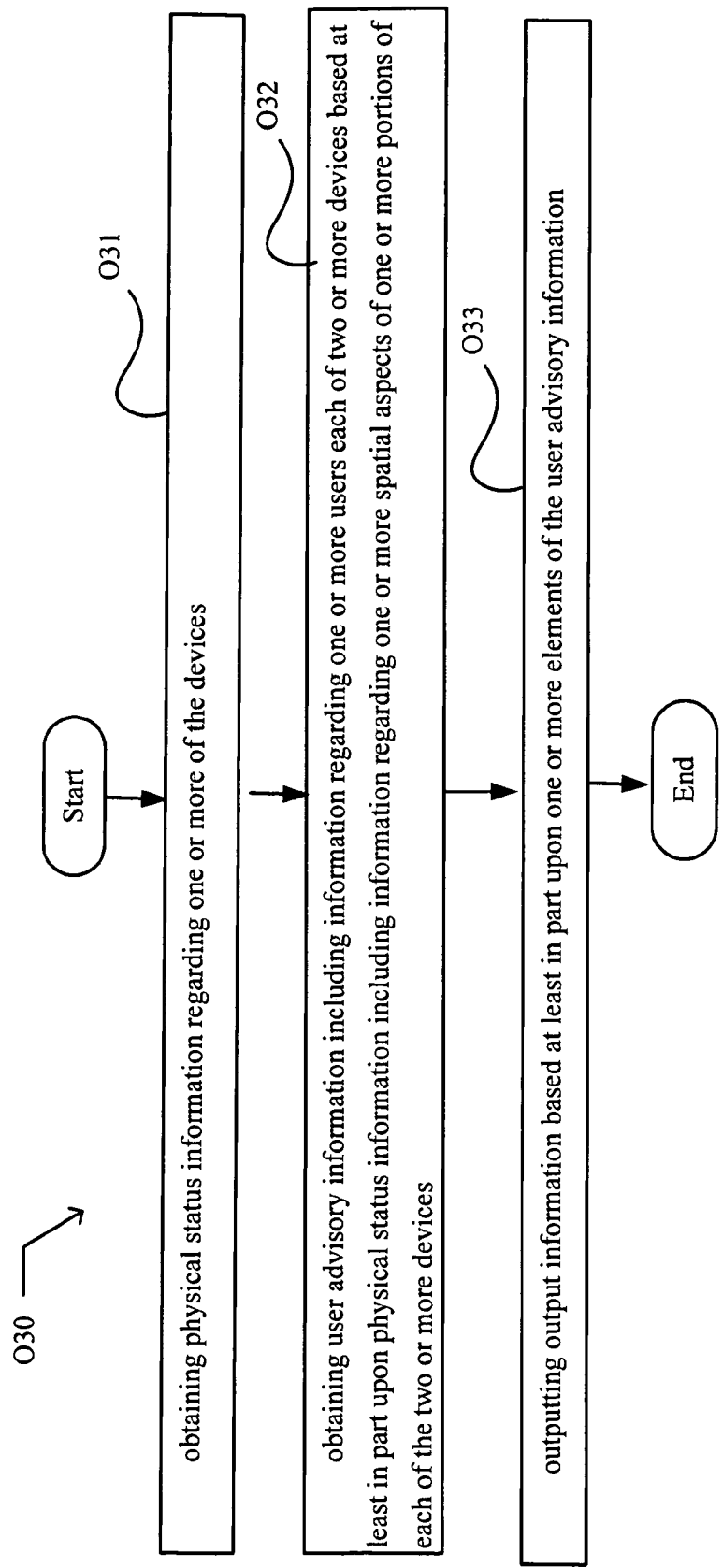
FIG. 32 is a high-level flowchart illustrating an operational flow O30 representing exemplary operations related to obtaining physical status information regarding one or more of the devices, obtaining user advisory information including information regarding one or more users each of two or more devices based at least in part upon physical status information including information regarding one or more spatial aspects of one or more portions of each of the two or more devices, and outputting output information based at least in part upon one or more elements of the user advisory information at least associated with the depicted exemplary implementations of the postural information system.

In FIG. 32 and those figures that follow, various operations may be depicted in a box-within-a-box manner. Such depictions may indicate that an operation in an internal box may comprise an optional exemplary implementation of the operational step illustrated in one or more external boxes. However, it should be understood that internal box operations may be viewed as independent operations separate from any associated external boxes and may be performed in any sequence with respect to all other illustrated operations, or may be performed concurrently.

After a start operation, the operational flow O30 may move to an operation O31, where obtaining physical status information regarding one or more of the devices may be executed by the communication unit 112 of the objects 12 of FIG. 10. An exemplary implementation can include the obtaining physical module 173*bi* of FIG. 12 directing the one or more components of the sensing unit 110 of the status determination system 158 of FIG. 6 detecting one or more spatial aspects of one or more portions of one or more of the objects 12, which can be devices. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, the sensing unit 110 of the status determination system 158 can be used to detect spatial aspects, such as position, location, orientation, visual placement, visual appearance, and/or conformation of the objects 12. The status communication unit 112 of the status determination system 158 can then send the detected spatial aspects to the communication unit 112 of the objects 102, such as shown in FIG. 16, such that the objects can be configured for receiving one or more spatial aspects of one or more portions of one or more of the devices.

The operational flow O30 may then move to operation O32, where obtaining user advisory information including information regarding one or more users each of two or more devices based at least in part upon physical status information including information regarding one or more spatial aspects of one or more portions of each of the two or more devices may be, executed by, for example, the obtaining information module 173*a* of FIG. 11 directing the communication unit 112 of the object 12 of FIG. 10 to receive through one or more of the transceiver components 156 user advisory information (e.g. including M1 and M2 as depicted in FIG. 14 and in FIG. 15) from the advisory system 118 of FIG. 3. In implementations the user advisory information can include information regarding one or more users each of two or more devices based at least in part upon physical status information including information regarding one or more spatial aspects of one or more portions of each of the two or more devices (e.g. S1 and S2 depicted as being sent from the objects 12 in FIG. 15).

The operational flow O30 may then move to operation O33, where outputting output information based at least in part upon one or more elements of the user advisory information may be executed by, the advisory output 104 of FIG. 1. An exemplary implementation may include the output module 173*b* of FIG. 11 directing the advisory output 104 to receive information containing advisory based content from the advisory system 118 either externally (such as "M" depicted in FIG. 14) and internally (such as from the advisory resource 102 to the advisory output within the advisory system, for instance, shown in FIG. 14). After receiving the information containing advisory based content, the output module 173*b* of FIG. 11 can direct the advisory output 104 to output information (e.g. A1 and A2 of FIG. 14 and FIG. 15) based at least in part upon one or more elements of the user advisory information.

FIG. 33

Figure 33:
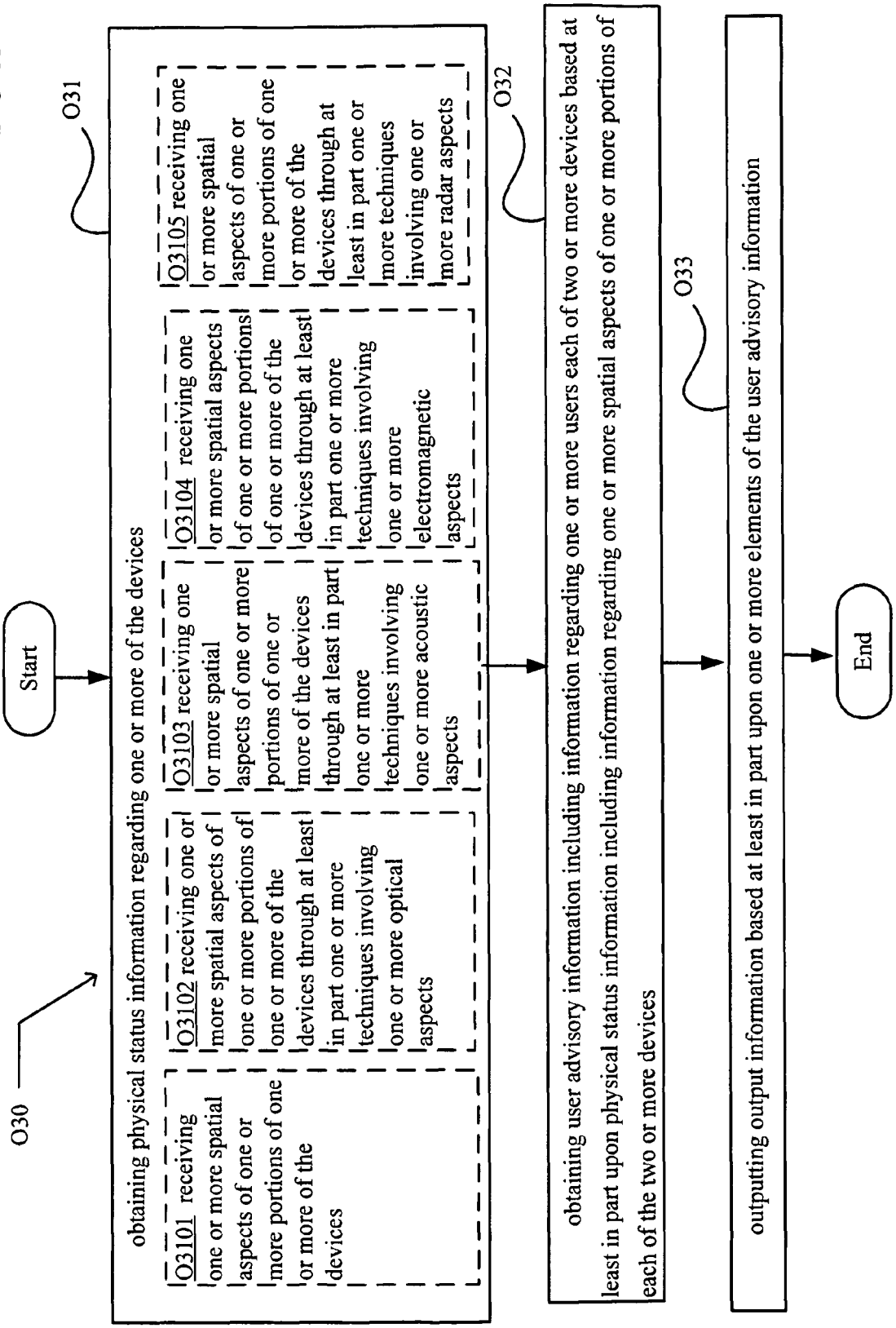
FIG. 33 is a high-level flowchart including exemplary implementations of operation O31 of FIG. 32.

FIG. 33 illustrates various implementations of the exemplary operation O31 of FIG. 32. In particular, FIG. 33 illustrates example implementations where the operation O31 includes one or more additional operations including, for example, operations O3101, O3102, O3103, O3104, and/or O3105, which may be executed generally by, in some instances, In particular, one or more sensing components of the sensing unit 110 of the status determination system 158 of FIG. 6.

For instance, in some implementations, the exemplary operation O31 may include the operation of O3101 for receiving one or more spatial aspects of one or more portions of one or more of the devices. An exemplary implementation can include the receiving spatial module 173*bj* of FIG. 12 directing the one or more components of the sensing unit 110 of the status determination system 158 of FIG. 6 to detect one or more spatial aspects of one or more portions of one or more of the objects 12, which can be devices. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, the sensing unit 110 of the status determination system 158 can be used to detect spatial aspects, such as position, location, orientation, visual placement, visual appearance, and/or conformation of the objects 12. The status communication unit 112 of the status determination system 158 can then send the detected spatial aspects to the communication unit 112 of the objects 102, such as shown in FIG. 16, such that the receiving spatial module 173*bj* can direct the objects to receive one or more spatial aspects of one or more portions of one or more of the devices.

For instance, in some implementations, the exemplary operation O31 may include the operation of O3102 for receiving one or more spatial aspects of one or more portions of one or more of the devices through at least in part one or more techniques involving one or more optical aspects. An exemplary implementation may include the optical transmitting module 173*bh* of FIG. 12 directing the one or more of the optical based sensing components 110*b* of the sensing unit 110 of the status determination system 158 of FIG. 6 to detect one or more spatial aspects of one or more portions of one or more of the objects 12, which can be devices, through at least in part one or more techniques involving one or more optical aspects. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, one or more of the optical based sensing components 110*b* of the status determination system 158 can be used to detect spatial aspects, such as position, location, orientation, visual placement, visual appearance, and/or conformation of the objects 12. The status communication unit 112 of the status determination system 158 can then send the detected spatial aspects to the communication unit 112 of the objects 102, such as shown in FIG. 16, such that the optical transmitting module 173*bh* can direct receiving one or more spatial aspects of one or more portions of one or more of the devices through at least in part one or more techniques involving one or more optical aspects.

For instance, in some implementations, the exemplary operation O31 may include the operation of O3103 for receiving one or more spatial aspects of one or more portions of one or more of the devices through at least in part one or more techniques involving one or more acoustic aspects. An exemplary implementation may include the receiving acoustic module 173*bk* of FIG. 12 directing one or more of the acoustic based sensing components 110*i* of the sensing unit 110 of the status determination system 158 of FIG. 6 to detect one or more spatial aspects of one or more portions of one or more of the objects 12, which can be devices, through at least in part one or more techniques involving one or more acoustic aspects. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, one or more of the acoustic based sensing components 110*i* of the status determination system 158 can be used to detect spatial aspects, such as position, location, orientation, visual placement, visual appearance, and/or conformation of the objects 12. The status communication unit 112 of the status determination system 158 can then send the detected spatial aspects to the communication unit 112 of the objects 102, such as shown in FIG. 15, such that the receiving acoustic module 173*bk* of FIG. 12 can direct objects as devices for receiving one or more spatial aspects of one or more portions of one or more of the devices through at least in part one or more techniques involving one or more acoustic aspects.

For instance, in some implementations, the exemplary operation O31 may include the operation of O3104 for receiving one or more spatial aspects of one or more portions of one or more of the devices through at least in part one or more techniques involving one or more electromagnetic aspects. An exemplary implementation may include the receiving EM module 173*bl* of FIG. 12 directing one or more of the electromagnetic based sensing components 110*g* of the sensing unit 110 of the status determination system 158 of FIG. 6 to detect one or more spatial aspects of one or more portions of one or more of the objects 12, which can be devices, through at least in part one or more techniques involving one or more electromagnetic aspects. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, one or more of the electromagnetic based sensing components 110*g* of the status determination system 158 can be used to detect spatial aspects, such as position, location, orientation, visual placement, visual appearance, and/or conformation of the objects 12. The status communication unit 112 of the status determination system 158 can then send the detected spatial aspects to the communication unit 112 of the objects 102, such as shown in FIG. 15, such that the receiving EM module 173*bl* of FIG. 12 can direct objects as devices for receiving one or more spatial aspects of one or more portions of one or more of the devices through at least in part one or more techniques involving one or more electromagnetic aspects.

For instance, in some implementations, the exemplary operation O31 may include the operation of O3105 for receiving one or more spatial aspects of one or more portions of one or more of the devices through at least in part one or more techniques involving one or more radar aspects. An exemplary implementation may include the receiving radar module 173*bm* of FIG. 7 directing one or more of the radar based sensing components 110*k* of the sensing unit 110 of the status determination system 158 of FIG. 6 to detect one or more spatial aspects of one or more portions of one or more of the objects 12, which can be devices, through at least in part one or more techniques involving one or more radar aspects. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, one or more of the radar based sensing components 110*k* of the status determination system 158 can be used to detect spatial aspects, such as position, location, orientation, visual placement, visual appearance, and/or conformation of the objects 12. The status communication unit 112 of the status determination system 158 can then send the detected spatial aspects to the communication unit 112 of the objects 102, such as shown in FIG. 15, such that the receiving radar module 173*bm* of FIG. 12 can direct objects as devices for receiving one or more spatial aspects of one or more portions of one or more of the devices through at least in part one or more techniques involving one or more radar aspects.

FIG. 34

Figure 34:
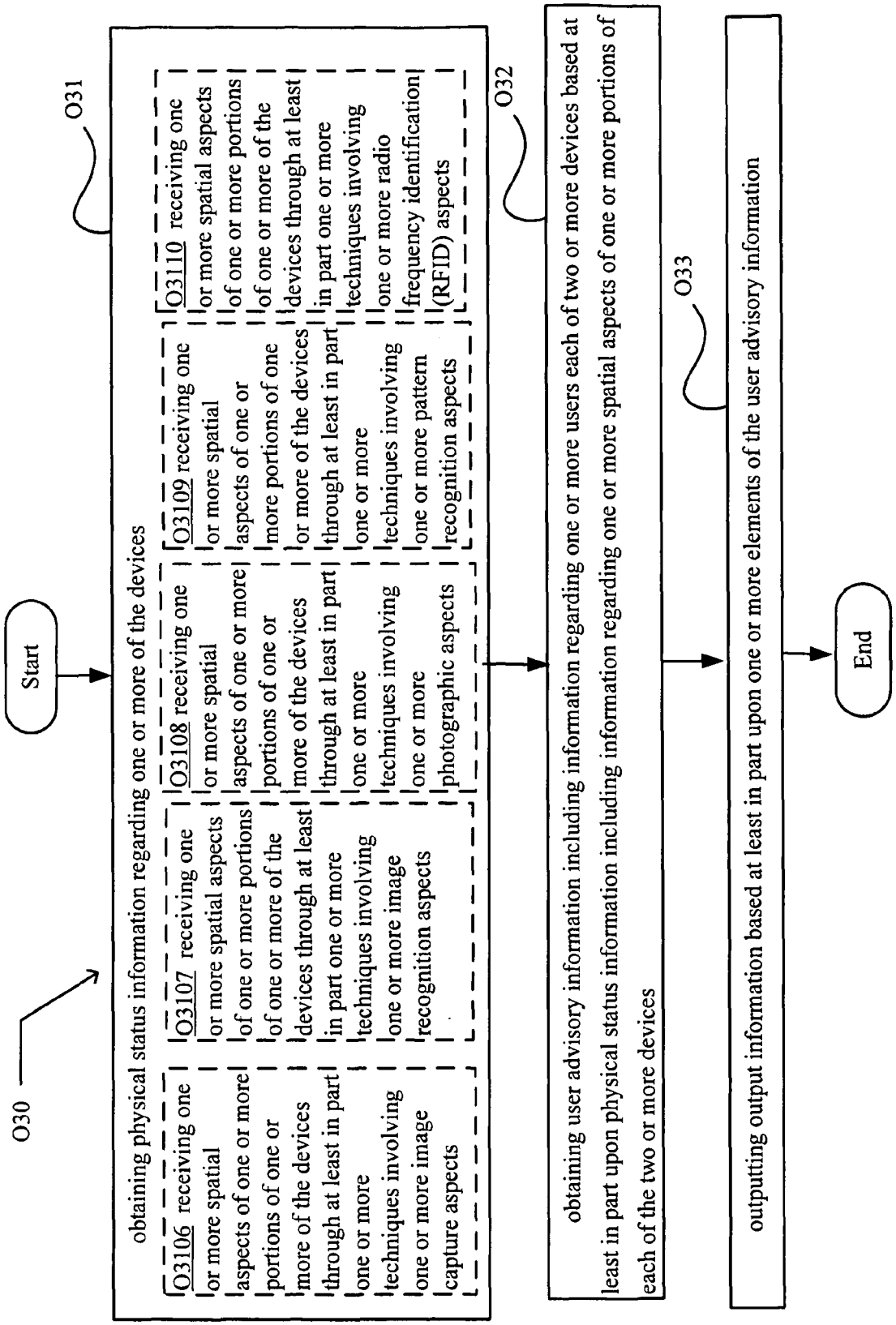
FIG. 34 is a high-level flowchart including exemplary implementations of operation O31 of FIG. 32.

FIG. 34 illustrates various implementations of the exemplary operation O31 of FIG. 32. In particular, FIG. 34 illustrates example implementations where the operation O31 includes one or more additional operations including, for example, operations O3106, O3107, O3108, O3109, and/or O3110, which may be executed generally by, in some instances, In particular, one or more sensing components of the sensing unit 110 of the status determination system 158 of FIG. 6.

For instance, in some implementations, the exemplary operation O31 may include the operation of O3106 for receiving one or more spatial aspects of one or more portions of one or more of the devices through at least in part one or more techniques involving one or more image capture aspects. An exemplary implementation may include receiving image capture module 173*bn* directing one or more of the image capture based sensing components 110*m* of the sensing unit 110 of the status determination system 158 of FIG. 6 to detect one or more spatial aspects of one or more portions of one or more of the objects 12, which can be devices, through at least in part one or more techniques involving one or more image capture aspects. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, one or more of the image capture based sensing components 110*m* of the status determination system 158 can be used to detect spatial aspects, such as position, location, orientation, visual placement, visual appearance, and/or conformation of the objects 12. The status communication unit 112 of the status determination system 158 can then send the detected spatial aspects to the communication unit 112 of the objects 102, such as shown in FIG. 15, such that the receiving image capture module 173*bn* can direct objects as devices for receiving one or more spatial aspects of one or more portions of one or more of the devices through at least in part one or more techniques involving one or more image capture aspects.

For instance, in some implementations, the exemplary operation O31 may include the operation of O3107 for receiving one or more spatial aspects of one or more portions of one or more of the devices through at least in part one or more techniques involving one or more image recognition aspects. An exemplary implementation may include the image recognition receiving module 173*bo* of FIG. 12 directing one or more of the image recognition based sensing components 110*l* of the sensing unit 110 of the status determination system 158 of FIG. 6 to detect one or more spatial aspects of one or more portions of one or more of the objects 12, which can be devices, through at least in part one or more techniques involving one or more image recognition aspects. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, one or more of the image recognition based sensing components 110*l* of the status determination system 158 can be used to detect spatial aspects, such as position, location, orientation, visual placement, visual appearance, and/or conformation of the objects 12. The status communication unit 112 of the status determination system 158 can then send the detected spatial aspects to the communication unit 112 of the objects 102, such as shown in FIG. 15, such that the image recognition receiving module 173*bo* of FIG. 12 con direct the objects as devices for receiving one or more spatial aspects of one or more portions of one or more of the devices through at least in part one or more techniques involving one or more image recognition aspects.

For instance, in some implementations, the exemplary operation O31 may include the operation of O3108 for receiving one or more spatial aspects of one or more portions of one or more of the devices through at least in part one or more techniques involving one or more photographic aspects. An exemplary implementation may include the photographic receiving module 173*bp* of FIG. 12 directing one or more of the photographic based sensing components 110*n* of the sensing unit 110 of the status determination system 158 of FIG. 6 to detect one or more spatial aspects of one or more portions of one or more of the objects 12, which can be devices, through at least in part one or more techniques involving one or more photographic aspects. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, one or more of the photographic based sensing components 110*k* of the status determination system 158 can be used to detect spatial aspects, such as position, location, orientation, visual placement, visual appearance, and/or conformation of the objects 12. The status communication unit 112 of the status determination system 158 can then send the detected spatial aspects to the communication unit 112 of the objects 102, such as shown in FIG. 15, such that the photographic receiving module 173*bp* of FIG. 12 can direct the objects as devices for receiving one or more spatial aspects of one or more portions of one or more of the devices through at least in part one or more techniques involving one or more photographic aspects.

For instance, in some implementations, the exemplary operation O31 may include the operation of O3109 for receiving one or more spatial aspects of one or more portions of one or more of the devices through at least in part one or more techniques involving one or more pattern recognition aspects. An exemplary implementation may include the pattern recognition receiving module 173*bq* of FIG. 12 directing one or more of the pattern recognition based sensing components 110*e* of the sensing unit 110 of the status determination system 158 of FIG. 6 to detect one or more spatial aspects of one or more portions of one or more of the objects 12, which can be devices, through at least in part one or more techniques involving one or more pattern recognition aspects. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, one or more of the pattern recognition based sensing components 110*k* of the status determination system 158 can be used to detect spatial aspects, such as position, location, orientation, visual placement, visual appearance, and/or conformation of the objects 12. The status communication unit 112 of the status determination system 158 can then send the detected spatial aspects to the communication unit 112 of the objects 102, such as shown in FIG. 15, such that the pattern recognition receiving module 173*bq* of FIG. 12 can direct the objects as devices for receiving one or more spatial aspects of one or more portions of one or more of the devices through at least in part one or more techniques involving one or more pattern recognition aspects.

For instance, in some implementations, the exemplary operation O31 may include the operation of O3110 for receiving one or more spatial aspects of one or more portions of one or more of the devices through at least in part one or more techniques involving one or more radio frequency identification (RFID) aspects. An exemplary implementation may include the RFID receiving module 173*br* of FIG. 12 directing the one or more of the RFID based sensing components 110*j* of the sensing unit 110 of the status determination system 158 of FIG. 6 detecting one or more spatial aspects of one or more portions of one or more of the objects 12, which can be devices, through at least in part one or more techniques involving one or more RFID aspects. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, one or more of the RFID based sensing components 110*k* of the status determination system 158 can be used to detect spatial aspects, such as position, location, orientation, visual placement, visual appearance, and/or conformation of the objects 12. The status communication unit 112 of the status determination system 158 can then send the detected spatial aspects to the communication unit 112 of the objects 102, such as shown in FIG. 15, such that the RFID receiving module 173*br* of FIG. 12 can direct the objects as devices for receiving one or more spatial aspects of one or more portions of one or more of the devices through at least in part one or more techniques involving one or more radio frequency identification (RFID) aspects.

FIG. 35

Figure 35:
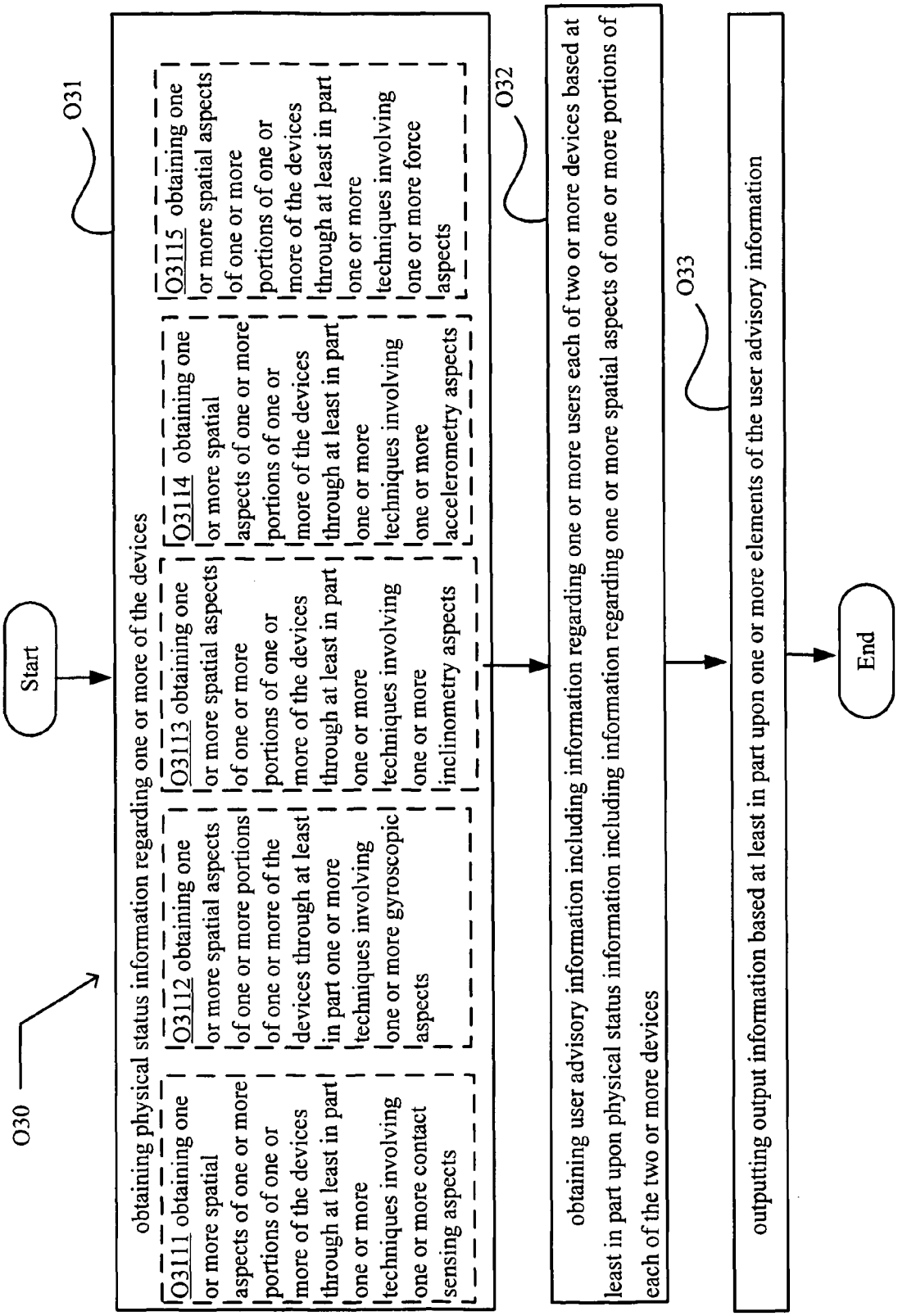
FIG. 35 is a high-level flowchart including exemplary implementations of operation O31 of FIG. 32.

FIG. 35 illustrates various implementations of the exemplary operation O31 of FIG. 32. In particular, FIG. 35 illustrates example implementations where the operation O31 includes one or more additional operations including, for example, operations O3111, O3112, O3113, O3114, and/or O3115, which may be executed generally by, in some instances, one or more of the sensors 108 of the object 12 of FIG. 10 or one or more sensing components of the sensing unit 110 of the status determination system 158 of FIG. 6.

For instance, in some implementations, the exemplary operation O31 may include the operation of O3111 for obtaining one or more spatial aspects of one or more portions of one or more of the devices through at least in part one or more techniques involving one or more contact sensing aspects. An exemplary implementation may include the contact receiving module 173*bs* of FIG. 12 directing one or more of the contact sensors 108*l* of the object 12 shown in FIG. 10 to sense contact such as contact made with the object by the subject 10, such as the user touching a keyboard device as shown in FIG. 2 to detect one or more spatial aspects of one or more portions of the object as a device. For instance, by sensing contact of the subject 10 (user) of the object 12 (device), aspects of the orientation of the device with respect to the user may be detected. such that the contact receiving module 173*bs* of FIG. 12 can direct the objects as devices for obtaining one or more spatial aspects of one or more portions of one or more of the devices through at least in part one or more techniques involving one or more contact sensing aspects.

For instance, in some implementations, the exemplary operation O31 may include the operation of O3112 for obtaining one or more spatial aspects of one or more portions of one or more of the devices through at least in part one or more techniques involving one or more gyroscopic aspects. An exemplary implementation may include the gyroscopic receiving module 173*bt* of FIG. 12 directing one or more of the gyroscopic sensors 108*f* of the object 12 (e.g. object can be a device) shown in FIG. 10 to detect one or more spatial aspects of the one or more portions of the device such that the gyroscopic receiving module 173*bt* of FIG. 12 can direct the objects as devices for obtaining one or more spatial aspects of one or more portions of one or more of the devices through at least in part one or more techniques involving one or more gyroscopic aspects. Spatial aspects can include orientation visual placement, visual appearance, and/or conformation of the objects 12 involved and can be sent to the status determination system 158 as transmissions D1 and D2 by the objects as shown in FIG. 14.

For instance, in some implementations, the exemplary operation O31 may include the operation of O3113 for obtaining one or more spatial aspects of one or more portions of one or more of the devices through at least in part one or more techniques involving one or more inclinometry aspects. An exemplary implementation may include the inclinometry receiving module 173*bu* of FIG. 12 directing one or more of the inclinometers 108*i* of the object 12 (e.g. object can be a device) shown in FIG. 10 to detect one or more spatial aspects of the one or more portions of the device such that the inclinometry receiving module 173*bu* of FIG. 12 can direct objects as devices for obtaining one or more spatial aspects of one or more portions of one or more of the devices through at least in part one or more techniques involving one or more inclinometry aspects. Spatial aspects can include orientation visual placement, visual appearance, and/or conformation of the objects 12 involved and can be sent to the status determination system 158 as transmissions D1 and D2 by the objects as shown in FIG. 14.

For instance, in some implementations, the exemplary operation O31 may include the operation of O3114 for obtaining one or more spatial aspects of one or more portions of one or more of the devices through at least in part one or more techniques involving one or more accelerometry aspects. An exemplary implementation may include the accelerometry receiving module 173*bv* of FIG. 12 directing one or more of the accelerometers 108*j* of the object 12 (e.g. object can be a device) shown in FIG. 10 to detect one or more spatial aspects of the one or more portions of the device such that the accelerometry receiving module 173*bv* of FIG. 12 can direct the objects as devices for obtaining one or more spatial aspects of one or more portions of one or more of the devices through at least in part one or more techniques involving one or more accelerometry aspects. Spatial aspects can include orientation visual placement, visual appearance, and/or conformation of the objects 12 involved and can be sent to the status determination system 158 as transmissions D1 and D2 by the objects as shown in FIG. 14.

For instance, in some implementations, the exemplary operation O31 may include the operation of O3115 for obtaining one or more spatial aspects of one or more portions of one or more of the devices through at least in part one or more techniques involving one or more force aspects. An exemplary implementation may include the force receiving module 173*bw* of FIG. 12 directing one or more of the force sensors 108*e* of the object 12 (e.g. object can be a device) shown in FIG. 10 detecting one or more spatial aspects of the one or more portions of the device such that the force receiving module 173*bw* of FIG. 12 can direct the objects as devices for obtaining one or more spatial aspects of one or more portions of one or more of the devices through at least in part one or more techniques involving one or more force aspects. Spatial aspects can include orientation visual placement, visual appearance, and/or conformation of the objects 12 involved and can be sent to the status determination system 158 as transmissions D1 and D2 by the objects as shown in FIG. 14.

FIG. 36

Figure 36:
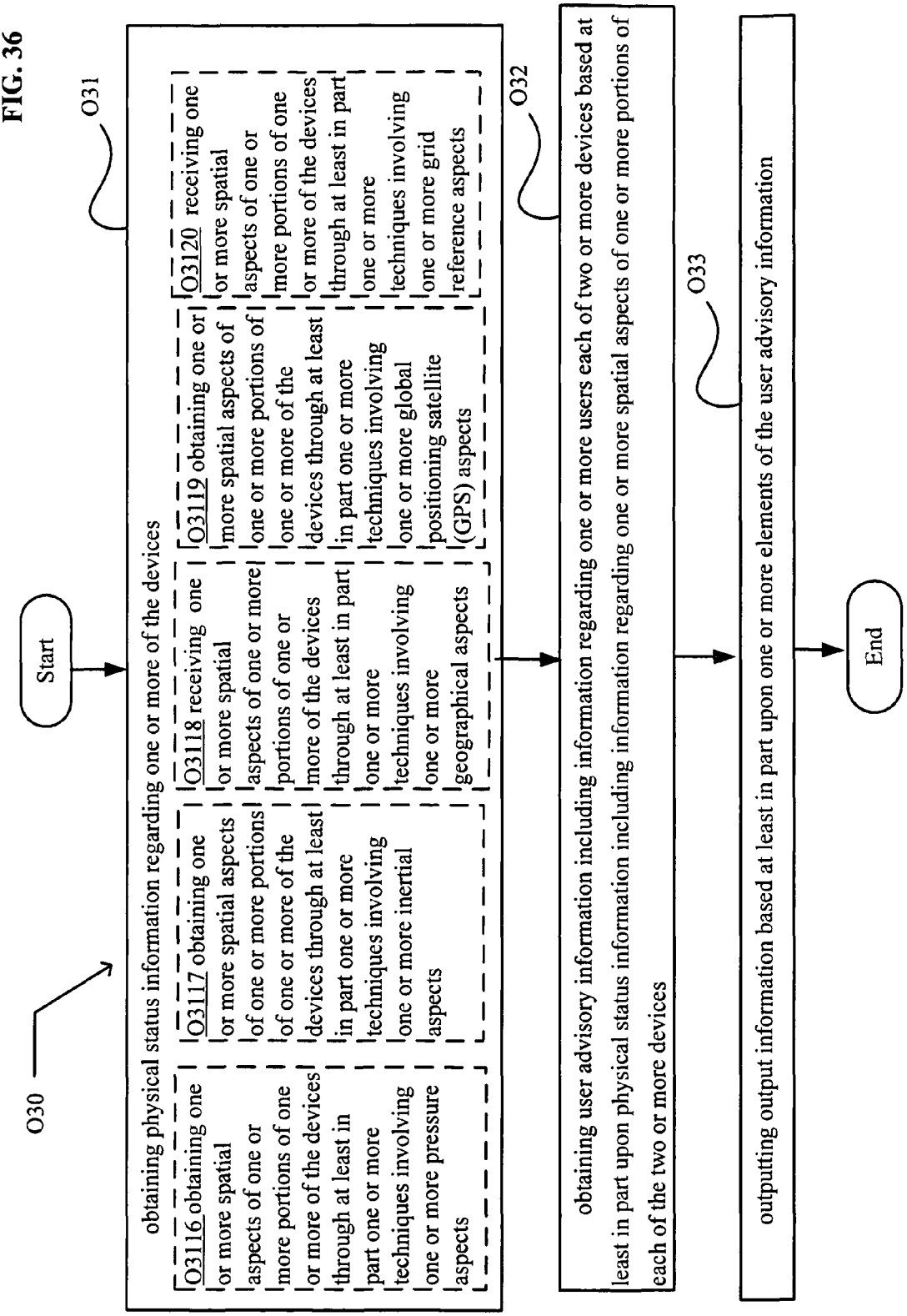
FIG. 36 is a high-level flowchart including exemplary implementations of operation O31 of FIG. 32.

FIG. 36 illustrates various implementations of the exemplary operation O31 of FIG. 32. In particular, FIG. 36 illustrates example implementations where the operation O33 includes one or more additional operations including, for example, operations O3116, O3117, O3118, O3119, and/or O3120, which may be executed generally by, in some instances, one or more of the sensors 108 of the object 12 of FIG. 10.

For instance, in some implementations, the exemplary operation O31 may include the operation of O3116 for obtaining one or more spatial aspects of one or more portions of one or more of the devices through at least in part one or more techniques involving one or more pressure aspects An exemplary implementation may include the pressure receiving module 173*bx* of FIG. 12 directing one or more of the pressure sensors 108*m* of the object 12 (e.g. object can be a device) shown in FIG. 10 to detect one or more spatial aspects of the one or more portions of the device such that the pressure receiving module 173*bx* of FIG. 12 can direct the objects as devices for obtaining one or more spatial aspects of one or more portions of one or more of the devices through at least in part one or more techniques involving one or more pressure aspects. Spatial aspects can include orientation visual placement, visual appearance, and/or conformation of the objects 12 involved and can be sent to the status determination system 158 as transmissions D1 and D2 by the objects as shown in FIG. 14.

For instance, in some implementations, the exemplary operation O31 may include the operation of O3117 for obtaining one or more spatial aspects of one or more portions of one or more of the devices through at least in part one or more techniques involving one or more inertial aspects. An exemplary implementation may include the inertial receiving module 173*by* of FIG. 12 directing one or more of the inertial sensors 108*k* of the object 12 (e.g. object can be a device) shown in FIG. 10 to detect one or more spatial aspects of the one or more portions of the device such that the inertial receiving module 173*by* of FIG. 12 can direct the objects as devices for obtaining one or more spatial aspects of one or more portions of one or more of the devices through at least in part one or more techniques involving one or more inertial aspects. Spatial aspects can include orientation visual placement, visual appearance, and/or conformation of the objects 12 involved and can be sent to the status determination system 158 as transmissions D1 and D2 by the objects as shown in FIG. 14.

For instance, in some implementations, the exemplary operation O31 may include the operation of O3118 for receiving one or more spatial aspects of one or more portions of one or more of the devices through at least in part one or more techniques involving one or more geographical aspects. An exemplary implementation may include the geographical receiving module 173*bz* of FIG. 12 directing one or more of the image recognition based sensing components 110*l* of the sensing unit 110 of the status determination system 158 of FIG. 6 to detect one or more spatial aspects of one or more portions of one or more of the objects 12, which can be devices, through at least in part one or more techniques involving one or more geographical aspects. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, one or more of the image recognition based sensing components 110*l* of the status determination system 158 can be used to detect spatial aspects involving geographical aspects, such as position, location, orientation, visual placement, visual appearance, and/or conformation of the objects 12 in relation to a geographical landmark. The status communication unit 112 of the status determination system 158 can then send the detected spatial aspects to the communication unit 112 of the object 102 to allow the object to provide physical status information of the object as a device such as shown in FIG. 15, such that the geographical receiving module 173*bz* of FIG. 12 can direct the objects as devices for receiving one or more spatial aspects of one or more portions of one or more of the devices through at least in part one or more techniques involving one or more geographical aspects.

For instance, in some implementations, the exemplary operation O31 may include the operation of O3119 for obtaining one or more spatial aspects of one or more portions of one or more of the devices through at least in part one or more techniques involving one or more global positioning satellite (GPS) aspects. An exemplary implementation may include the GPS receiving module 173ca of FIG. 12 directing one or more of the global positioning system (GPS) sensors 108g of the object 12 (e.g. object can be a device) shown in FIG. 10 to detect one or more spatial aspects of the one or more portions of the device such that the objects as devices can be configured for obtaining one or more spatial aspects of one or more portions of one or more of the devices through at least in part one or more techniques involving one or more global positioning satellite (GPS) aspects. Spatial aspects can include location and position as provided by the global positioning system (GPS) to the global positioning system (GPS) sensors 108g of the objects 12 involved and can be sent to the status determination system 158 as transmissions D1 and D2 by the objects as shown in FIG. 14.

For instance, in some implementations, the exemplary operation O31 may include the operation of O3120 for receiving one or more spatial aspects of one or more portions of one or more of the devices through at least in part one or more techniques involving one or more grid reference aspects. An exemplary implementation may include the grid reference receiving module 173cb of FIG. 12 directing one or more of the grid reference based sensing components 110o of the sensing unit 110 of the status determination system 158 of FIG. 6 detecting one or more spatial aspects of one or more portions of one or more of the objects 12, which can be devices, through at least in part one or more techniques involving one or more grid reference aspects. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, one or more of the grid reference based sensing components 110o of the status determination system 158 can be used to detect spatial aspects involving grid reference aspects, such as position, location, orientation, visual placement, visual appearance, and/or conformation of the objects 12. such as shown in FIG. 15, such that the grid reference receiving module 173cb of FIG. 12 can direct the objects as devices can be configured for receiving one or more spatial aspects of one or more portions of one or more of the devices through at least in part one or more techniques involving one or more grid reference aspects.

FIG. 37

Figure 37:
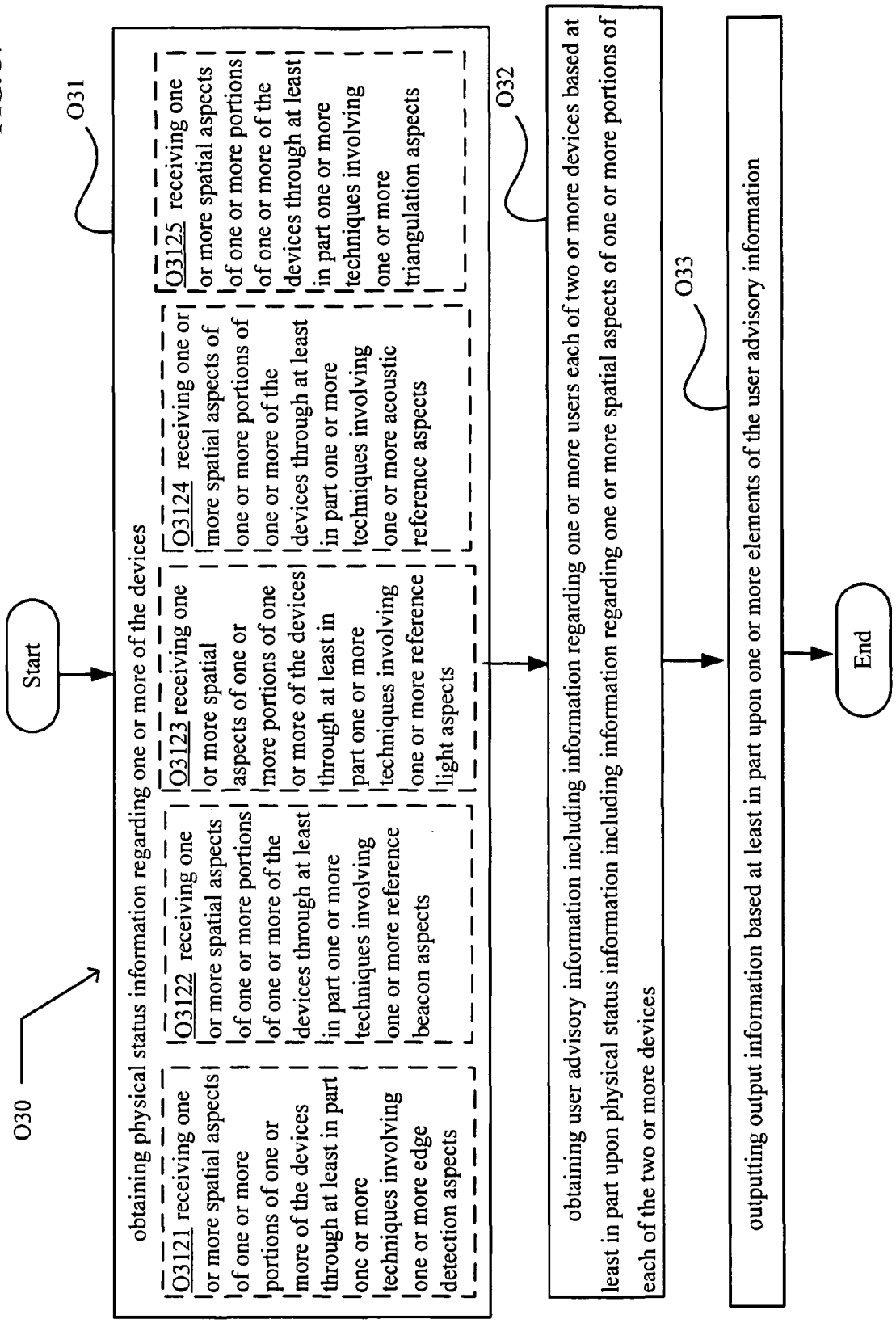
FIG. 37 is a high-level flowchart including exemplary implementations of operation O31 of FIG. 32.

FIG. 37 illustrates various implementations of the exemplary operation O31 of FIG. 32. In particular, FIG. 37 illustrates example implementations where the operation O31 includes one or more additional operations including, for example, operations O3121, O3122, O3123, O3124, and/or O3125, which may be executed generally by, in some instances, one or more of the sensors 108 of the object 12 of FIG. 10 or one or more sensing components of the sensing unit 110 of the status determination system 158 of FIG. 6.

For instance, in some implementations, the exemplary operation O31 may include the operation of O3121 for receiving one or more spatial aspects of one or more portions of one or more of the devices through at least in part one or more techniques involving one or more edge detection aspects. An exemplary implementation may include the edge receiving module 173cc of FIG. 12 directing one or more of the edge detection based sensing components 110p of the sensing unit 110 of the status determination system 158 of FIG. 6 to detect one or more spatial aspects of one or more portions of one or more of the objects 12, which can be devices, through at least in part one or more techniques involving one or more edge detection aspects. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, one or more of the edge detection based sensing components 110p of the status determination system 158 can be used to detect spatial aspects involving edge detection aspects, such as position, location, orientation, visual placement, visual appearance, and/or conformation of the objects 12 such as shown in FIG. 15, such that the edge receiving module 173cc of FIG. 12 can direct the objects as devices for receiving one or more spatial aspects of one or more portions of one or more of the devices through at least in part one or more techniques involving one or more edge detection aspects.

For instance, in some implementations, the exemplary operation O31 may include the operation of O3122 for receiving one or more spatial aspects of one or more portions of one or more of the devices through at least in part one or more techniques involving one or more reference beacon aspects. An exemplary implementation may include the beacon receiving module 173cd directing one or more of the reference beacon based sensing components 110q of the sensing unit 110 of the status determination system 158 of FIG. 6 to detect one or more spatial aspects of one or more portions of one or more of the objects 12, which can be devices, through at least in part one or more techniques involving one or more reference beacon aspects. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, one or more of the reference beacon based sensing components 110q of the status determination system 158 can be used to detect spatial aspects involving reference beacon aspects, such as position, location, orientation, visual placement, visual appearance, and/or conformation of the objects 12, such as shown in FIG. 15, such that the beacon receiving module 173cd of FIG. 12 can direct objects as devices for receiving one or more spatial aspects of one or more portions of one or more of the devices through at least in part one or more techniques involving one or more reference beam aspects.

For instance, in some implementations, the exemplary operation O31 may include the operation of O3123 for receiving one or more spatial aspects of one or more portions of one or more of the devices through at least in part one or more techniques involving one or more reference light aspects. An exemplary implementation may include the reference light receiving module 173ce of FIG. 12 directing one or more of the reference light based sensing components 110r of the sensing unit 110 of the status determination system 158 of FIG. 6 to detect one or more spatial aspects of one or more portions of one or more of the objects 12, which can be devices, through at least in part one or more techniques involving one or more reference light aspects. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, one or more of the reference light based sensing components 110*r* of the status determination system 158 can be used to detect spatial aspects involving reference light aspects, such as position, location, orientation, visual placement, visual appearance, and/or conformation of the objects 12 such as shown in FIG. 15, such that the reference light receiving module 173*ce* of FIG. 12 can direct objects as devices for receiving one or more spatial aspects of one or more portions of one or more of the devices through at least in part one or more techniques involving one or more reference light aspects.

For instance, in some implementations, the exemplary operation O31 may include the operation of O3124 for receiving one or more spatial aspects of one or more portions of one or more of the devices through at least in part one or more techniques involving one or more acoustic reference aspects. An exemplary implementation may include the acoustic reference receiving module 173*cf* of FIG. 12 directing one or more of the acoustic reference based sensing components 110*s* of the sensing unit 110 of the status determination system 158 of FIG. 6 to detect one or more spatial aspects of one or more portions of one or more of the objects 12, which can be devices, through at least in part one or more techniques involving one or more acoustic reference aspects. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, one or more of the acoustic reference based sensing components 110*s* of the status determination system 158 can be used to detect spatial aspects involving acoustic reference aspects, such as position, location, orientation, visual placement, visual appearance, and/or conformation of the objects 12, such as shown in FIG. 15, such that the acoustic reference receiving module 173*cf* of FIG. 12 can direct the objects as devices for receiving one or more spatial aspects of one or more portions of one or more of the devices through at least in part one or more techniques involving one or more acoustic reference aspects.

For instance, in some implementations, the exemplary operation O31 may include the operation of O3125 for receiving one or more spatial aspects of one or more portions of one or more of the devices through at least in part one or more techniques involving one or more triangulation aspects. An exemplary implementation may include the triangulation receiving module 173*cg* of FIG. 12 directing one or more of the triangulation based sensing components 110*t* of the sensing unit 110 of the status determination system 158 of FIG. 6 to detect one or more spatial aspects of one or more portions of one or more of the objects 12, which can be devices, through at least in part one or more techniques involving one or more triangulation aspects. For example, in some implementations, the transmission D1 from object 1 carrying physical status information regarding object 1 and the transmission D2 from object 2 carrying physical status information about object 2 to the status determination system 158, as shown in FIG. 14, will not be present in situations in which the sensors 108 of the object 1 and object 2 are either not present or not being used. Consequently, in cases when the object sensors are not present or are otherwise not used, one or more of the triangulation based sensing components 110*t* of the status determination system 158 can be used to detect spatial aspects involving triangulation aspects, such as position, location, orientation, visual placement, visual appearance, and/or conformation of the objects 12, such as shown in FIG. 15, such that the triangulation receiving module 173*cg* of FIG. 12 can direct the objects as devices for receiving one or more spatial aspects of one or more portions of one or more of the devices through at least in part one or more techniques involving one or more triangulation aspects.

FIG. 38

Figure 38:
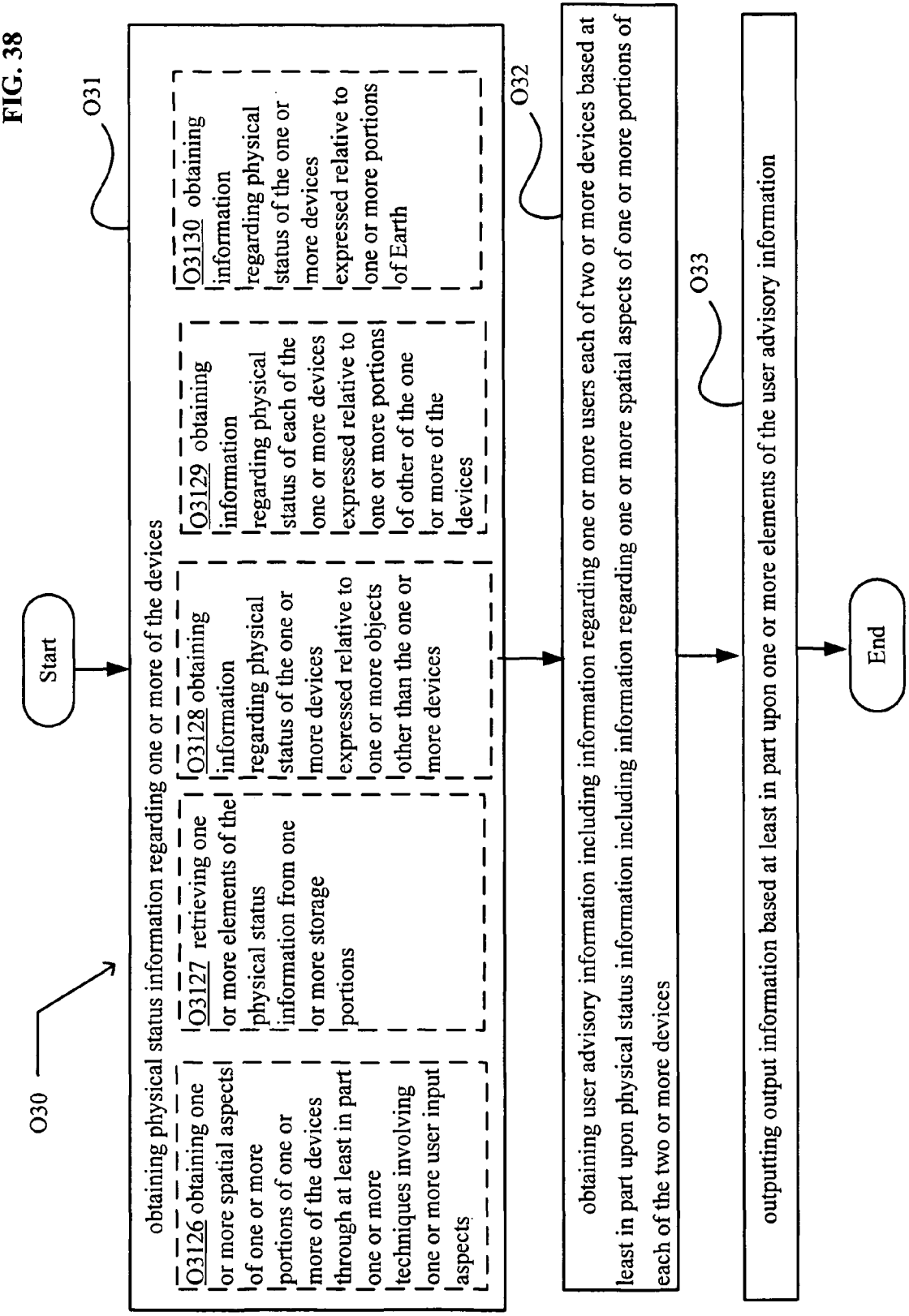
FIG. 38 is a high-level flowchart including exemplary implementations of operation O31 of FIG. 32.

FIG. 38 illustrates various implementations of the exemplary operation O31 of FIG. 32. In particular, FIG. 38 illustrates example implementations where the operation O31 includes one or more additional operations including, for example, operation O3126, O3127, O3128, O3129, and/or O3130, which may be executed generally by, in some instances, one or more of the sensors 108 of the object 12 of FIG. 10 or one or more sensing components of the sensing unit 110 of the status determination system 158 of FIG. 6.

For instance, in some implementations, the exemplary operation O31 may include the operation of O3126 for obtaining one or more spatial aspects of one or more portions of one or more of the devices through at least in part one or more techniques involving one or more user input aspects. An exemplary implementation may include the user input module 173*ch* of FIG. 12 directing the user input aspects as detected by one or more of the contact sensors 108*l* of the object 12 shown in FIG. 10 sensing contact such as contact made with the object by the subject 10, such as the user touching a keyboard device as shown in FIG. 2 to detect one or more spatial aspects of one or more portions of the object as a device. For instance, by sensing contact by the subject 10 (user) as user input of the object 12 (device), aspects of the orientation of the device with respect to the user may be detected such that the user input module 173*ch* of FIG. 12 can direct the objects as devices for obtaining one or more spatial aspects of one or more portions of one or more of the devices through at least in part one or more techniques involving one or more user input aspects.

For instance, in some implementations, the exemplary operation O31 may include the operation of O3127 for retrieving one or more elements of the physical status information from one or more storage portions. An exemplary implementation may include the status retrieving module 173*cj* of FIG. 13 directing the control unit 146 of the object 12 of FIG. 10 to retrieve one or more elements of physical status information, such as dimensional aspects of one or more of the objects from one or more storage portions, such as the storage unit 108*o* of the sensors 108 of the objects, as part of obtaining physical status information regarding one or more portions of the objects 12 as devices such that the status retrieving module 173*cj* of FIG. 13 can direct the objects as devices can for retrieving one or more elements of the physical status information from one or more storage portions.

For instance, in some implementations, the exemplary operation O31 may include the operation of O3128 for obtaining information regarding physical status of the one or more devices expressed relative to one or more objects other than the one or more devices. An exemplary implementation may include the object relative obtaining module 173*ck* of FIG. 13 directing one or more of the sensors 108 of the objects 12 of FIG. 10 to obtain information regarding physical status of the one or more objects as devices expressed relative to one or more objects other than the one or more objects as devices.

For instance, in some implementations the obtained information can be related to positional or other spatial aspects of the objects 12 as related to one or more of the other objects 14 (such as structural members of a building, artwork, furniture, or other objects) that are not being used by the subject 10 or are otherwise not involved with influencing the subject regarding physical status of the subject, such as posture. For instance, the spatial information obtained can be expressed in terms of distances between the objects 12 and the other objects 14.

For instance, in some implementations, the exemplary operation O31 may include the operation of O3129 for obtaining information regarding physical status of each of the one or more devices expressed relative to one or more portions of other of the one or more of the devices. An exemplary implementation may include the device relative obtaining module 173cl of FIG. 13 directing one or more of the sensors 108 of the objects 12 of FIG. 10 obtaining information regarding physical status of each of the one or more objects as devices expressed relative to one or more of other of the one or more of the objects 12 as devices. For instance, in some implementations the obtained information can be related to positional or other spatial aspects of the objects 12 as devices and the spatial information obtained about the objects as devices can be expressed in terms of distances between the objects as devices rather than expressed in terms of an absolute location for each of the objects as devices.

For instance, in some implementations, the exemplary operation O31 may include the operation of O3130 for obtaining information regarding physical status of the one or more devices expressed relative to one or more portions of Earth. An exemplary implementation may include the earth relative obtaining module 173cm of FIG. 13 directing one or more of the sensors 108 of the objects 12 of FIG. 10 obtaining information regarding physical status of the one or more objects as devices expressed relative to one or more portions of Earth. For instance, in some implementations the obtained information can be expressed relative to global positioning system (GPS) coordinates, geographical features or other aspects, or otherwise expressed relative to one or more portions of Earth.

FIG. 39

Figure 39:
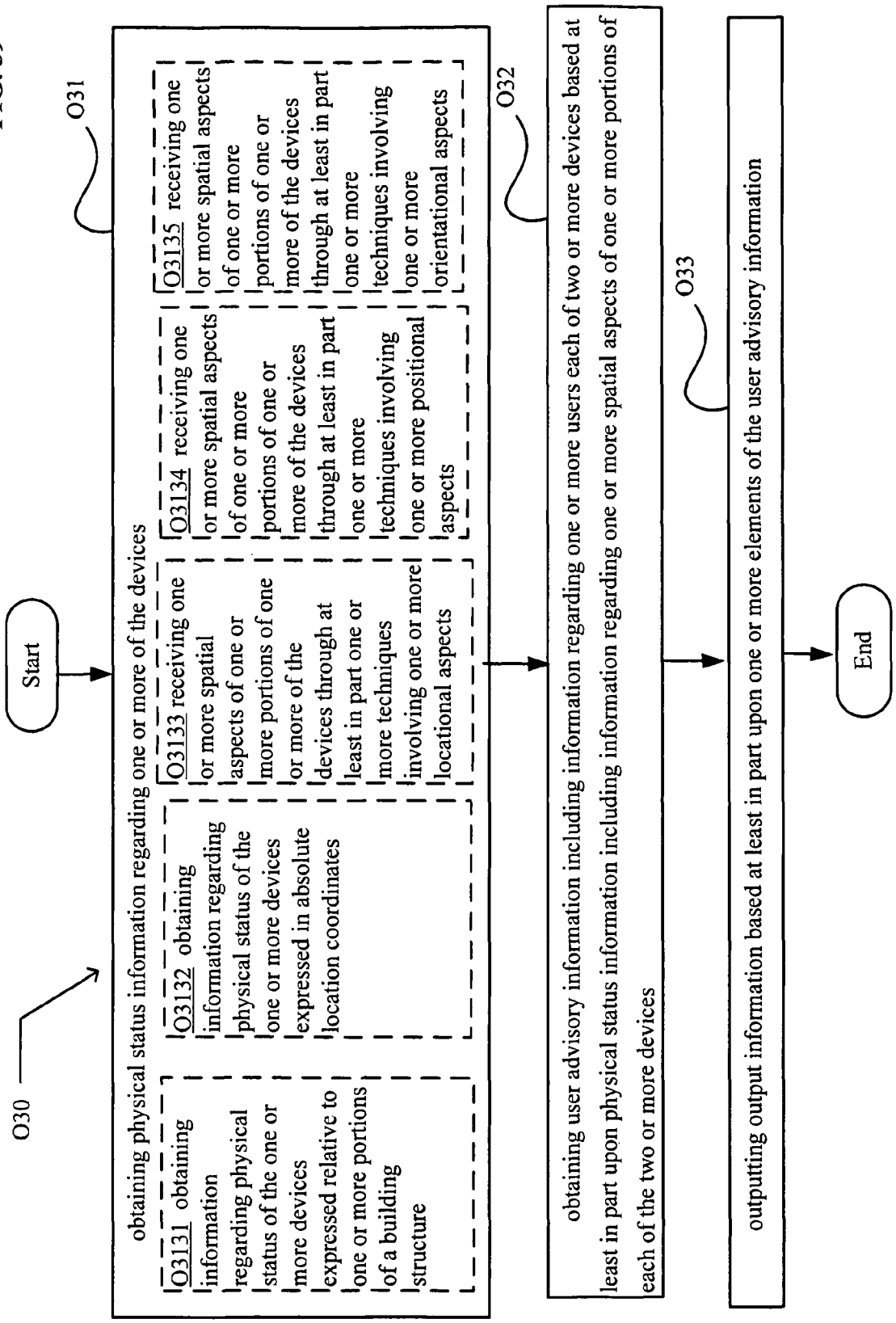
FIG. 39 is a high-level flowchart including exemplary implementations of operation O31 of FIG. 32.

FIG. 39 illustrates various implementations of the exemplary operation O31 of FIG. 32. In particular, FIG. 39 illustrates example implementations where the operation O31 includes one or more additional operations including, for example, operation O3131, O3132, O3133, O3134, and/or O3135, which may be executed generally by, in some instances, one or more of the sensors 108 of the object 12 of FIG. 10 or one or more sensing components of the sensing unit 110 of the status determination system 158 of FIG. 6.

For instance, in some implementations, the exemplary operation O31 may include the operation of O3131 for obtaining information regarding physical status of the one or more devices expressed relative to one or more portions of a building structure. An exemplary implementation may include the building relative obtaining module 173cn of FIG. 13 directing one or more of the sensors 108 of the objects 12 of FIG. 10 as devices obtaining information regarding physical status of the one or more objects as devices expressed relative to one or more portions of a building structure. For instance, in some implementations the obtained information can be expressed relative to one or more portions of a building structure that houses the subject 10 and the objects 12 or is nearby to the subject and the objects.

For instance, in some implementations, the exemplary operation O31 may include the operation of O3132 for obtaining information regarding physical status of the one or more devices expressed in absolute location coordinates. An exemplary implementation may include the locational obtaining module 173co of FIG. 13 directing one or more of the sensors 108 of the objects 12 of FIG. 10 to obtain information regarding physical status of the one or more objects as devices expressed in absolute location coordinates. For instance, in some implementations the obtained information can be expressed in terms of global positioning system (GPS) coordinates.

For instance, in some implementations, the exemplary operation O31 may include the operation of O3133 for obtaining one or more spatial aspects of one or more portions of one or more of the devices through at least in part one or more techniques involving one or more locational aspects. An exemplary implementation may include the locational obtaining module 173cp of FIG. 13 directing one or more of the sensors 108 of the objects 12 of FIG. 10 to obtain one or more spatial aspects of one or more portions of one or more of the objects as devices through at least in part one or more techniques involving one or more locational aspects. For instance, in some implementations the obtained information can be expressed in terms of global positioning system (GPS) coordinates or geographical coordinates.

For instance, in some implementations, the exemplary operation O31 may include the operation of O3134 for obtaining one or more spatial aspects of one or more portions of one or more of the devices through at least in part one or more techniques involving one or more positional aspects. An exemplary implementation may include the positional obtaining module 173cq of FIG. 13 directing one or more of the sensors 108 of the objects 12 of FIG. 10 to obtain one or more spatial aspects of one or more portions of one or more of the objects as devices through at least in part one or more techniques involving one or more positional aspects. For instance, in some implementations the obtained information can be expressed in terms of global positioning system (GPS) coordinates or geographical coordinates.

For instance, in some implementations, the exemplary operation O31 may include the operation of O3135 for obtaining one or more spatial aspects of one or more portions of one or more of the devices through at least in part one or more techniques involving one or more orientational aspects. An exemplary implementation may include the orientational obtaining module 173cr of FIG. 13 directing one or more of the gyroscopic sensors 108f of the objects 12 as a device shown in FIG. 10 obtaining one or more spatial aspects of one or more portions of one or more of the objects as devices through at least in part one or more techniques involving one or more orientational aspects. Spatial aspects can include orientation of the objects 12 involved and can be sent to the status determination system 158 as transmissions D1 and D2 by the objects as shown in FIG. 14.

FIG. 40

Figure 40:
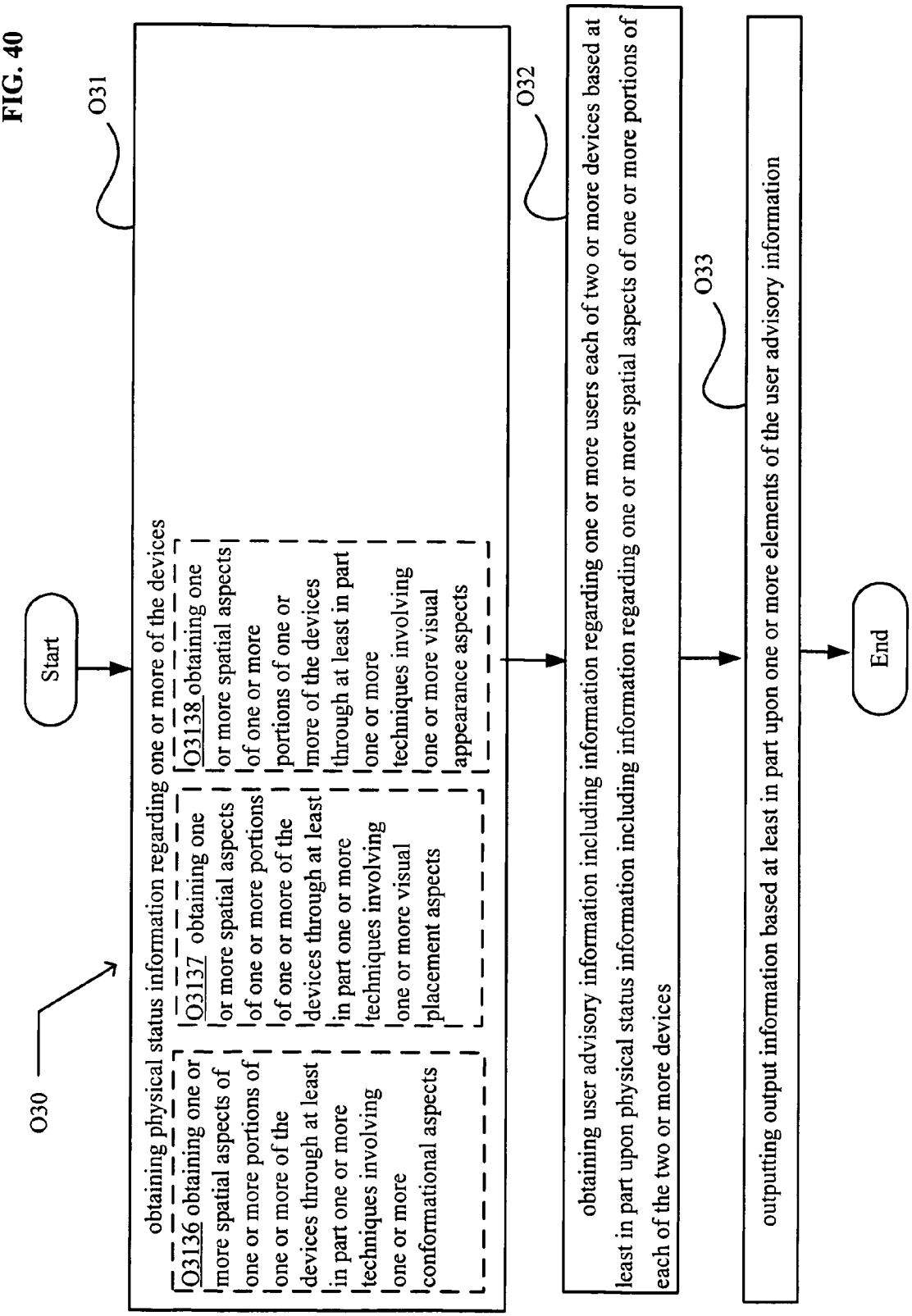
FIG. 40 is a high-level flowchart including exemplary implementations of operation O31 of FIG. 32.

FIG. 40 illustrates various implementations of the exemplary operation O31 of FIG. 32. In particular, FIG. 40 illustrates example implementations where the operation O31 includes one or more additional operations including, for example, operation O3136, O3137, and/or O3138, which may be executed generally by, in some instances, one or more of the sensors 108 of the object 12 of FIG. 10 or one or more sensing components of the sensing unit 110 of the status determination system 158 of FIG. 6.

For instance, in some implementations, the exemplary operation O31 may include the operation of O3136 for obtaining one or more spatial aspects of one or more portions of one or more of the devices through at least in part one or more techniques involving one or more conformational aspects. An exemplary implementation may include the conformational obtaining module 173cs of FIG. 13 directing one or more of the gyroscopic sensors 108f of the objects 12 as devices shown in FIG. 10 obtaining one or more spatial aspects of the one or more portions of the one or more objects as devices through at least in part one or more techniques involving one or more conformational aspects such as folding, bending, twisting, or other structural configuration of the one or more objects. Spatial aspects can include conformation of the objects 12 involved and can be sent to the status determination system 158 as transmissions D1 and D2 by the objects as shown in FIG. 14.

For instance, in some implementations, the exemplary operation O31 may include the operation of O3137 for obtaining one or more spatial aspects of one or more portions of one or more of the devices through at least in part one or more techniques involving one or more visual placement aspects. An exemplary implementation may include the visual placement module 173ct of FIG. 13 directing one or more of the display sensors 108n of the objects as devices shown in FIG. 10, such as the object as a display device shown in FIG. 2, obtaining one or more spatial aspects of one or more portions of one or more of the objects as devices through at least in part one or more techniques involving one or more visual placement aspects, such as placement of display features, such as icons, scene windows, scene widgets, graphic or video content, or other visual features on the object 12 as a display device of FIG. 2.

For instance, in some implementations, the exemplary operation O31 may include the operation of O3138 for obtaining one or more spatial aspects of one or more portions of one or more of the devices through at least in part one or more techniques involving one or more visual appearance aspects. An exemplary implementation may include the visual appearance module 173cu of FIG. 13 directing one or more of the display sensors 108n of the objects 12 as a devices shown in FIG. 10, such as the object as a display device shown in FIG. 2, obtaining one or more spatial aspects of one or more portions of one or more of the objects as devices through at least in part one or more techniques involving one or more visual appearance aspects, such as sizing, of display features, such as icons, scene windows, scene widgets, graphic or video content, or other visual features on the object 12 as a display device of FIG. 2.

Figure 41:
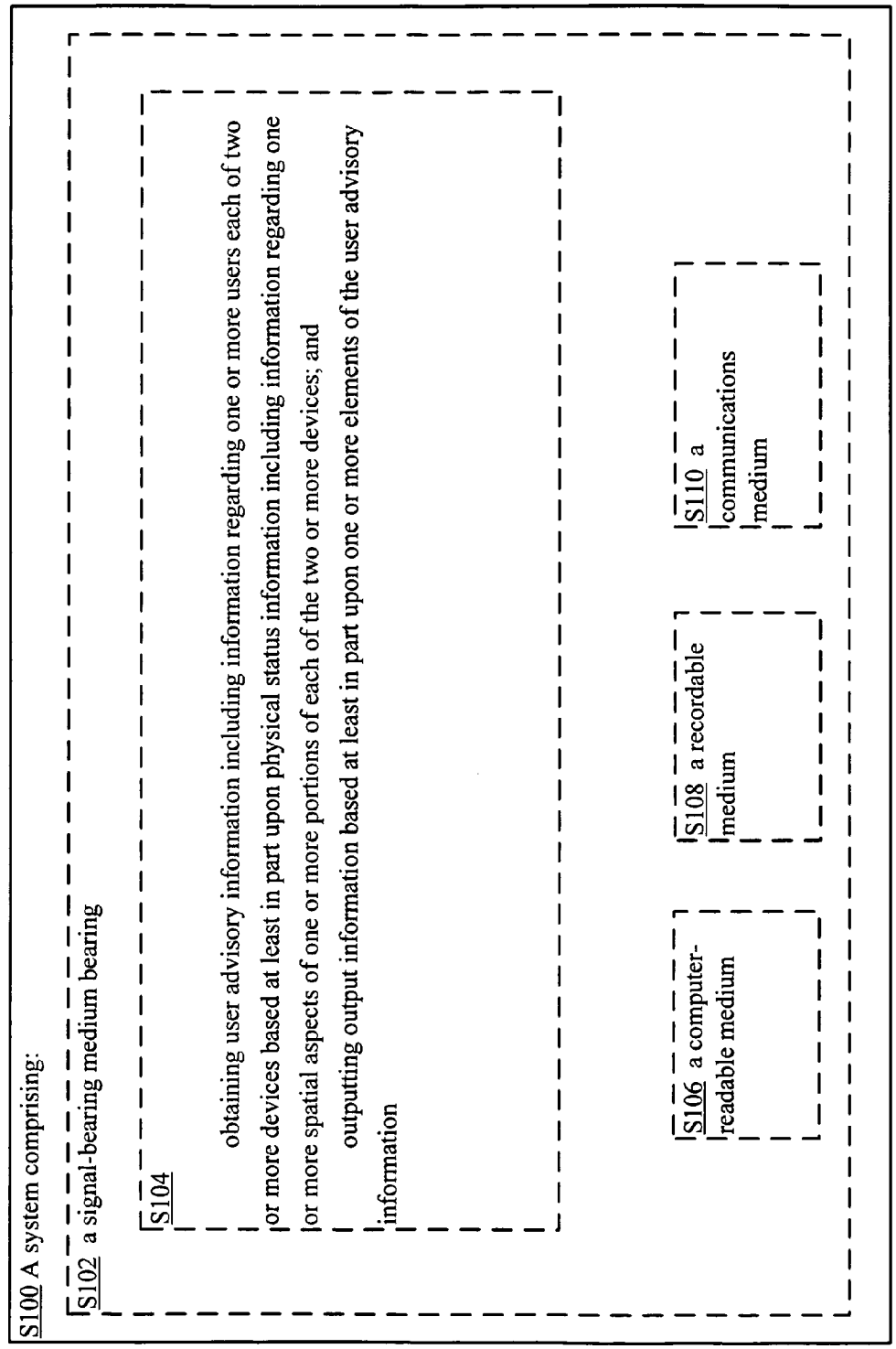
FIG. 41 illustrates a partial view of a system S100 that includes a computer program for executing a computer process on a computing device.

A partial view of a system S100 is shown in FIG. 41 that includes a computer program S104 for executing a computer process on a computing device. An implementation of the system S100 is provided using a signal-bearing medium S102 bearing one or more instructions for obtaining user advisory information including information regarding one or more users each of two or more devices based at least in part upon physical status information including information regarding one or more spatial aspects of one or more portions of each of the two or more devices. An exemplary implementation may be, executed by, for example, the communication unit 112 of the object 12 of FIG. 10 receiving through one or more of the transceiver components 156 user advisory information (e.g. including M1 and M2 as depicted in FIG. 14 and in FIG. 15) from the advisory system 118 of FIG. 3. In implementations the user advisory information can include information regarding one or more users each of two or more devices based at least in part upon physical status information including information regarding one or more spatial aspects of one or more portions of each of the two or more devices (e.g. S1 and S2 depicted as being sent from the objects 12 in FIG. 15).

The implementation of the system S100 is also provided using a signal-bearing medium S102 bearing one or more instructions for outputting output information based at least in part upon one or more elements of the user advisory information. An exemplary implementation may be executed by, for example, the advisory output 104 of FIG. 1. An exemplary implementation may include the advisory output 104 receiving information containing advisory based content from the advisory system 118 either externally (such as "M" depicted in FIG. 14) and internally (such as from the advisory resource 102 to the advisory output within the advisory system, for instance, shown in FIG. 14). After receiving the information containing advisory based content, the advisory output 104 can output information (e.g. A1 and A2 of FIG. 14 and FIG. 15) based at least in part upon one or more elements of the user advisory information.

The one or more instructions may be, for example, computer executable and/or logic-implemented instructions. In some implementations, the signal-bearing medium S102 may include a computer-readable medium S106. In some implementations, the signal-bearing medium S102 may include a recordable medium S108. In some implementations, the signal-bearing medium S102 may include a communication medium S110.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those of ordinary skill in the art will recognize that it is common within the art to describe devices and/or processes in the fashion set forth herein, and thereafter use engineering practices to integrate such described devices and/or processes into information processing systems. That is, at least a portion of the devices and/or processes described herein can be integrated into an information processing system via a reasonable amount of experimentation. Those having skill in the art will recognize that a typical information processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical information processing system may be implemented utilizing any suitable commercially available components, such as those typically found in information computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All of the above U.S. patents, U.S. patent application publications, U.S. patent applications, foreign patents, foreign patent applications and non-patent publications referred to in this specification and/or listed in any Application Information Sheet are incorporated herein by reference, to the extent not inconsistent herewith.

What is claimed is:

1. A method at least partially performed using one or more processing components, the method comprising:
   detecting first geographical position information associated with at least one display and second geographical position information associated with at least one device;
   determining one or more adjustments regarding visual placement or appearance of content displayed on the at least one display based at least partly on the first geographical position information associated with the at least one display and the second geographical position information associated with the at least one device; and
   modifying display of the content on the at least one display in accordance with the one or more determined adjustments.

2. A system comprising:
   circuitry configured for detecting first geographical position information associated with at least one display and second geographical position information associated with at least one device;
   circuitry configured for determining one or more adjustments regarding visual placement or appearance of content displayed on the at least one display based at least partly on the first geographical position information associated with the at least one display and the second geographical position information associated with the at least one device; and
   circuitry configured for modifying display of the content on the at least one display in accordance with the one or more determined adjustments.

3. The system of claim 2, further comprising:
   circuitry configured for receiving one or more elements of physical status information from the at least one display.

4. The system of claim 2, further comprising:
   circuitry configured for obtaining physical status information regarding at least one user.

5. The system of claim 2, further comprising:
   circuitry configured for obtaining one or more spatial aspects of at least one user through at least in part one or more techniques involving one or more photographic aspects.

6. The system of claim 2, further comprising:
   circuitry configured for determining one or more modifications regarding one or more locations of the at least one display.

7. A system comprising:
   means for detecting first geographical position information associated with at least one display and second geographical position information associated with at least one device;
   means for determining one or more adjustments regarding visual placement or appearance of content displayed on the at least one display based at least partly on the first geographical position information associated with the at least one display and the second geographical position information associated with the at least one device; and
   means for modifying display of the content on the at least one display in accordance with the one or more determined adjustments.

8. The system of claim 2, wherein the circuitry configured for detecting first geographical position information associated with at least one display and second geographical position information associated with at least one device comprises:
   circuitry configured for detecting first geographical position information associated with at least one display and second geographical position information associated with at least one cellular phone device.

9. The system of claim 8, further comprising:
   circuitry configured for determining relative orientation of and distance between the at least one display and the at least one cellular phone device based at least partly on the first geographical position information associated with the at least one display and the second geographical position information associated with the at least one cellular phone device.

10. The system of claim 9, wherein the circuitry configured for determining one or more adjustments regarding visual placement or appearance of content displayed on the at least one display based at least partly on the first geographical position information associated with the at least one display and the second geographical position information associated with the at least one device comprises:
    circuitry configured for determining one or more adjustments regarding placement and size of content displayed on the at least one display based at least partly on a determined relative orientation of and distance between the at least one display and the at least one cellular phone device.

11. The system of claim 10, wherein the circuitry configured for modifying display of the content on the at least one display in accordance with the one or more determined adjustments comprises:
    circuitry configured for modifying placement and size of the content on the at least one display in accordance with the one or more determined adjustments.

12. The system of claim 11, further comprising:
    circuitry configured for outputting one or more instructions to control at least one robotic system to reposition the at least one display from at least one first position to at least one second position based at least partly on a determined relative orientation of and distance between the at least one display and the at least one cellular phone device.

* * * * *